(12) United States Patent
Reches

(10) Patent No.: US 9,631,100 B2
(45) Date of Patent: Apr. 25, 2017

(54) ANTIFOULING MATERIALS

(71) Applicant: YISSUM RESEARCH DEVELOPMENT COMPANY OF THE HEBREW UNIVERSITY OF JERUSALEM LTD., Jerusalem (IL)

(72) Inventor: Meital Reches, Bet Hasmonai (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 0 days.

(21) Appl. No.: 14/764,765

(22) PCT Filed: Jan. 30, 2014

(86) PCT No.: PCT/IL2014/050106
§ 371 (c)(1),
(2) Date: Jul. 30, 2015

(87) PCT Pub. No.: WO2014/118779
PCT Pub. Date: Aug. 7, 2014

(65) Prior Publication Data
US 2015/0368480 A1  Dec. 24, 2015

Related U.S. Application Data

(60) Provisional application No. 61/758,875, filed on Jan. 31, 2013.

(51) Int. Cl.
| C07K 7/00 | (2006.01) |
| C09D 5/16 | (2006.01) |
| C07K 5/06 | (2006.01) |
| C07K 5/08 | (2006.01) |
| C09D 5/00 | (2006.01) |
| C07K 5/065 | (2006.01) |
| C07K 5/087 | (2006.01) |
| C07K 7/06 | (2006.01) |

(52) U.S. Cl.
CPC ........ *C09D 5/1625* (2013.01); *C07K 5/06078* (2013.01); *C07K 5/06191* (2013.01); *C07K 5/0812* (2013.01); *C07K 5/0827* (2013.01); *C07K 7/06* (2013.01); *C09D 5/00* (2013.01)

(58) Field of Classification Search
None
See application file for complete search history.

(56) References Cited

U.S. PATENT DOCUMENTS

2006/0241281 A1  10/2006  Messersmith et al.
2008/0089032 A1   4/2008  Chao et al.

FOREIGN PATENT DOCUMENTS

WO  2008089032 A1  7/2008
WO  2011122392 A1  10/2011

OTHER PUBLICATIONS

Bois-Choussy et al, "Total Synthesis of an Atropdiastereomer of RP-66453 and Determination of Its Absolute Configuration" XP055123529 42 (35) : 4238-4241 (Sep. 15, 2003).
Dalsin et al "Mussel Adhesive Protein Mimetic Polymers for the Preparation of Nonfouling Surfaces" JACS Articles. 125 : 4253-4258 (2003).
http://biomaterials.bme.northwestern.edu/mussel.asp (2015).

*Primary Examiner* — Jeanette Lieb
(74) *Attorney, Agent, or Firm* — Browdy and Neimark, PLLC

(57) ABSTRACT

The invention provided herein presents a novel family of antifouling agents based on hydroxylated and fluorinated compounds.

19 Claims, 14 Drawing Sheets

Fig. 3A  Fig. 3B  Fig. 3C
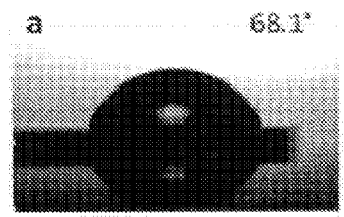
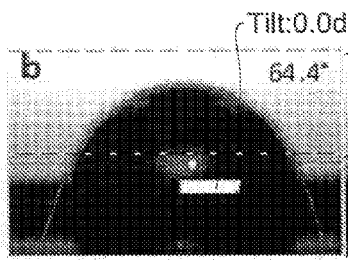
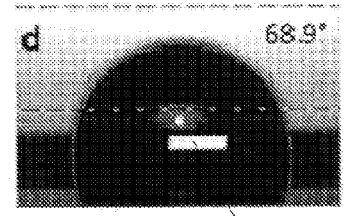
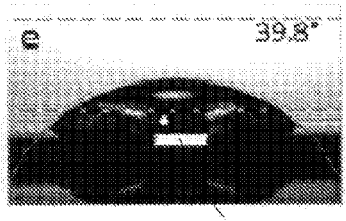
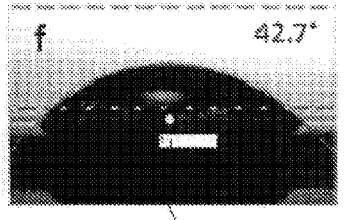
Fig. 3D  Fig. 3E  Fig. 3F
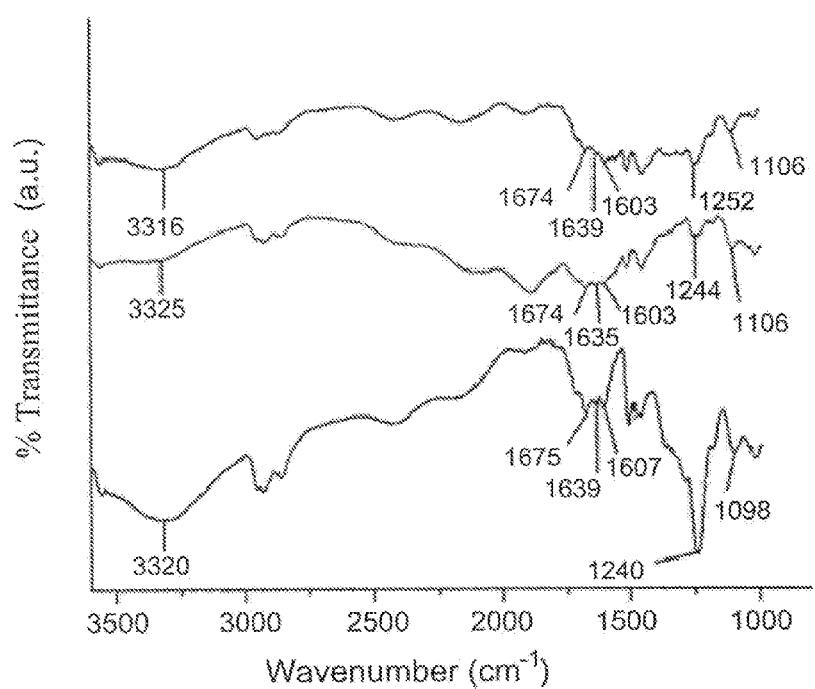
Fig. 4

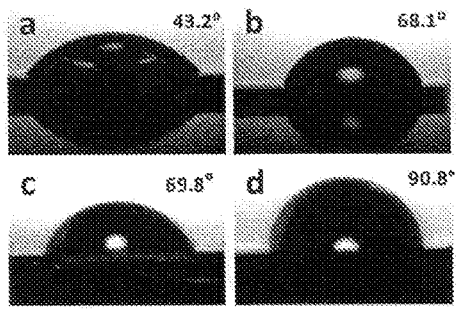
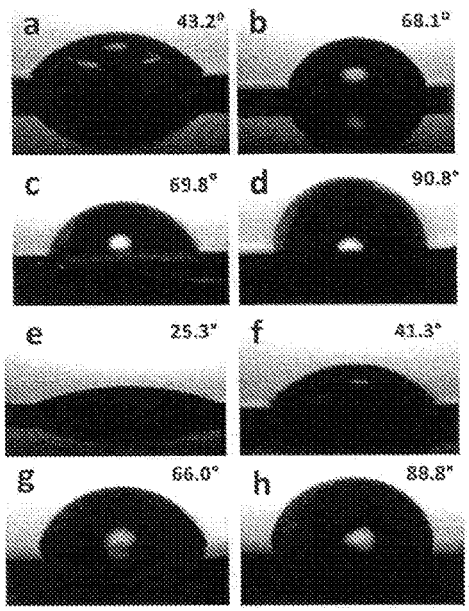
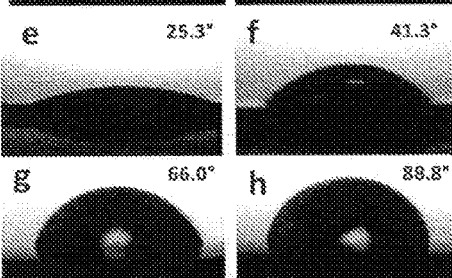
Fig. 5A  Fig. 5B  Fig. 5C  Fig. 5D  Fig. 5E  Fig. 5F  Fig. 5G  Fig. 5H
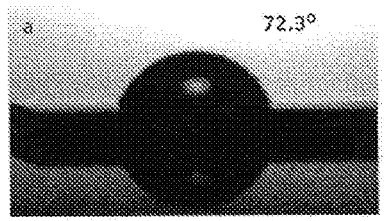 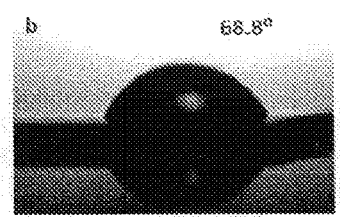 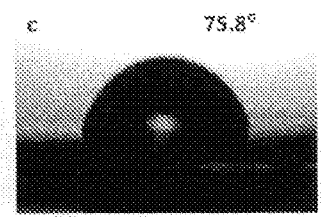
Fig. 6A  Fig. 6B  Fig. 6C
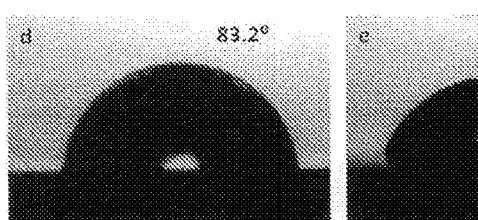
Fig. 6D  Fig. 6E

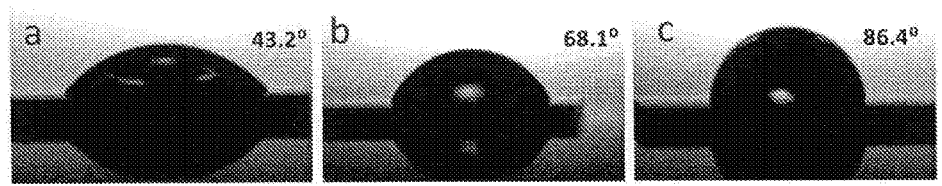
Fig. 7A  Fig. 7B  Fig. 7C
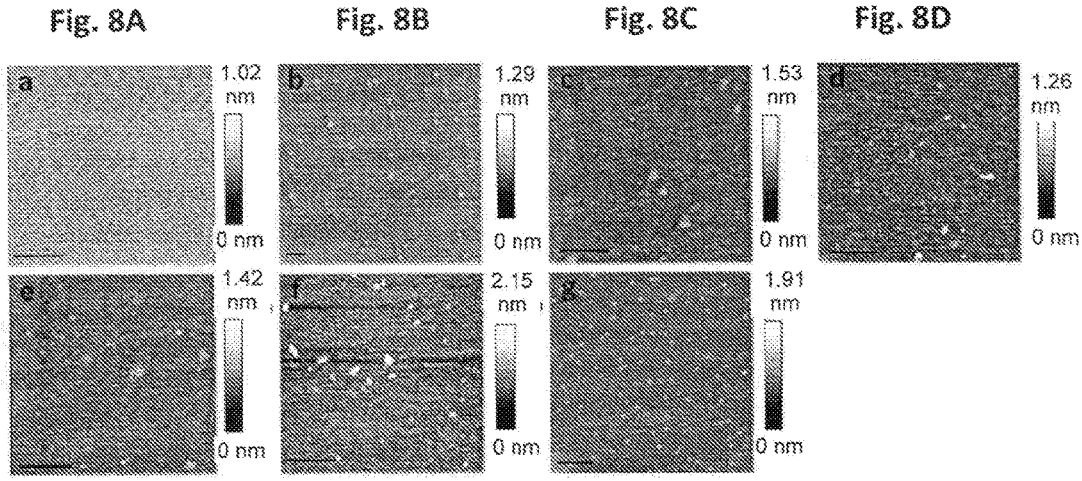
Fig. 8A  Fig. 8B  Fig. 8C  Fig. 8D
Fig. 8E  Fig. 8F  Fig. 8G

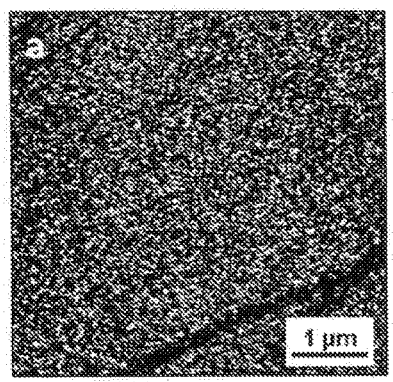
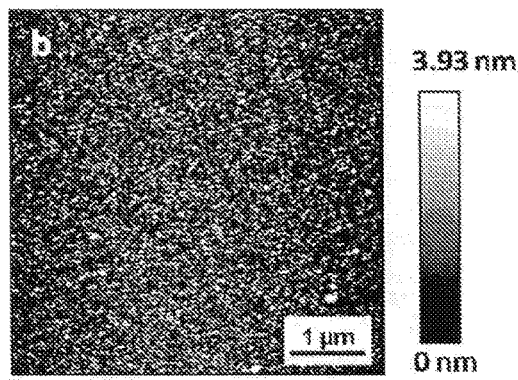
Fig. 9A                Fig. 9B
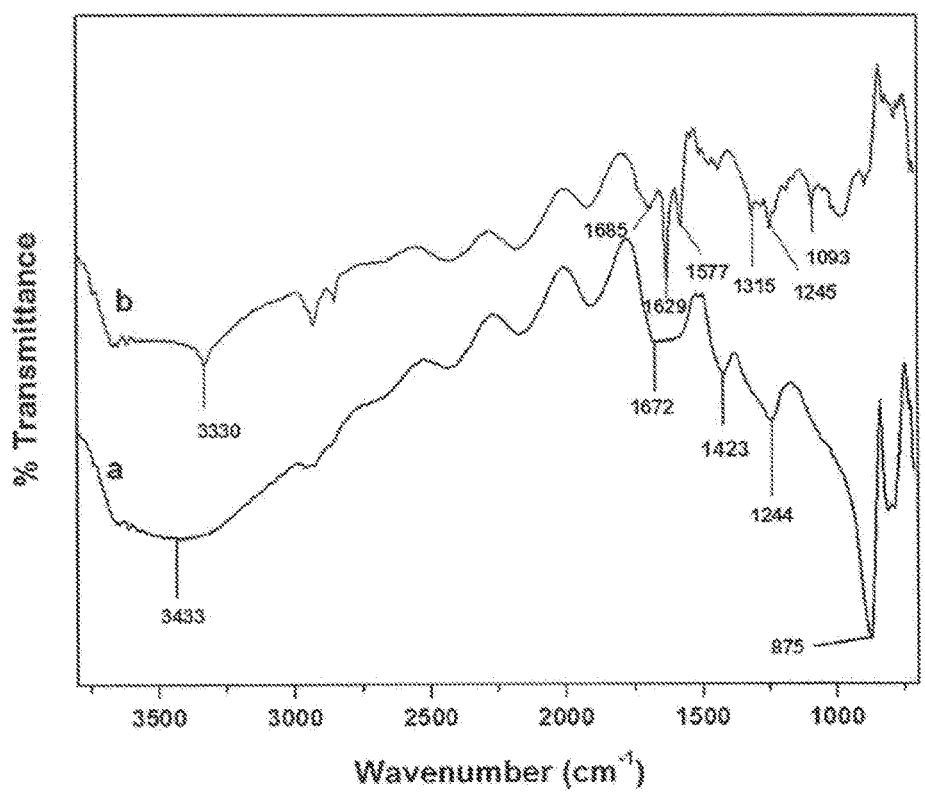
Fig. 10

Fig. 18A
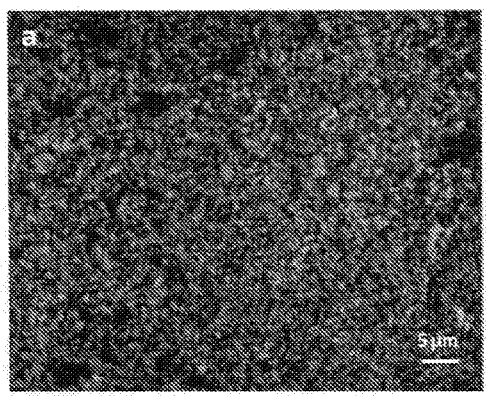
Fig. 18B
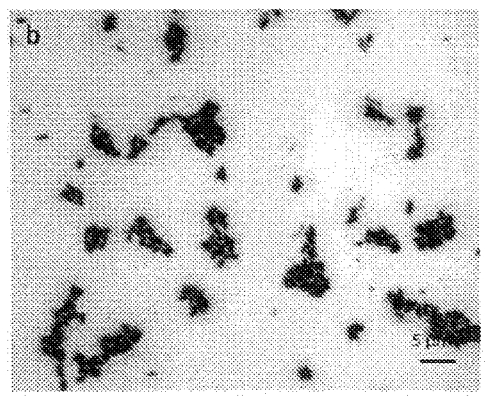
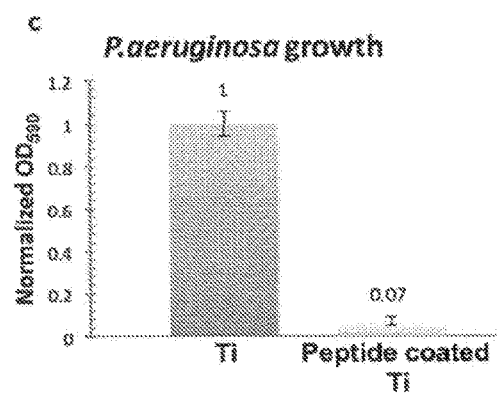
Fig. 18C
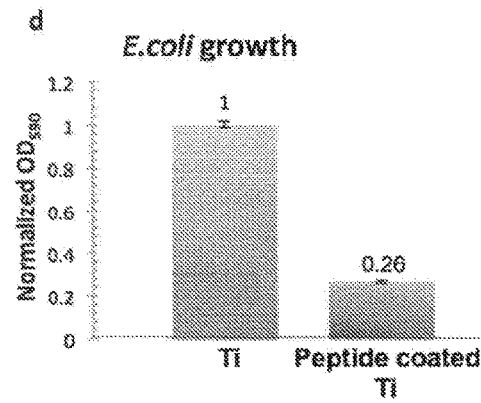
Fig. 18D

ANTIFOULING MATERIALS

FIELD OF THE INVENTION

The present invention is generally concerned with antifouling agents and uses thereof.

BACKGROUND

Biofouling is a process in which organisms and their by-products encrust a surface. In the case of bacteria, this process leads to the formation of a well-defined bacterial network, termed biofilm. Biofilms provide the bacteria with superior survival properties under exposure to antibiotics. Biofilm formation on medical devices and implants leads to severe infection which may result in patient death.

The attachment of marine organisms to ships and other marine devices is a major issue in the marine industry as organisms such as barnacles and marine mussels form a thick heavy biolayer on the surface of the device. This added weight causes delay in transportation and a higher consumption of fuel. In addition, colonization of ship hulls has been linked to two major environmental pollutions which are emission of gases ($CO_2$, $CO$, $SO_2$, and $NOx$) into the atmosphere and the introduction of invasive species to marine habitats.

Other industries using water in their processes, for example cooling towers and turbines, struggle constantly with biofouling buildup and clogging of pipes.

Biofouling initiates with the adsorption of proteins and polysaccharides onto a substrate, therefore many antifouling approaches aim to avoid biofouling by preventing protein adsorption or its degradation. These approaches include both chemical and topographical modification of a surface.

Antifouling materials prevent organisms from attaching to a surface. The challenges in designing such materials are in the ability to synthesize a material that prevents the attachment of the organism to the surface, performing in an authentic environment, and meanwhile does not have an effect on its surrounding environment by releasing toxic molecules. Antifouling materials such as paints and metal nanoparticles prevent the attachment of these organisms to a substrate, but they are toxic and harmful to the environment.

Immobilizing PEG is one of the most commonly used approaches to impart protein resistance to a surface. The antifouling properties of PEG-based coatings have been widely known. The physical adsorption or covalent attachment of PEG chains cannot usually reduce protein adsorption below a certain limit because of steric factors that limit the density of the attached polymer chains. In addition, PEG has a high tendency to undergo autoxidation.

Physical approaches to antifouling include the use of UV and ultrasonication treatments of the substrate.

SUMMARY OF THE INVENTION

High quality antifouling materials are desirable as they provide a good solution to biofouling processes and formation of biofilms on a surface. Conventional antifouling materials present several drawbacks, as many of these antifouling materials are toxic (or release of toxic materials to the environment), instable, inefficient or are limited in preventing (or complete diminishing) biofouling, expensive and produced via complicated manufacturing processes which at times require expensive equipment for their manufacture.

The inventors of the present invention have developed a family of novel and highly improved antifouling materials which spontaneously self-assemble on a surface, and which effectively prevent, diminish or decrease fouling of the surface. The self assembly, which enables the formation of an ordered film or as active particulate materials, is made possible by the bifunctional nature of the materials. This directed self assembly permits formation of an ordered film or layer of the bifunctional materials which possesses a high density of antifouling moieties extending outwards from the surface of the material.

In one aspect of the invention, there is provided a compound comprising at least one antifouling moiety (or group) and at least one surface-adsorbing moiety (or group), wherein the at least one antifouling moiety is selected amongst fluorine (—F) and a group comprising a fluorine atom and said at least one surface-adsorbing moiety is selected amongst 3,4-dihydroxy-L-phenylalanin (DOPA) and DOPA containing groups.

In another aspect, there is provided a bifunctional compound comprising at least one antifouling moiety (or group) and at least one surface-adsorbing moiety (or group), wherein the at least one antifouling moiety is selected amongst fluorine (—F) and a group comprising a fluorine atom and said at least one surface-adsorbing moiety is selected amongst dihydroxy-amino acid and dihydroxy-amino acid containing groups, said at least one antifouling moiety and said at least one surface-adsorbing moiety being associated to each other via a covalent bond or via a linker group, as defined hereinbelow. In another aspect, there is provided a bifunctional compound comprising at least one antifouling moiety (or group) and at least one surface-adsorbing moiety (or group), wherein the at least one antifouling moiety is selected amongst fluorine (—F) and a group comprising a fluorine atom and said at least one surface-adsorbing moiety is selected amongst 3,4-dihydroxy-L-phenylalanin (DOPA) and DOPA containing groups, said at least one antifouling moiety and said at least one surface-adsorbing moiety being associated to each other via a covalent bond or via a linker group, as defined hereinbelow.

In another aspect, there is provided an antifouling material comprising at least one antifouling moiety (or group) and at least one surface-adsorbing moiety (or group), wherein the at least one antifouling moiety is selected amongst fluorine (—F) and a group comprising a fluorine atom and said at least one surface-adsorbing moiety is selected amongst 3,4-dihydroxy-L-phenylalanin (DOPA) and DOPA containing groups, said at least one antifouling moiety and said at least one surface-adsorbing moiety being associated to each other via a covalent bond or via a linker group, as defined hereinbelow. In another aspect, there is provided a compound of the general formula A-L-F, wherein A is a surface-adsorbing moiety, L is a covalent bond or a linker moiety linking A and F, and F is an antifouling moiety, and wherein each of A, L and F are associated to each other as provided in the above formula via a non-hydrolysable bond. In some embodiments, the non-hydrolysable bond is a covalent bond.

In some embodiments of any of the invention various aspects, the compound of the invention is an antifouling agent capable of preventing or arresting adsorption of organic and/or bio-organic materials (polymers) to a surface (an article's surface).

In some embodiments, the compound of the invention is an antifouling agent capable of preventing or arresting adsorption of proteins and/or (poly)saccharides and/or (poly)lipids to a surface.

In yet further embodiments, the compound of the invention is an antifouling agent capable of preventing or arresting adsorption of secretion products of cells of multi-cellular organisms or of microorganisms to a surface.

In yet further embodiments, the compound of the invention is an antifouling agent capable of preventing or arresting adsorption of cells of multi-cellular organisms or of micro-organisms to a surface, as further detailed hereinbelow.

The surface-adsorbing moiety being DOPA or a DOPA containing moiety is selected to adhere to or associate with a surface or a region of a surface which protection against fouling is desired. The term "associate" or "adhere" as used herein refers to any physical or chemical interaction to be formed between the DOPA group or any atom thereof, or any DOPA containing moiety or any atom thereof, and a surface region. The association may be via Van-der-Walls, coordinative, covalent, ionic, electrostatic, dipole-dipole, or hydrogen association (bond or interaction).

Independent on the actual nature of the surface-adsorbing group, namely whether it is DOPA or a DOPA derivative, and whether association occurs via a single atom or group or via multiple atoms or groups of atoms, the surface-adsorbing moiety (element) is capable of adhering and/or capable of maintaining the surface adherence to any surface material as defined hereinbelow. The surface adherence may be maintained even under non-dry conditions such as under aquatic environment, and also under harsher conditions such as high salt concentrations.

In some embodiments, the compounds of the invention comprise one or more DOPA or DOPA containing groups. As known, DOPA comprises two hydroxyl (—OH) groups. Without wishing to be bound by theory, it is believed that surface adsorption occurs via one or both of said hydroxyl groups. In some embodiments, the DOPA group or a moiety comprising said DOPA may be modified to comprise one or more additional hydroxyl groups.

In some embodiments, the surface-adsorbing moiety is DOPA or a moiety comprising DOPA. In some embodiments, the moiety comprising DOPA is an organic material selected from amino acids and aliphatic materials. In some embodiments, the organic material is an amino acid. In another embodiment, the material is a peptide.

In some embodiments, the surface-adsorbing moiety is DOPA being linked, associated or bonded to an atom along the linker moiety L, as further defined herein.

In some embodiments, the compound comprising a DOPA unit as well as at least one additional hydroxylated moiety. The hydroxylated moiety may be selected amongst mono-, di-, tri-, tetra- or multiply-hydroxylated alkyls and aryl groups and hydroxylated amino acids.

The linker moiety L associating the surface adsorbing moiety and the antifouling moiety may have a backbone structure to which both functional moieties are bonded or with which they are associated. In some embodiments, the backbone structure is further substituted by pendent groups as explained hereinbelow. The backbone structure may be composed of carbon atoms and may include one or more heteroatoms such as N, O, S, and P atoms.

In some cases, the linker moiety may not be necessary as the two functional moieties may be associated or bonded directly to each other. Thus, in some embodiments, the linker moiety is absent or is a bond associating the two functional moieties (the bond being selected from covalent and ionic bonds).

In some embodiments, where the linker moiety is present its backbone may comprise one or more carbon atoms. The shortest backbone may be a one-carbon chain.

In some embodiments, the linker backbone may be selected from substituted or unsubstituted carbon chain which may be saturated or unsaturated, having only single bonds, hydrocarbons comprising one or more double bonds, or one or more triple bonds, or comprising any one or more functional groups which may be pendent to the backbone moiety or as an interrupting group (being part of the backbone).

In some embodiments, the backbone comprises one or more inner-chain aryl groups.

In some embodiments, the linker moiety is an organic backbone moiety selected from substituted or unsusbtituted oligomer (having between 2 and 11 repeating units) or polymer (having at least 12 repeating units).

In some embodiments, the linker moiety is an organic backbone moiety selected from amino acids and peptides.

In some embodiments, the backbone may comprise between 1 to 40 carbon atoms or hydrocarbon groups or any heteroatom which is positioned along the backbone (in the main chain). In some embodiments, the backbone comprises between 1 to 20 carbon atoms. In some embodiments, the backbone comprises between 1 to 12 carbon atoms. In some embodiments, the backbone comprises between 1 to 8 carbon atoms. In some embodiments, the backbone comprises 1 or 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 carbon atoms.

In some embodiments, the linker moiety is constructed of a predetermined number of repeating units which may or may not be randomly structured along the backbone. The linker moiety may be substituted by one or more functional groups such as substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heterocyclyl, substituted or unsubstituted —NR$_1$R$_2$, substituted or unsubstituted —OR$_3$, substituted or unsubstituted —SR$_4$, substituted or unsubstituted —S(O)R$_5$, substituted or unsubstituted alkylene-COOH, and substituted or unsubstituted ester. Each of the abovementioned groups is as defined hereinebelow.

The variable group denoted by "R" (including any one of R$_1$, R$_2$, R$_3$, R$_4$, R$_5$) refers to one or more group selected from hydrogen, alkyl, alkenyl, alkynyl, cycloalkyl, cycloalkenyl, cycloalkynyl, aryl, heteroaryl, heterocyclyl, halogen, alkylene-COOH, ester, —OH, —SH, and —NH$_2$, as defined herein or any combination thereof.

Each of the abovementioned groups, as indicated, may be substituted or unsubstituted. The substitution may also be by one or more R, selected from hydrogen, alkyl, alkenyl, alkynyl, cycloalkyl, cycloalkenyl, cycloalkynyl, aryl, heteroaryl, heterocyclyl, halogen, alkylene-COOH, ester, —OH, —SH, and —NH$_2$. In some embodiments, the number of R groups may be 0 or 1 or 2 or 3 or 4 or 5 or 6 or 7 or 8 or 9 or 20.

In some embodiments, backbone chain comprises one or more heteroatom (e.g., N, O, S and P). In some embodiments, backbone chain comprises inner-chain ester and/or carbonyl and/or amine group and/or amide group.

In some embodiments, the backbone chain is of the general structure

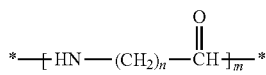

wherein
each * denotes a point of connectivity;
n is between 0 and 40; and
m is between 1 and 40.

In some embodiments, n is between 1 and 12. In some embodiments, n is between 1 and 8. In some embodiments, n is between 1 and 6.

In some embodiments, m is between 1 and 20. In some embodiments, m is between 1 and 12. In some embodiments, m is between 1 and 8. In some embodiments, m is between 1 and 6.

In some embodiments, one or more of the $(CH_2)_n$ groups are substituted. In some embodiments the substitution group is a substituted or unsubstituted phenyl. In some embodiments, the substitution group is hydroxylated or fluorinated phenyl.

In some embodiments, the backbone chain comprises an amino acid groups, and thus in the above general formula of a representative linker backbone, the repeating unit is an α- or β-amino acid (wherein n is 1, or n is 2, respectively).

In some embodiments, the linker moiety L is an amino acid or a peptide comprising 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 amino acids.

In some embodiments, the compounds of the invention are constructed of two amino acids bonded to each other via an amide bond (constituting the linker L), wherein one amino acid is DOPA and the other is a fluorinated amino acid, as described herein. In some embodiments, the compounds are constructed of two amino acids: DOPA and a fluorinated amino acid, said two amino acids being associated to each other via a linker moiety as described herein. In some embodiments, the linker moiety is one or more amino acid.

In some embodiments, the backbone comprises one or more surface adsorbing moieties and one or more antifouling moieties.

In some embodiments, the backbone comprises 1 or 2 or 3 or 4 or 5 or 6 or 7 or 8 or 9 or 10 or 11 or 12 or 13 or 14 or 15 or 16 or 17 or 18 or 19 or 20 surface-adsorbing moieties. In some embodiments, the backbone comprises 1 or 2 or 3 or 4 or 5 or 6 or 7 or 8 or 9 or 10 or 11 or 12 or 13 or 14 or 15 or 16 or 17 or 18 or 19 or 20 antifouling moieties.

In some embodiments, the antifouling moieties are bonded to the backbone at one end and the surface-adsorbing moieties at the other end of the backbone. In other embodiments, the antifouling moieties and the surface-adsorbing moieties are at alternating positions along the backbone. In other embodiments, the antifouling moieties and the surface-adsorbing moieties are randomly positioned along the backbone.

In some embodiments, the backbone comprises one or more amino acids units or hydrocarbon units, the backbone having a plurality of surface-adsorbing moieties and a plurality of antifouling moieties, wherein the distance between two moieties, either surface-adsorbing or antifouling moieties, does not exceed 12 units, 6 units, 3 units or 1 to 5 units.

In some embodiments, the backbone comprises or consists a peptide of two or more amino acids. In some embodiments, the compounds of the invention are peptides having at least two amino acids, at least one DOPA and at least fluorinated group, which may or may not be a fluorinated amino acid.

In some embodiments, the peptide comprises between 2 and 40 amino acids. In some embodiments, the peptide comprises between 2 and 20 amino acids. In some embodiments, the peptide comprises between 2 and 12 amino acids. In some embodiments, the peptide comprises between 2 and 8 amino acids. In other embodiments, the peptide comprises between 2 and 6 amino acids, or between 2 and 4 amino acids, or has 2 or 3 amino acids. In some embodiments, the peptide comprises 2, or 3, or 4, or 5, or 6, or 7, or 8 or 9 or 10 or 11 or 12 amino acids.

In some embodiments, the compounds of the invention are peptides, as defined, having at least one surface-adsorbing amino acid and at least one antifouling amino acid. Where the peptide is constructed of two amino acids, one of which is an antifouling amino acid and the other is a surface-adsorbing amino acid. Wherein the number of amino acids in the peptide is greater than 2, the number of each type of amino acids may be varied in accordance with the target final use.

As known in the art, a "peptide" comprises amino acids, typically between 2 and 40, or between 2 and 20, or between 2 and 12 or between 2 and 8; each amino acid being bonded to a neighboring amino acid via a peptide (amide) bond. The peptidic backbone may be modified such that the bond between the N— of one amino acid residue to the C— of the next amino acid residue is altered to non-naturally occurring bonds by reduction (to —$CH_2$—NH—), alkylation (e.g., methylation) on the nitrogen atom, or the bonds replaced by amidic bond, urea bonds, sulfonamide bond, etheric bond (—$CH_2$—O—), thioetheric bond (—$CH_2$—S—), or —CS—NH. The peptide may further comprise one or more non-amino acid group.

The "amino acid" may be any natural or unnatural amino acid, an amino acid analog, α- or β-forms, or may be in either L- or D configurations. Amino acid analogs which may be used in a compound of the invention be chemically modified at either or both of their C-terminal and/or N-terminal; or chemically modified at a side-chain functional group (e.g., positioned at the α-position or any other pendant group).

The amino acid may be selected amongst alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine valine, pyrrolysine and selnocysteine; and amino acid analogs such as homo-amino acids, N-alkyl amino acids, dehydroamino acids, aromatic amino acids and α,α-disubstituted amino acids, e.g., cystine, 5-hydroxylysine, 4-hydroxyproline, a-aminoadipic acid, a-amino-n-butyric acid, 3,4-dihydroxyphenylalanine, homoserine, α-methylserine, ornithine, pipecolic acid, ortho, meta or para-aminobenzoic acid, citrulline, canavanine, norleucine, d-glutamic acid, aminobutyric acid, L-fluorenylalanine, L-3-benzothienylalanine and thyroxine.

In some embodiments, the amino acids are selected amongst aromatic amino acids. Non-limiting examples of aromatic amino acids include tryptophan, tyrosine, naphthylalanine, and phenylalanine. In some embodiments, the amino acids are phenylalanine or derivatives thereof.

In some embodiments, the phenylalanine derivatives is 4-methoxy-phenylalanine, 4-carbamimidoyl-1-phenylalanine, 4-chloro-phenylalanine, 3-cyano-phenylalanine, 4-bromo-phenylalanine, 4-cyano-phenylalanine, 4-hydroxymethyl-phenylalanine, 4-methyl-phenylalanine, 1-naphthyl-alanine, 3-(9-anthryl)-alanine, 3-methyl-phenylalanine, m-amidinophenyl-3-alanine, phenylserine, benzylcysteine, 4,4-biphenylalanine, 2-cyano-phenylalanine, 2,4-dichloro-phenylalanine, 3,4-dichloro-phenylalanine, 2-chloro-penylalanine, 3,4-dihydroxy-phenylalanine, 3,5-dibromotyrosine, 3,3-diphenylalanine, 3-ethyl-phenylalanine, 3,4-difluoro-phenylalanine, 3-chloro-phenylalanine, 3-chloro-phenylalanine, 2-fluoro-phenylalanine, 3-fluoro-phenylalanine, 4-amino-L-phenylalanine, homophenylalanine, 3-(8-hydroxyquinolin-3-yl)-1-alanine, 3-iodo-tyrosine, kynurenine, 3,4-dimethyl-phenylalanine, 2-methyl-phenylalanine, m-tyrosine, 2-naphthyl-alanine, 5-hydroxy-1-naphthalene, 6-hydroxy-2-naphthalene, meta-nitrotyrosine, (beta)-beta-hydroxy-1-tyrosine, (beta)-3-chloro-beta-hydroxy-1-tyrosine, o-tyrosine, 4-benzoyl-phenylalanine, 3-(2-pyridyl)-alanine, 3-(3-pyridyl)-alanine, 3-(4-pyridyl)-alanine, 3-(2-quinolyl)-alanine, 3-(3-quinolyl)-alanine, 3-(4-quinolyl)-alanine, 3-(5-quinolyl)-alanine, 3-(6-quinolyl)-alanine, 3-(2-quinoxalyl)-alanine, styrylalanine, pentafluoro-phenylalanine, 4-fluoro-phenylalanine, phenylalanine, 4-iodo-phenylalanine, 4-nitro-phenylalanine, phosphotyrosine, 4-tert-butyl-phenylalanine, 2-(trifluoromethyl)-phenylalanine, 3-(trifluoromethyl)-phenylalanine, 4-(trifluoromethyl)-phenylalanine, 3-amino-L-tyrosine, 3,5-diiodotyrosine, 3-amino-6-hydroxy-tyrosine, tyrosine, 3,5-difluoro-phenylalanine and/or 3-fluorotyrosine In some embodiments of the invention, the compounds are peptides having one or more surface-adsorbing amino acids grouped at the C-terminal of the peptide, and one or more antifouling amino acids grouped at the N-terminal of the peptide. In other embodiments, the surface-adsorbing amino acids are grouped at the N-terminal of the peptide, and the antifouling amino acids are grouped at the C-terminal of the peptide.

In some embodiments, at least one surface-adsorbing amino acids is positioned at one of the peptide termini (either the C-terminal or the N-terminal), and at least one antifouling amino acids is positioned at the other of the peptide termini.

In some embodiments, the at least one surface-adsorbing amino acids is positioned at a midpoint position between the C-terminal of the peptide and the N-terminal of the peptide, and one or more antifouling amino acids are positioned each at each of the peptide termini.

In some embodiments, the peptide may comprise any one or more amino acids along the chain, e.g., positioned between the termini functional amino acids, positioned randomly along the peptide or at specific positions thereof in order to affect one or more additional structural or functional attributes. In some embodiments, the one or more amino acids may or may not be aromatic amino acids.

The end C- or N-termini of the peptide may be modified to affect or modulate (increase or decrease or generally change) one or more property of the peptide, e.g., a structural change, hydrophobicity/hydrophilicity, charge, solubility, surface adhesion, toxicity to organisms, biocompetability, resistance to degradation in general and enzymatic degradation in particular and others. The C- or N-termini of the peptide may be chemically modified by forming an ester, an amide, or any other functional group at the desired position; such that the peptides may have an amine at one end thereof (the N-terminal) and a carboxyl group (the C-terminal) at the other end, or may have others groups at either of the termini.

The antifouling moiety renders compounds of the invention with the antifouling and anti-biofilms properties discussed herein. In some embodiments, in a compound of the invention, the antifouling moiety is a fluorine atom. In some embodiments, the antifouling moiety is a fluorinated moiety or substituent (a group comprising a fluorine atom). In some embodiments, the antifouling moiety comprises a C—F group.

In some embodiments, the antifouling moiety comprises one or more fluorine atoms and/or fluorinated moieties. In some embodiments, the antifouling moiety comprises 1 or 2 or 3 or 4 or 5 or 6 or 7 or 8 or 9 or 10 fluorine atoms and/or fluorinated moieties.

In some embodiments, the antifouling element is a fluorinated organic group. In some embodiments, the fluorinated organic group is F-substituted carbon group having a C—F bond, wherein the number of C—F bonds in the group may be one or more. In some embodiments, the antifouling moiety comprises 1 or 2 or 3 or 4 or 5 fluorine atoms. In some embodiments, the fluorinated carbon group comprises or consists —CF, —$CF_2$, and —$CF_3$.

In some embodiments, the fluorinated carbon group is a substituted or unsubstituted alkyl. In some embodiments, the antifouling moiety is an alkyl comprising 1 or 2 or 3 or 4 or 5 or 6 fluorine atoms. In some embodiments, the antifouling moiety is an alkyl having at least one fluorine atom on each carbon atom.

In other embodiments, the antifouling moiety is a fluorinated substituted or unsubstituted aryl. In some embodiments, the aryl comprises 1 or 2 or 3 or 4 or 5 fluorine atoms. In some embodiments, the aryl is perfluorinated.

In other embodiments, the aryl is a phenyl group. In other embodiments, the aryl is a heteroaryl group.

In some embodiments, the antifouling moiety comprises or consists one or more fluorinated amino acid moieties.

In some embodiments, the fluorinated amino acid, wherein the amino acid is as defined herein, is a fluorinated phenylalanine derivative, wherein the fluoride atom substitutes one or more phenyl ring positions. The substitution on the phenyl ring may be at the ortho, meta and/or para positions. The number of fluoride atoms may be 1, 2, 3, 4, or 5.

In some embodiments, the fluorinated phenylalanine is selected from o-fluorophenylalanine, m-fluorophenylalanine and p-fluorophenylalanine.

In some embodiments, the compound of the invention is a peptide which comprises between 2 and 12 or between 2 and 8 amino acids, each amino acid being selected from aromatic amino acids. In some embodiments, the peptide comprises DOPA. In other embodiments, the peptide comprises a fluorinated aromatic amino acid selected from o-fluorophenylalanine, m-fluorophenylalanine and p-fluorophenylalanine.

In some embodiments, the compound of the invention is a peptide comprising DOPA at one termini and a fluorinated aromatic amino acid selected from o-fluorophenylalanine, m-fluorophenylalanine and p-fluorophenylalanine at the other termini.

In some embodiments, the compound of the invention is a peptide comprising DOPA at a mid-point amino acid along the peptide and a fluorinated aromatic amino acid selected from o-fluorophenylalanine, m-fluorophenylalanine and p-fluorophenylalanine at the each of the peptide termini.

In some embodiments, the antifouling moiety of compounds of the invention constitute two antifouling amino acid residues, optionally bonded to each other. In some embodiments, the antifouling moiety constitutes two fluorinated amino acid residues, optionally bonded to each other. In some embodiments, the antifouling moiety constitutes at least two fluorinated amino acid residues, each being optionally bonded to the other.

As sated herein, compounds of the invention are generally bifunctional compounds which in some embodiments are used as antifouling agents for achieving inter alia one or more of the following:

- preventing or arresting or minimizing or diminishing adsorption of organic and/or bio-organic materials (polymers) to a surface (an article's surface);
- preventing or arresting or minimizing or diminishing adsorption of proteins and/or (poly)saccharides and/or (poly)lipids to a surface;
- preventing or arresting or minimizing or diminishing secretion from cells of multi-organism or of micro-organisms onto a surface; and
- preventing or arresting or minimizing or diminishing adsorption of cells of multi-organism or micro-organisms to a surface.

The compounds of the invention are capable of endowing a surface with which they are associated with the above attributes as they are capable of associating intimately with said surface region, and at the same time capable of forming a dense layer of exposed antifouling moieties which coat or film the surface region, thereby forming a protective coat, layer or film thereon. The compounds of the invention, in particular, the peptide of the invention comprise elements, in particular aromatic groups or aromatic amino acids which enable self-assembly of the compounds into ordered structures having specific directionality. Without wishing to be bound by theory, an ideal configuration for the self-assembled peptides result in a film as exemplary depicted in FIG. 1.

Thus, compounds of the invention may be of any structure as shown in Scheme 1 below.

The 6 exemplary structures of compounds shown in Scheme 1, the general structure A-L-F is shown, wherein A is a surface-adsorbing moiety, L is a covalent bond or a linker moiety linking A and F, and F is an antifouling moiety, and wherein each of A, L and F are associated to each other as provided in the above structures via a non-hydrolysable bond(s). Each of A, L and F are as defined hereinabove.

As depicted in Structure I, the linker L may be a linear or substantially linear structure having at one end a surface-adsorbing moiety A and at the other end an antifouling moiety F, wherein L may optionally be substituted. L may be a long or short linker moiety. L may be absent. Where L is present, it comprises at least one carbon atom.

In Structure II, the linker L associates a single surface-adsorbing moiety A with two antifouling moieties F. There may be in some embodiments, more than two antifouling moieties, each of which extending outwards away from the surface. While in Structure II the linker is bifurcated to provide two linking points, one for each antifouling moiety, the connectivity of the plurality of antifouling moieties may alternatively be along the backbone chain of the linker. In other words, the two antifouling moieties need not have a common bonding atom or group.

In Structure III, the linker L associates two surface-adsorbing moieties A with an antifouling moiety F. There may be in some embodiments, more than one antifouling moiety. While in Structure III the linker is bifurcated to provide two linking points, one for each surface-adsorbing moiety, the connectivity of the plurality of surface-binding moieties may alternatively be along the backbone chain of the linker. In other words, the two surface-binding moieties need not have a common bonding atom or group.

In Structure V a surface-adsorbing moiety A is positioned substantially mid-way on the backbone of the linker L with two linker arms extending therefrom, at the end of which an antifouling moiety is provided. Similarly, in Structure VI, two surface-adsorbing moieties are provided to link a single antifouling moiety.

The compounds of the invention may also be constructed to have longer linker backbones, with a plurality of surface-binding moieties and antifouling moieties positioned along the backbone to provide a more compact covering of a surface region. One such exemplary embodiments of compounds of the invention is depicted in Structure IV of Scheme 1.

In some embodiments, the compounds depicted in the Structures of Scheme 1 are each aliphatic compounds (L being an aliphatic backbone) having one or more antifouling (F) and surface-adsorbing (A) moieties.

In some embodiments, the linker backbone is a peptide.

Scheme 1

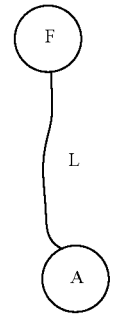

Structure I

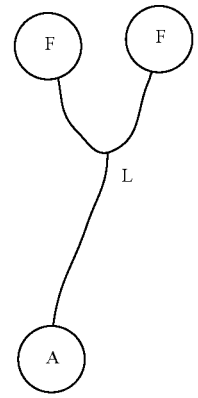

Structure II

Structure III

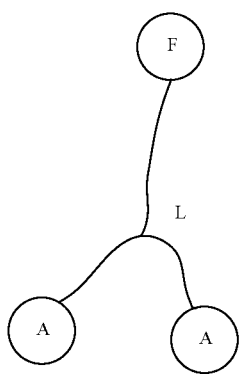

Structure IV

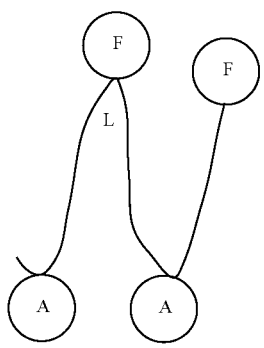

Structure V

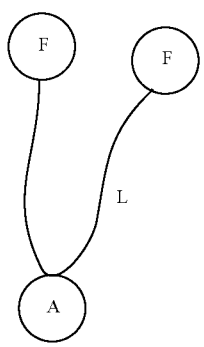

Structure VI

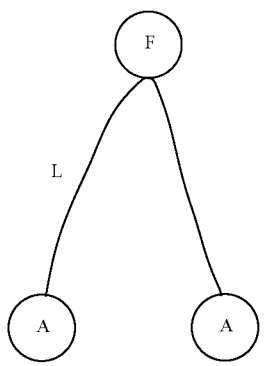

Exemplary, non-limiting examples of compounds according to the invention are Peptides herein designated Peptide 1-18.

Peptides of Group I are exemplified in non-limiting compounds of the invention designated Peptides 1-4.

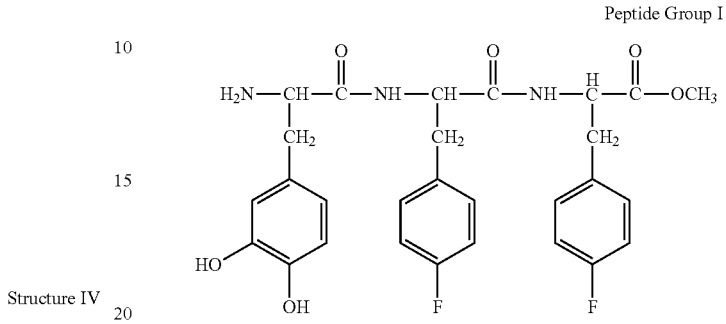

Peptide Group I

A perfluorinated derivative is designated Peptide 5.

A dipeptide derivative is designated Peptide 6.

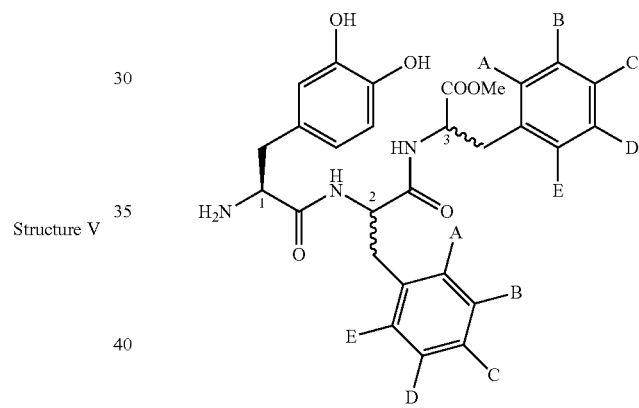

Peptide 1: (1S, 2S, 3S) A = B = D = E = ——H, C = ——F
Peptide 2: (1S, 2S, 3R) A = B = D = E = ——H, C = ——F
Peptide 3: (1S, 2R, 3S) A = B = D = E = ——H, C = ——F
Peptide 4: (1S, 2R, 3R) A = B = D = E = ——H, C = ——F
Peptide 5: (1S, 2S, 3S) A = B = C = D = E = ——F

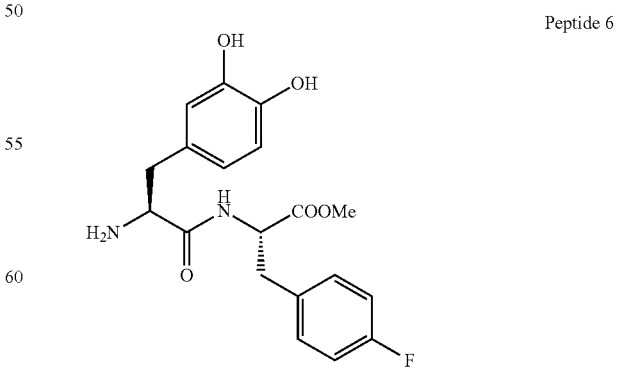

Peptide 6

Peptides of Group II are exemplified in non-limiting compounds of the invention designated Peptides 7-10.

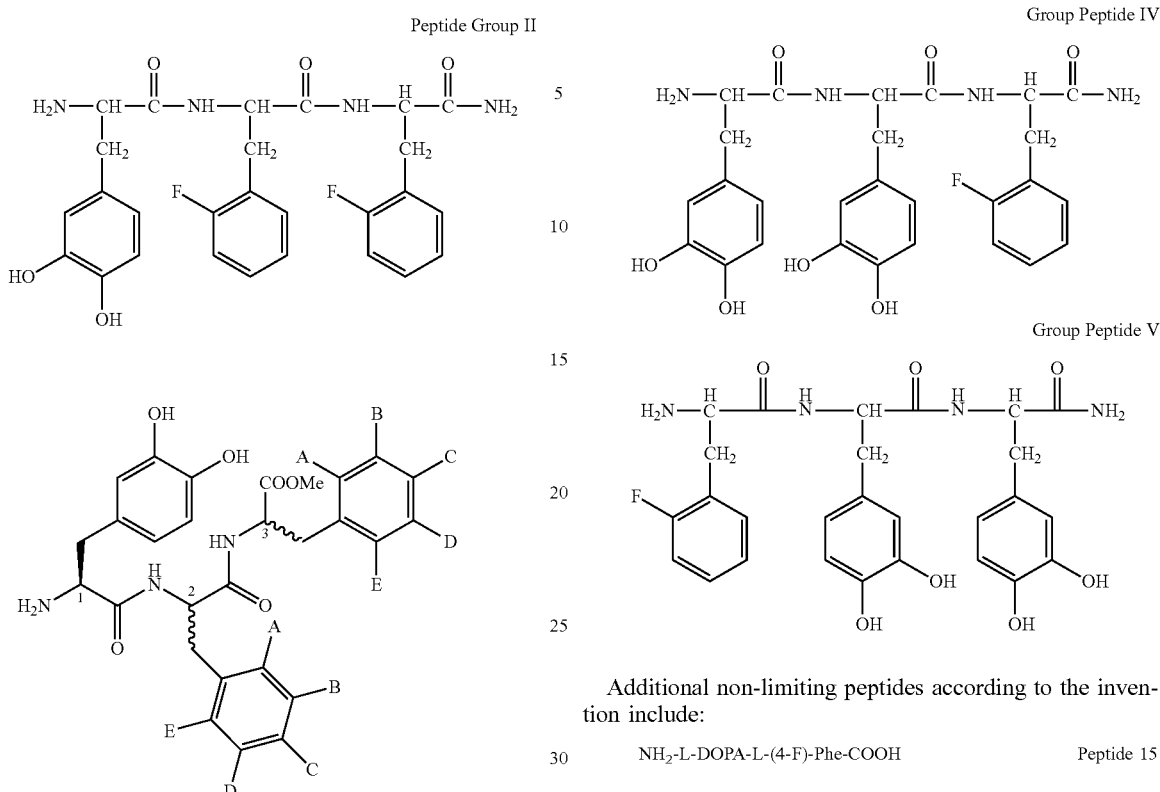

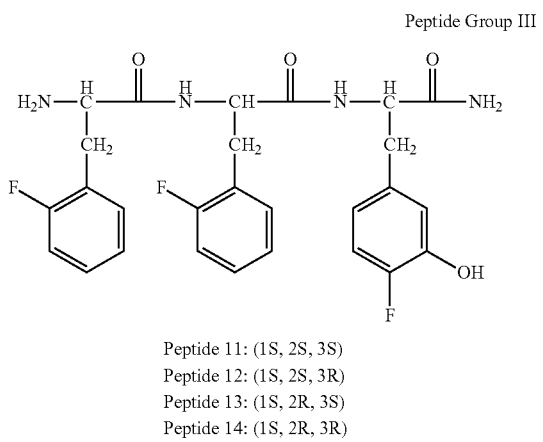 [SMILES: NC(=O)C(Cc1ccc(F)c(O)c1)NC(=O)C(Cc1ccccc1F)NC(=O)C(N)Cc1ccccc1F]

Peptide 11: (1S, 2S, 3S)
Peptide 12: (1S, 2S, 3R)
Peptide 13: (1S, 2R, 3S)
Peptide 14: (1S, 2R, 3R)

Similarly to Peptides 1 to 14 depicted above other peptides of the invention may comprise surface binding amino acids in a greater number (amount) as compared to the number of antifouling amino acids, e.g., fluorinated aromatic amino acids; such compounds having the structure depicted below for Group Peptide W and V:

Additional non-limiting peptides according to the invention include:

| | |
|---|---|
| NH$_2$-L-DOPA-L-(4-F)-Phe-COOH | Peptide 15 |
| NH$_2$-L-DOPA-D-(4-F)-Phe-COOH | Peptide 16 |
| NH$_2$-L-DOPA-L-(4-F)-Phe-L-(4-F)-Phe-COOMe | Peptide 17. |

As used above, the designation "(4-F)—" refers to para-fluoro derivatives.

As used above, the compounds of the invention may have one or more substituents on any of the atom thereof. In the compounds as defined:

"alkyl", "alkenyl" and "alkynyl" carbon chains, if not specified, refer to carbon chains each containing from 1 to 20 carbons, or 1 or 2 to 16 carbons, and are straight or branched. Each such group may be substituted. In some embodiments, the carbon chain contains 1 to 10 carbon atoms. In some embodiments, the carbon chain contains 1 to 6 carbon atoms. In some embodiments, the carbon chain contains 2 to 6 carbon atoms. Alkenyl carbon chains may contain from 2 to 20 carbons, or 2 to 18 carbons, or 2 to 16 carbons, or 2 to 14 carbons, or 2 to 12 carbons, or 2 to 10 carbons, or 2 to 8 carbons, or 2 to 6 carbons, or 2 to 4 carbons. The alkenyl carbon chain may similarly contain 1 to 8 double bonds, or 1 to 7 double bonds, or 1 to 6 double bonds, or 1 to 5 double bonds, or 1 to 4 double bonds, or 1 to 3 double bonds, or 1 double bond, or 2 double bonds. Alkynyl carbon chains from 2 to 20 carbons, or 2 to 18 carbons, or 2 to 16 carbons, or 2 to 14 carbons, or 2 to 12, or carbons 2 to 10 carbons, or 2 to 8 carbons, or 2 to 6 carbons, or 2 to 4 carbons. The alkynyl carbon chain may similarly contain 1 to 8 triple bonds, or 1 to 7 triple bonds, or 1 to 6 triple bonds, or 1 to 5 triple bonds, or 1 to 4 triple bonds, or 1 to 3 triple bonds, or 1 triple bond, or 2 triple bonds. Exemplary alkyl, alkenyl and alkynyl groups include, but are not limited to, methyl, ethyl, propyl, isopropyl, isobutyl, n-butyl, sec-butyl, tert-butyl, isohexyl, allyl (propenyl) and propargyl (propynyl).

"cycloalkyl" refers to a saturated mono- or multi-cyclic ring system, in certain embodiments of 3 to 10 carbon atoms, in other embodiments 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in some embodiments, may contain between 3 to 10 carbon atoms, in further embodiments, between 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion.

"aryl" refers to aromatic monocyclic or multicyclic groups containing from 6 to 10 carbon atoms. Aryl groups include, but are not limited to groups such as unsubstituted or substituted fluorenyl, unsubstituted or substituted phenyl, and unsubstituted or substituted naphthyl.

"heteroaryl" refers to a monocyclic or multicyclic aromatic ring system, in certain embodiments, of about 5 to about 15 members where one or more, in some embodiments 1 to 3, of the atoms in the ring system is a heteroatom, that is, an element other than carbon, including e.g., nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

"heterocyclyl" refers to a saturated mono- or multi-cyclic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidine, or the nitrogen may be quaternized to form an ammonium group where the substituents are selected as above.

"—$NR_1R_2$" refers to an amine group wherein $R_1$ and $R_2$ are independently selected from hydrogen, alkyl, alkenyl, alkenyl, cycloalkyl, cycloalkenyl, cycloalkynyl, aryl, heteroaryl, heterocyclyl, ester and carbonyl, each as defined herein or alternatively known in the art.

"—$OR_3$" refers to a hydroxyl group or an alkoxy group or derivative, wherein $R_3$ is selected from hydrogen, alkyl, alkenyl, alkenyl, cycloalkyl, cycloalkenyl, cycloalkynyl, aryl, heteroaryl, heterocyclyl, halogen, sulfinyl, ester and carbonyl.

"—$SR_4$" refers to a thiol group or a thioether group or derivative, wherein $R_4$ is selected from hydrogen, alkyl, alkenyl, alkenyl, cycloalkyl, cycloalkenyl, cycloalkynyl, aryl, heteroaryl, heterocyclyl, halogen, sulfinyl, ester and carbonyl.

"—$S(O)R_5$" refers to a sulfinyl group, wherein $R_5$ is selected from hydrogen, alkyl, alkenyl, alkenyl, cycloalkyl, cycloalkenyl, cycloalkynyl, aryl, heteroaryl, heterocyclyl, halogen, sulfinyl, ester and carbonyl.

"ester" refers to —$C(O)OR_8$ in which $R_8$ is selected from hydrogen, alkyl, alkenyl, alkenyl, cycloalkyl, cycloalkenyl, cycloalkynyl, aryl, heteroaryl, heterocyclyl, halogen, —$NR_1R_2$, sulfinyl, carbonyl, —$OR_3$, $SR_4$, —$S(O)R_5$ —OH, —SH and —NH.

The term "substituted" refers to any group or any ligand as defined herein above having (further substituted) one or more substituent, wherein the substituent is a ligand as defined herein above. In some embodiments, the substituent is selected from alkyl, alkenyl, alkynyl, cycloalkyl, cycloalkenyl, cycloalkynyl, aryl, heteroaryl, heterocyclyl, halogen, alkylene-COOH, ester, —OH, —SH, and —NH. In some embodiments, the number of substituents on a certain ligand is 0 or 1 or 2 or 3 or 4 or 5 or 6 or 7 or 8 or 9 or 20 substituents.

The compounds of the invention (e.g., peptide) have been manufactured according to known methods in the art. In some embodiments, the compounds have been synthesized using solid or solution phase synthesis.

The antifouling compounds of the invention may be formulated as ready-for-use products or as concentrates. The ready-for-use products may be in the form of powders, oil preparations (or dispersions), emulsions or aerosol formulations. The formulations comprising one or more compounds of the invention, in particular peptides of the invention, may comprise additional components, such as fixatives, co-solvents, plasticizers, dyes, color pigments, corrosion inhibitors, chemical stabilizers or any other additive.

The formulation and/or compounds may be applied by any method known in the art including brushing, spraying, roll coating, dipping, spin coating, dispensing, printing, ink-jet printing, stamping, drop casting and any combination thereof.

In another aspect, the invention provides a film comprising a compound according to the present invention.

In some embodiments, the film is obtainable by self-assembly of the compounds onto a surface, as discussed herein.

In some embodiments, the film comprises a peptide according to the invention.

In some embodiments, the film is antifouling and/or anti-biofilm.

The film may be a continuous film or comprise separate regions or domains. The number of different antifouling compounds in the film may be determined inter alia by the physical limit of the number of materials that may be put on a desired area, the chemical or physical nature of the compounds, and others.

In another aspect, the invention also provides use of at least one compound according to the invention for forming a film according to the invention.

The invention also provides a surface or an article (or device), wherein at least a region thereof is coated with an antifouling film according to the present invention.

The article or device may be any article, wherein antifouling properties are desired. Typically, the article is an article which experiences humidity or aquatic environments. The article or device may be any surface region of a marine vessel and/or a hull of a marine vessel and/or a medical device and/or a contact lens and/or a food processing apparatus and/or a drinking water dispensing apparatus and/or a pipeline and/or a cable and/or a fishing net and/or a pillar of a bridge and/or a surface region of a water immersed article, and/or others.

The adsorption properties of compounds of the invention are exceptionally improved and therefore, a film thereof may be formed on any surface material. The substrate may be of a flexible or rigid substrate, which may be substantially two-dimensional (a thin flat article) or three-dimensional. The surface of the article can be of any smoothness.

The surface may be selected, in a non-limiting fashion, from outdoor wood work, external surface of a central heating or cooling system, bathroom walls, hull of a marine vessel or any off-shore installations, surfaces in food production/packaging, surfaces in any industrial facility, surfaces in any medical facility, surfaces in any water facility and others. The surface material (of the article) may be any material selected from wood, glass, mica, plastics, ceramics, cement, metals, semiconductors, silicon surfaces (e.g., silicon wafer, a silicon wafer with a 100 nm titanium layer), carbon, hybrid materials (e.g., 400 mesh Copper-Formvar®/carbon grids), stainless steel, metal oxides, alumina and others.

The antifouling properties endowed by compounds of the invention are best appreciated by the observed prevention of accumulation of organisms or organism's secretion on a variety of surfaces. The organisms that participate in the fouling of surfaces in humid, salt water and fresh water environments include, for example, bacteria, diatoms, hydroids, algae, bryozoans, protozoans, ascidians, tube worms, asiatic clams, zebra mussels and barnacles. Thus, the compounds of the invention are capable of preventing both micro- and macrofouling, e.g., prevention of bacterial and viral adhesion as well as attachment of larger organisms or cells shed from bodies of multi cellular organisms.

In some embodiments, the compound of the invention is an antifouling agent capable of preventing or arresting adsorption of secretion products of cells of multi-cellular organism or of microorganisms to a surface dialysis units to prevent adherence of blood cells or of proteins secreted from blood cells from a patient being treated by the unit.

In some embodiments, the organisms are bacteria. In some embodiments, the bacteria being selected, in some embodiments from *Bordetella pertussis, Borrelia burgdorferi, Brucella abortus, Brucella canis, Brucella melitensis, Brucella suis, Campylobacter jejuni, Chlamydia pneumonia, Chlamydia psittaci, Chlamydia trachomatis, Clostridium botulinum, Clostridium difficile, Clostridium perfringens, Clostridium tetani, Corynebacterium diphtheria, Enterococcus faecalis, Enterococcus faecium, Escherichia coli (E. coli)*, Enterotoxigenic *Escherichia coli* (ETEC), Enteropathogenic *E. coli, Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumonia, Neisseria gonorrhoeae, Neisseria meningitidis, Pseudomonas aeruginosa, Rickettsia rickettsii, Salmonella typhi, Salmonella typhimurium, Shigella sonnei, Staphylococcus epidermidis, Staphylococcus saprophyticus, Streptococcus agalactiae, Streptococcus mutans Streptococcus pneumonia, Streptococcus pyogenes, Treponema pallidum, Vibrio cholera, Vibrio harveyi* and *Yersinia pestis*.

In some embodiments of the invention, the bacterium is *Escherichia coli (E. Coli)*. In some embodiments of the invention, the bacterium is *P. aeruginosa*.

As used herein, the term "prevention" refers to the arresting, limiting or overall controlling settling, attachment, accumulation and dispersion of organisms and/or organism's secretion and/or organic and/or bio-organic material (e.g., proteins and/or (poly)saccharides and/or (poly)lipids) on a surface, prevention of biofilm formation and to affecting its integrity (e.g., degrading it) and further growth. As a person of skill in the art would realize, the compounds and/or films of the invention have the ability to prevent and control fouling of a surface by minimizing, diminishing or arresting fouling adhesion, by foul release. Thus, the compounds and/or films of the invention may similarly be regarded as antimicrobial, antiviral, antifungal and cytostatic materials.

In another aspect of the invention, there is provided a method for inhibiting settling, attachment, accumulation and dispersion of organisms and/or organism's secretion and/or organic and/or bio-organic material (e.g., proteins and/or (poly)saccharides and/or (poly)lipids) on a surface, the method comprising contacting the surface with an effective amount of a formulation comprising a compound according to the invention (e.g., the peptide).

The invention provides a further method for inhibiting settling, attachment, accumulation and dispersion of organisms and/or organism's secretion and/or organic and/or bio-organic material (e.g., proteins and/or (poly)saccharides and/or (poly)lipids) on a surface, the method comprising forming a film or coat or layer of a compound according to the invention on said surface.

The invention further provides a kit comprising a compound according to the invention and at least one solvent for dissolving or formulating said compound into a deliverable form, and instructions of use.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 3A-3F show contact angle measurement of peptide 1 coated on a Ti surface in methanol (FIG. 3A), ethanol (FIG. 3B), isopropanol (FIG. 3C), acetone (FIG. D), dimethyl sulphoxide (DMSO) (FIG. 3E) and 1,1,1,3,3,3-hexafluoro-2-propanol (HFP) (FIG. 3F). Concentration used were 0.5 mg/mL, incubation time 10 h.

FIG. 4 provides ATR-FTIR spectrum of peptide 1, dissolved in acetone (lower line), ethanol (middle line) and isopropanol (top line).

FIGS. 5A-5H show contact angle measurements of a bare and coated surface with peptide 1, (FIG. 5A, FIG. 5B) titanium, (FIG. 5C, FIG. 5D) gold (FIG. 5E, FIG. 5F) silicon and (FIG. 5G, FIG. 5H) stainless steel. Peptide concentration was 0.5 mg/mL, dissolved in methanol, incubation time 10 h.

FIGS. 6A-6E show contact angle measurements of titanium surfaces coated with different peptides (FIG. 6A) peptide 2, (FIG. 6B) peptide 3, (FIG. 6C) peptide 4, (FIG. 6D) peptide 5 and (FIG. 6E) peptide 6. Peptide concentration was 0.5 mg/mL, dissolved in methanol, incubation time 10 h.

FIGS. 7A-7C show hydrophobicity enhancement as influenced by concentration of a peptide: Contact angle of (FIG. 7A) bare Ti surface (FIG. 7B) peptide 1 coated Ti surface at 0.5 mg/mL (FIG. 7C) peptide 1 coated Ti surface at 1.0 mg/mL. Incubation time 10 h, solvent methanol.

FIGS. 8A-8G present AFM topography images of (FIG. 8A) a bare mica, and a mica substrate modified with (FIG. 8B) peptide 1 (FIG. 8C) peptide 2 (FIG. 8D) peptide 3 (FIG. 8E) peptide 4 (FIG. 8F) peptide 5 and (FIG. 8G) peptide 6. The scale bar represents 500 nm.

FIGS. 9A-9B present Atomic Force Microscopic (AFM) images of (FIG. 9A) bare Ti surface and (FIG. 9B) Peptide 1 coated Ti surface.

FIG. 10 presents ATR-FTIR spectra of (a) a bare Ti surface and (b) a Ti surface coated with peptide 1.

FIGS. 18A-18D present micrographs of crystal violet stained *P. aeruginosa* biofilms on control Ti (FIG. A) and on peptide coated Ti (FIG. B). (FIG. C-D) show biofilm formation reduction by peptide coating.

FIG. 19A is a TEM image of a film self-assembled on a TEM cupper grid. FIG. 19B is a SEM image of a film formed on a silicon substrate.

DETAILED DESCRIPTION OF EMBODIMENTS

Figure 1:
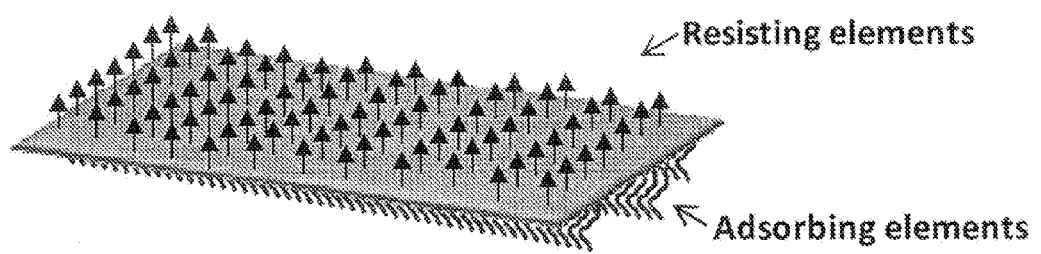
FIG. 1 depicts a configuration of a film according to the invention, the film comprising compounds or peptides according to the invention, wherein the adsorbing elements are at one side of the film and the elements that resist fouling (antifouling elements) are at the other side of the film.

Biofouling is a process in which organisms and their by-products encrust a surface. It is one of the main concerns today in the health care system as the adsorption of pathogenic bacteria to medical devices causes hospital acquired infections. In addition, it is a major problem in the marine industry since the adsorption of marine organisms on ships hull leads to an increase in the consumption of fuel and delays in transportation. Many approaches to prevent biofouling have been suggested, however, they suffer from drawbacks such as release of toxic materials to the surroundings, low stability that limits their long-term application or complex and expensive synthesis.

The invention disclosed herein is based on the inventors development of antifouling coatings that are spontaneously formed by the self-assembly of a compounds such as peptides. The results presented clearly show that the coatings completely prevented the first stage of biofouling and abolished the adsorption of proteins to a substrate. In addition, the coating reduced significantly the amount of bacteria on the substrate.

The invention provides a peptide comprising at least two amino acids, at least one of said amino acids being 3,4-dihydroxy-L-phenylalanin (DOPA) and at least another of said amino acids being fluorinated.

In some embodiments, said peptide is antifouling.

In some embodiments, said fluorinated amino acid is bonded to said at least one DOPA.

In some embodiments, the peptide comprising between 3 and 8 amino acids. In some embodiments, the peptide comprising between 2 and 8 amino acids, between 3 and 6 amino acids or between 3 and 5 amino acids.

In some embodiments, each amino acid is bonded to said another amino acid via a peptidic bond. In some embodiments, at least two of said amino acids are bonded to each other through a covalent linker. In some embodiments, the peptide of the invention having the general formula A-L-F, wherein A is DOPA, L is a covalent bond or a linker moiety linking A and F, and F is a fluorinated amino acid moiety.

In some embodiments, said bond or linker associating A to L, or L to F is a non-hydrolysable bond or linker group. In some embodiments, the linker is selected from substituted or unsubstituted carbon chain. In some embodiments, the linker is composed of two or more amino acids. In some embodiments, the linker comprises between 1 to 40 carbon atoms. In some embodiments, the linker is of the general structure

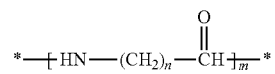

wherein
each * denotes a point of connectivity;
n is between 0 and 40; and
m is between 1 and 40.

In some embodiments, two or more moieties are DOPA moieties. In some embodiments, the peptide comprises two or more fluorinated amino acids. In some embodiments, the peptide comprises two or more DOPA and two or more fluorinated amino acids moieties.

In some embodiments, the peptide comprises one or more DOPA and two or more fluorinated amino acids moieties. In some embodiments, the peptide comprises two or more DOPA and one or more fluorinated amino acids moieties. In some embodiments, said amino acid being fluorinated is selected amongst natural or unnatural amino acid, an amino acid analog, α- or β-forms, and L- or D amino acids. In some embodiments, the amino acid is selected amongst alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine valine, pyrrolysine and selnocysteine; and amino acid analogs such as homo-amino acids, N-alkyl amino acids, dehydroamino acids, aromatic amino acids and α,α-disubstituted amino acids, cystine, 5-hydroxylysine, 4-hydroxyproline, a-aminoadipic acid, a-amino-n-butyric acid, 3,4-dihydroxyphenylalanine, homoserine, α-methylserine, ornithine, pipecolic acid, ortho, meta or para-aminobenzoic acid, citrulline, canavanine, norleucine, d-glutamic acid, aminobutyric acid, L-fluorenylalanine, L-3-benzothienylalanine and thyroxine.

In some embodiments, the amino acid is selected amongst aromatic amino acids. In some embodiments, the aromatic amino acids are selected from tryptophan, tyrosine, naphthylalanine, and phenylalanine. In some embodiments, the amino acids are selected from phenylalanine and/or derivatives thereof.

In some embodiments, the phenylalanine derivatives are selected from 4-methoxy-phenylalanine, 4-carbamimidoyl-1-phenylalanine, 4-chloro-phenylalanine, 3-cyano-phenylalanine, 4-bromo-phenylalanine, 4-cyano-phenylalanine, 4-hydroxymethyl-phenylalanine, 4-methyl-phenylalanine, 1-naphthyl-alanine, 3-(9-anthryl)-alanine, 3-methyl-phenylalanine, m-amidinophenyl-3-alanine, phenylserine, benzylcysteine, 4,4-biphenylalanine, 2-cyano-phenylalanine, 2,4-dichloro-phenylalanine, 3,4-dichloro-phenylalanine, 2-chloro-penylalanine, 3,4-dihydroxy-phenylalanine, 3,5-dibromotyrosine, 3,3-diphenylalanine, 3-ethyl-phenylalanine, 3,4-difluoro-phenylalanine, 3-chloro-phenylalanine, 3-chloro-phenylalanine, 2-fluoro-phenylalanine, 3-fluorophenylalanine, 4-amino-L-phenylalanine, homophenylalanine, 3-(8-hydroxyquinolin-3-yl)-1-alanine, 3-iodo-tyrosine, kynurenine, 3,4-dimethyl-phenylalanine, 2-methylphenylalanine, m-tyrosine, 2-naphthyl-alanine, 5-hydroxy-1-naphthalene, 6-hydroxy-2-naphthalene, meta-nitrotyrosine, (beta)-beta-hydroxy-1-tyrosine, (beta)-3-chloro-beta-hydroxy-1-tyrosine, o-tyrosine, 4-benzoyl-phenylalanine, 3-(2-pyridyl)-alanine, 3-(3-pyridyl)-alanine, 3-(4-pyridyl)-alanine, 3-(2-quinolyl)-alanine, 3-(3-quinolyl)-alanine, 3-(4-quinolyl)-alanine, 3-(5-quinolyl)-alanine, 3-(6-quinolyl)-alanine, 3-(2-quinoxalyl)-alanine, styrylalanine, pentafluoro-phenylalanine, 4-fluoro-phenylalanine, phenylalanine, 4-iodo-phenylalanine, 4-nitro-phenylalanine, phosphotyrosine, 4-tert-butyl-phenylalanine, 2-(trifluoromethyl)-phenylalanine, 3-(trifluoromethyl)-phenylalanine, 4-(trifluoromethyl)-phenylalanine, 3-amino-L-tyrosine, 3,5-diiodotyrosine, 3-amino-6-hydroxy-tyrosine, tyrosine, 3,5-difluoro-phenylalanine and 3-fluorotyrosine.

In some embodiments, said fluorinated amino acid are selected from o-fluorophenylalanine, m-fluorophenylalanine and p-fluorophenylalanine.

In some embodiments, the peptide comprises between 2 and 12 amino acids, each amino acid being selected from aromatic amino acids. In some embodiments, the peptide comprises DOPA at one termini and a fluorinated aromatic amino acid selected from o-fluorophenylalanine, m-fluorophenylalanine and p-fluorophenylalanine at the other termini. In some embodiments, the peptide comprises DOPA at a mid-point amino acid along the peptide and a fluorinated aromatic amino acid selected from o-fluorophenylalanine, m-fluorophenylalanine and p-fluorophenylalanine at each of the peptide termini.

In some embodiments, the peptide is for use as an antifouling agent; e.g., for preventing or arresting or minimizing or diminishing one or more of the following:

(a) adsorption of organic and/or bio-organic materials to a surface;

(b) adsorption of proteins and/or (poly)saccharides and (poly)lipids to a surface;

(c) secretion from cells of multi-organism or of micro-organisms onto a surface; and (d) adsorption of cells of multi-organism or micro-organisms to a surface.

The specific compounds of the invention are selected from:

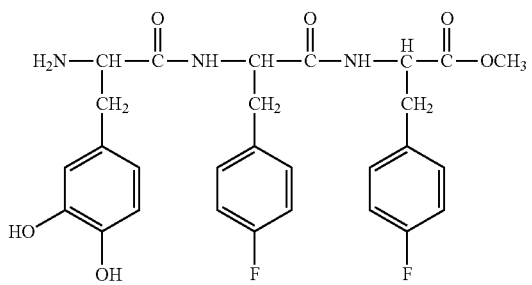

-continued

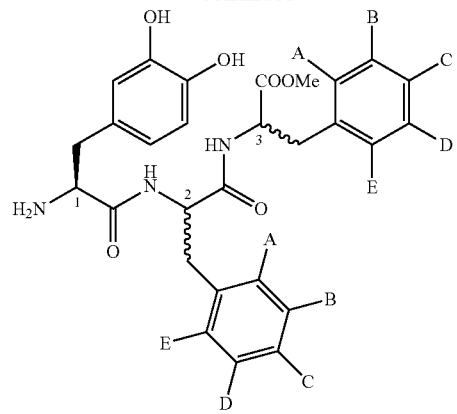

Peptide 1: (1S, 2S, 3S) A = B = D = E = —H, C = —F
Peptide 2: (1S, 2S, 3R) A = B = D = E = —H, C = —F
Peptide 3: (1S, 2R, 3S) A = B = D = E = —H, C = —F
Peptide 4: (1S, 2R, 3R) A = B = D = E = —H, C = —F
Peptide 5: (1S, 2S, 3S) A = B = C = D = E = —F

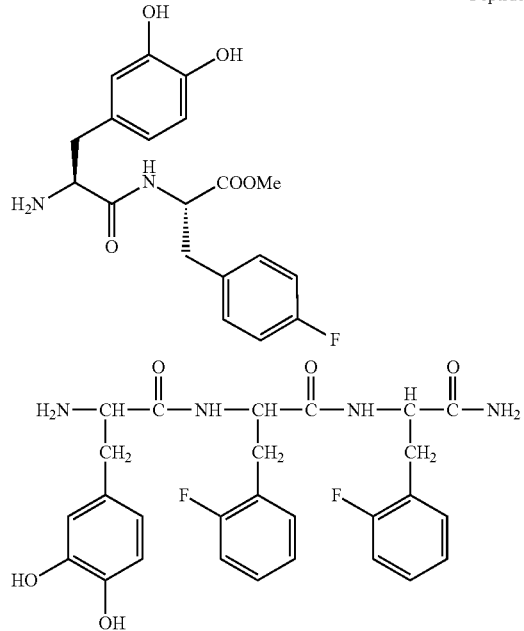

Peptide 6

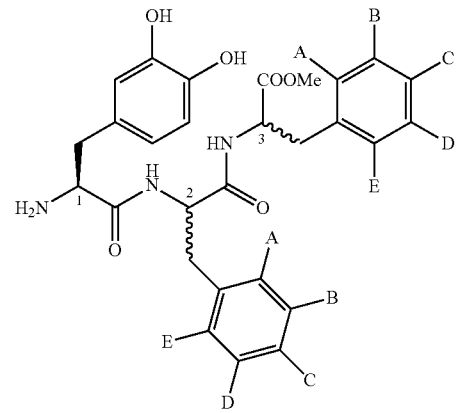

Peptide 7: (1S, 2S, 3S) A = B = C = D = —H, E = —F
Peptide 8: (1S, 2S, 3R) A = B = C = D = —H, E = —F
Peptide 9: (1S, 2R, 3S) A = B = C = D = —H, E = —F
Peptide 10: (1S, 2S, 3R) A = B = C = D = —H, E = —F.

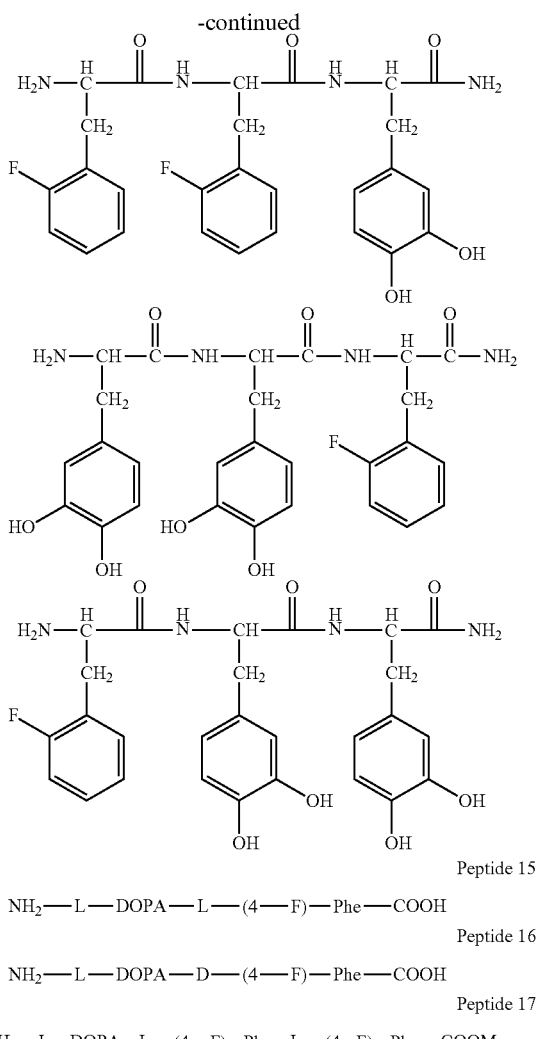

NH$_2$—L—DOPA—L—(4—F)—Phe—COOH

Peptide 15

NH$_2$—L—DOPA—D—(4—F)—Phe—COOH

Peptide 16

NH$_2$—L—DOPA—L—(4—F)—Phe—L—(4—F)—Phe—COOMe.

Peptide 17

The invention also contemplates formulations comprising peptide compounds as described herein. The formulation may be a ready-for-use antifouling formulation.

The invention also provides a film or a coat comprising at least one peptide of the invention. The film is preferably antifouling and/or anti-biofilm.

The film may be part of an article or a device comprising at least one surface region coated with a film according to the invention. The article or device may be selected from a marine vessel, a hull of a marine vessel, a medical device, a contact lens, a food processing apparatus, a drinking water dispensing apparatus, a pipeline, a cable, a fishing net, a pillar of a bridge and a surface region of a water immersed article.

The film in such devices or articles are for preventing biofouling caused by an organism selected from bacteria, diatoms, hydroids, algae, bryozoans, protozoans, ascidians, tube worms, asiatic clams, zebra mussels and barnacles. In some embodiments, the organisms are bacteria. In some embodiments, the bacteria is selected from *Bordetella pertussis, Borrelia burgdorferi, Brucella abortus, Brucella canis, Brucella melitensis, Brucella suis, Campylobacter jejuni, Chlamydia pneumonia, Chlamydia psittaci, Chlamydia trachomatis, Clostridium botulinum, Clostridium difficile, Clostridium perfringens, Clostridium tetani, Corynebacterium diphtheria, Enterococcus faecalis, Enterococcus faecium, Escherichia coli (E. coli)*, Enterotoxigenic *Escherichia coli* (ETEC), Enteropathogenic *E. coli, Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumonia, Neisseria gonorrhoeae, Neisseria meningitidis, Pseudomonas aeruginosa, Rickettsia rickettsii, Salmonella typhi, Salmonella typhimurium, Shigella sonnei, Staphylococcus epidermidis, Staphylococcus saprophyticus, Streptococcus agalactiae, Streptococcus mutans Streptococcus pneumonia, Streptococcus pyogenes, Treponema pallidum, Vibrio cholera, Vibrio harveyi* and *Yersinia pestis*.

In some embodiments, bacteria are *Escherichia coli (E. Coli)*. In some embodiments, the bacteria are *P. aeruginosa*.

The invention also provide use of a peptide according the invention for preventing or arresting adsorption of secretion products of cells of multi-cellular organism or of microorganisms to a surface of a dialysis unit to prevent adherence of blood cells or of proteins secreted from blood cells from a patient being treated by the unit.

The invention further provides a method for inhibiting settling, attachment, accumulation and dispersion of organisms, organism's secretion of an organic and/or bio-organic material on a surface, the method comprising contacting the surface with an effective amount of a formulation comprising a peptide according to the invention.

In another aspect, the invention provides a film or a coat comprising a compound having at least one antifouling moiety and at least one surface-adsorbing moiety, wherein the at least one antifouling moiety is selected amongst fluorine (—F) and a group comprising at least one fluorine atom and said at least one surface-adsorbing moiety being selected amongst 3,4-dihydroxy-L-phenylalanin (DOPA) and DOPA containing groups. In some embodiments, the film or coat is formed on a surface region of a device or an article.

The invention also provides a film or a coat comprising a bifunctional compound comprising at least one antifouling moiety and at least one surface-adsorbing moiety (or group), wherein the at least one antifouling moiety is selected amongst fluorine (—F) and at least one group comprising a fluorine atom and said at least one surface-adsorbing moiety being selected amongst dihydroxy-amino acids and dihydroxy-amino acid containing groups, said at least one antifouling moiety and said at least one surface-adsorbing moiety being associated to each other via a covalent bond or via a linker moiety. The film or coat may comprise at least one antifouling moiety and at least one surface-adsorbing moiety, wherein the at least one antifouling moiety being selected amongst fluorine (—F) and at least one group comprising a fluorine atom and said at least one surface-adsorbing moiety is selected amongst 3,4-dihydroxy-L-phenylalanin (DOPA) and DOPA containing groups, and wherein said at least one antifouling moiety and said at least one surface-adsorbing moiety being associated to each other via a covalent bond or via a linker moiety.

In some embodiments, said compound being of the general formula A-L-F, wherein A is a surface-adsorbing moiety, L is a covalent bond or a linker moiety linking A and F, and F is an antifouling moiety, and wherein each of A, L and F are associated to each other via a non-hydrolysable bond.

The film or coat is antifouling for preventing or arresting adsorption of organic and/or bio-organic materials to said surface, or for preventing or arresting adsorption of secretion products of cells of multi-cellular organisms or of microorganisms to a surface.

In some embodiments, the surface-adsorbing moiety is DOPA being linked, associated or bonded to an atom on said linker moiety. In some embodiments, said linker moiety is a one-carbon chain. In some embodiments, the linker moiety is selected from substituted or unsubstituted carbon chain. In some embodiments, the linker moiety is selected from amino acids and peptides. In some embodiments, the linker moiety comprises between 1 to 40 carbon atoms. In some embodiments, the linker moiety is substituted by one or more functional groups selected from substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heterocyclyl, substituted or unsubstituted —$NR_1R_2$, substituted or unsubstituted —$OR_3$, substituted or unsubstituted —$SR_4$, substituted or unsubstituted —$S(O)R_5$, substituted or unsubstituted alkylene-COOH, and substituted or unsubstituted ester.

In some embodiments, the linker moiety is of the general structure

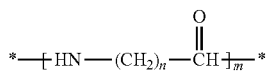

wherein
each * denotes a point of connectivity;
n is between 0 and 40; and
m is between 1 and 40.

In some embodiments, n is between 1 and 12. In some embodiments, n is between 1 and 8. In some embodiments, n is between 1 and 6. In some embodiments, m is between 1 and 20. In some embodiments, m is between 1 and 12. In some embodiments, m is between 1 and 8. In some embodiments, m is between 1 and 6.

In some embodiments, one or more of the $(CH_2)_n$ groups are substituted.

In some embodiments, the linker moiety is an amino acid comprising 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 amino acids.

In some embodiments, the compound is constructed of two amino acids bonded to each other via an amide bond, wherein one amino acid is DOPA and the other being a fluorinated amino acid. In some embodiments, the antifouling moieties are bonded to the linker at one end and the surface-adsorbing moieties at the other end of the linker moiety. In some embodiments, the antifouling moieties and the surface-adsorbing moieties are at alternating positions along the linker moiety.

In some embodiments, the linker moiety comprises or consists a peptide of two or more amino acids.

In some embodiments, the compound is a peptide having at least two amino acids, at least one DOPA and at least fluorinated group, which may or may not be a fluorinated amino acid. In some embodiments, the peptide comprises between 2 and 40 amino acids. In some embodiments, the peptide comprises 2, or 3, or 4, or 5, or 6, or 7, or 8 or 9 or 10 or 11 or 12 amino acids.

In some embodiments, said antifouling moiety is a fluorinated amino acid selected amongst natural or unnatural amino acid, an amino acid analog, α- or β-forms, and L- or D amino acids. In some embodiments, the amino acid is selected amongst alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine valine, pyrrolysine and selnocysteine; and amino acid analogs such as homoamino acids, N-alkyl amino acids, dehydroamino acids, aromatic amino acids and α,α-disubstituted amino acids, cystine, 5-hydroxylysine, 4-hydroxyproline, a-aminoadipic acid, a-amino-n-butyric acid, 3,4-dihydroxyphenylalanine, homoserine, α-methylserine, ornithine, pipecolic acid, ortho, meta or para-aminobenzoic acid, citrulline, canavanine, norleucine, d-glutamic acid, aminobutyric acid, L-fluorenylalanine, L-3-benzothienylalanine and thyroxine.

In some embodiments, the amino acid is selected amongst aromatic amino acids. In some embodiments, said aromatic amino acids are selected from tryptophan, tyrosine, naphthylalanine, and phenylalanine.

In some embodiments, the amino acids are selected from phenylalanine and derivatives thereof. In some embodiments, the phenylalanine derivatives are selected from 4-methoxy-phenylalanine, 4-carbamimidoyl-1-phenylalanine, 4-chloro-phenylalanine, 3-cyano-phenylalanine, 4-bromo-phenylalanine, 4-cyano-phenylalanine, 4-hydroxymethyl-phenylalanine, 4-methyl-phenylalanine, 1-naphthyl-alanine, 3-(9-anthryl)-alanine, 3-methyl-phenylalanine, m-amidinophenyl-3-alanine, phenylserine, benzylcysteine, 4,4-biphenylalanine, 2-cyano-phenylalanine, 2,4-dichloro-phenylalanine, 3,4-dichloro-phenylalanine, 2-chloro-penylalanine, 3,4-dihydroxy-phenylalanine, 3,5-dibromotyrosine, 3,3-diphenylalanine, 3-ethyl-phenylalanine, 3,4-difluoro-phenylalanine, 3-chloro-phenylalanine, 3-chloro-phenylalanine, 2-fluoro-phenylalanine, 3-fluorophenylalanine, 4-amino-L-phenylalanine, homophenylalanine, 3-(8-hydroxyquinolin-3-yl)-1-alanine, 3-iodo-tyrosine, kynurenine, 3,4-dimethyl-phenylalanine, 2-methylphenylalanine, m-tyrosine, 2-naphthyl-alanine, 5-hydroxy-1-naphthalene, 6-hydroxy-2-naphthalene, meta-nitrotyrosine, (beta)-beta-hydroxy-1-tyrosine, (beta)-3-chlorobeta-hydroxy-1-tyrosine, o-tyrosine, 4-benzoyl-phenylalanine, 3-(2-pyridyl)-alanine, 3-(3-pyridyl)-alanine, 3-(4-pyridyl)-alanine, 3-(2-quinolyl)-alanine, 3-(3-quinolyl)-alanine, 3-(4-quinolyl)-alanine, 3-(5-quinolyl)-alanine, 3-(6-quinolyl)-alanine, 3-(2-quinoxalyl)-alanine, styrylalanine, pentafluoro-phenylalanine, 4-fluoro-phenylalanine, phenylalanine, 4-iodo-phenylalanine, 4-nitro-phenylalanine, phosphotyrosine, 4-tert-butyl-phenylalanine, 2-(trifluoromethyl)-phenylalanine, 3-(trifluoromethyl)-phenylalanine, 4-(trifluoromethyl)-phenylalanine, 3-amino-L-tyrosine, 3,5-diiodotyrosine, 3-amino-6-hydroxy-tyrosine, tyrosine, 3,5-difluoro-phenylalanine and 3-fluorotyrosine.

In some embodiments, said fluorinated amino acid are selected from o-fluorophenylalanine, m-fluorophenylalanine and p-fluorophenylalanine.

In some embodiments, the compound comprising DOPA at one termini and a fluorinated aromatic amino acid selected from o-fluorophenylalanine, m-fluorophenylalanine and p-fluorophenylalanine at the other termini.

In some embodiments, the compound comprising DOPA at a mid-point amino acid along the peptide and a fluorinated aromatic amino acid selected from o-fluorophenylalanine, m-fluorophenylalanine and p-fluorophenylalanine at each of the peptide termini.

In some embodiments, the film or coat is provided for preventing or arresting or minimizing or diminishing one or more of the following:

(b) adsorption of organic and/or bio-organic materials to a surface;

(b) adsorption of proteins and/or (poly)saccharides and (poly)lipids to a surface;

(c) secretion from cells of multi-organism or of micro-organisms onto a surface; and (d) adsorption of cells of multi-organism or micro-organisms to a surface.

In some embodiments, the compound has the structure:

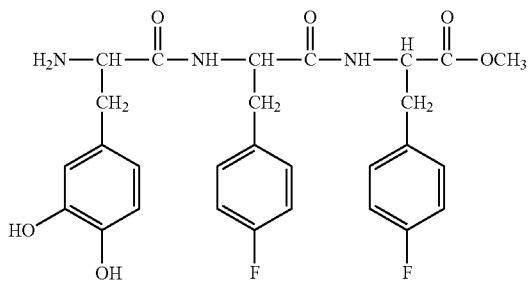

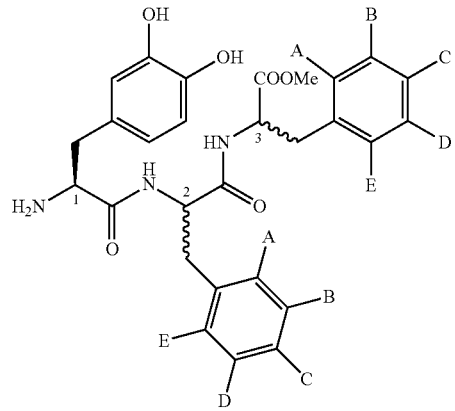

Peptide 1: (1S, 2S, 3S) A = B = D = E = ——H, C = ——F
Peptide 2: (1S, 2S, 3R) A = B = D = E = ——H, C = ——F
Peptide 3: (1S, 2R, 3S) A = B = D = E = ——H, C = ——F
Peptide 4: (1S, 2R, 3R) A = B = D = E = ——H, C = ——F
Peptide 5: (1S, 2S, 3S) A = B = C = D = E = ——F Peptide 6

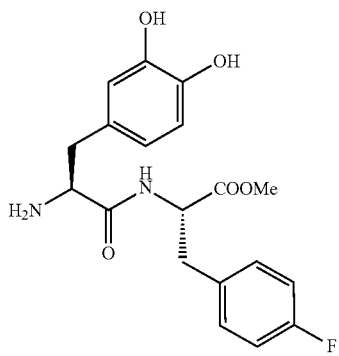

-continued

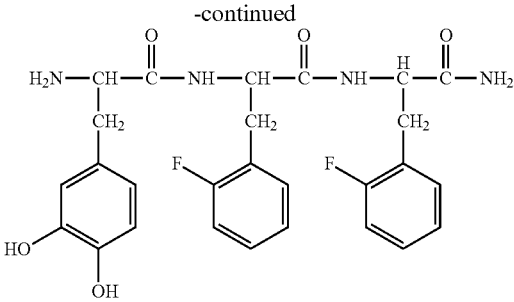

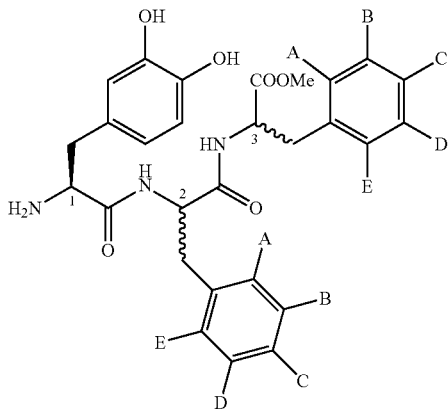

Peptide 7: (1S, 2S, 3S) A = B = C = D = ——H, E = ——F
Peptide 8: (1S, 2S, 3R) A = B = C = D = ——H, E = ——F
Peptide 9: (1S, 2R, 3S) A = B = C = D = ——H, E = ——F
Peptide 10: (1S, 2S, 3R) A = B = C = D = ——H, E = ——F.

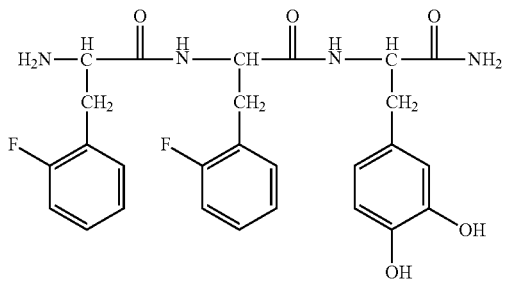

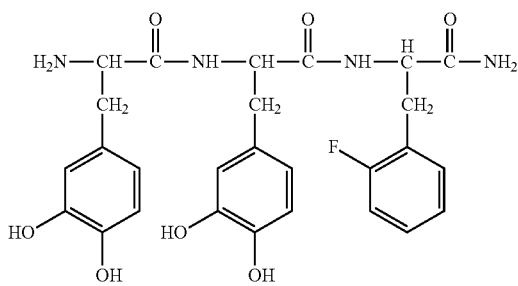

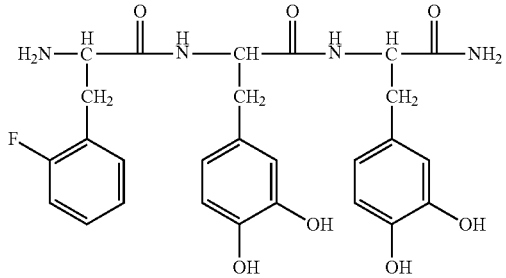

In some embodiments, the compound is selected from

NH$_2$-L-DOPA-L-(4-F)-Phe-COOH    Peptide 15

NH$_2$-L-DOPA-D-(4-F)-Phe-COOH    Peptide 16

NH$_2$-L-DOPA-L-(4-F)-Phe-L-(4-F)-Phe-COOMe    Peptide 17.

The invention also provides an article or a device comprising at least one surface region coated with a film or coat according to the invention. In some embodiments, the article or device is selected from a marine vessel, a hull of a marine vessel, a medical device, a contact lens, a food processing apparatus, a drinking water dispensing apparatus, a pipeline, a cable, a fishing net, a pillar of a bridge and a surface region of a water immersed article.

In some embodiments, the film or coat is provided for preventing biofouling caused by an organism selected from bacteria, diatoms, hydroids, algae, bryozoans, protozoans, ascidians, tube worms, asiatic clams, zebra mussels and barnacles.

In some embodiments, the organisms are bacteria. In some embodiments, the bacteria are selected from *Bordetella pertussis, Borrelia burgdorferi, Brucella abortus, Brucella canis, Brucella melitensis, Brucella suis, Campylobacter jejuni, Chlamydia pneumonia, Chlamydia psittaci, Chlamydia trachomatis, Clostridium botulinum, Clostridium difficile, Clostridium perfringens, Clostridium tetani, Corynebacterium diphtheria, Enterococcus faecalis, Enterococcus faecium, Escherichia coli* (*E. coli*), Enterotoxigenic *Escherichia coli* (ETEC), Enteropathogenic *E. coli, Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumonia, Neisseria gonorrhoeae, Neisseria meningitidis, Pseudomonas aeruginosa, Rickettsia rickettsii, Salmonella typhi, Salmonella typhimurium, Shigella sonnei, Staphylococcus epidermidis, Staphylococcus saprophyticus, Streptococcus agalactiae, Streptococcus mutans Streptococcus pneumonia, Streptococcus pyogenes, Treponema pallidum, Vibrio cholera, Vibrio harveyi* and *Yersinia pestis*.

In some embodiments, the bacteria are *Escherichia coli* (E. Coli). In some embodiments, the bacteria are *P. aeruginosa*.

The invention also provides a composition comprising a compound having at least one antifouling moiety and at least one surface-adsorbing moiety, wherein the at least one antifouling moiety is selected amongst fluorine (—F) and a group comprising at least one fluorine atom and said at least one surface-adsorbing moiety being selected amongst 3,4-dihydroxy-L-phenylalanin (DOPA) and DOPA containing groups, for use in forming a self-assembled antifouling film or coat on a surface region of a device or an article.

The invention also a composition comprising a bifunctional compound comprising at least one antifouling moiety and at least one surface-adsorbing moiety (or group), wherein the at least one antifouling moiety is selected amongst fluorine (—F) and at least one group comprising a fluorine atom and said at least one surface-adsorbing moiety being selected amongst dihydroxy-amino acids and dihydroxy-amino acid containing groups, said at least one antifouling moiety and said at least one surface-adsorbing moiety being associated to each other via a covalent bond or via a linker moiety.

In some embodiments, the composition comprises at least one antifouling moiety and at least one surface-adsorbing moiety, wherein the at least one antifouling moiety being selected amongst fluorine (—F) and at least one group comprising a fluorine atom and said at least one surface-adsorbing moiety is selected amongst 3,4-dihydroxy-L-phenylalanin (DOPA) and DOPA containing groups, and wherein said at least one antifouling moiety and said at least one surface-adsorbing moiety being associated to each other via a covalent bond or via a linker moiety.

In some embodiments, the compound is of the general formula A-L-F, wherein A is a surface-adsorbing moiety, L is a covalent bond or a linker moiety linking A and F, and F is an antifouling moiety, and wherein each of A, L and F are associated to each other via a non-hydrolysable bond.

The composition is antifouling for preventing or arresting adsorption of organic and/or bio-organic materials to said surface, or for preventing or arresting adsorption of secretion products of cells of multi-cellular organisms or of microorganisms to a surface.

In some embodiments, the surface-adsorbing moiety is DOPA being linked, associated or bonded to an atom on said linker moiety. In some embodiments, said linker moiety is a one-carbon chain. In some embodiments, the linker moiety is selected from substituted or unsubstituted carbon chain. In some embodiments, the linker moiety is selected from amino acids and peptides. In some embodiments, the linker moiety comprises between 1 to 40 carbon atoms. In some embodiments, the linker moiety is substituted by one or more functional groups selected from substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted aryl, substituted or unsubstituted heteroaryl, substituted or unsubstituted heterocyclyl, substituted or unsubstituted —NR$_1$R$_2$, substituted or unsubstituted —OR$_3$, substituted or unsubstituted —SR$_4$, substituted or unsubstituted —S(O)R$_5$, substituted or unsubstituted alkylene-COOH, and substituted or unsubstituted ester.

In some embodiments, the linker moiety is of the general structure

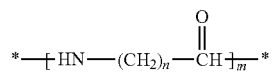

wherein each * denotes a point of connectivity;

n is between 0 and 40; and m is between 1 and 40.

In some embodiments, n is between 1 and 12. In some embodiments, n is between 1 and 8. In some embodiments, n is between 1 and 6. In some embodiments, m is between 1 and 20. In some embodiments, m is between 1 and 12. In some embodiments, m is between 1 and 8. In some embodiments, m is between 1 and 6.

In some embodiments, one or more of the (CH$_2$)$_n$ groups are substituted.

In some embodiments, the linker moiety is an amino acid comprising 2 or 3 or 4 or 5 or 6 or 7 or 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 amino acids.

In some embodiments, the compound is constructed of two amino acids bonded to each other via an amide bond, wherein one amino acid is DOPA and the other being a fluorinated amino acid. In some embodiments, the antifouling moieties are bonded to the linker at one end and the surface-adsorbing moieties at the other end of the linker moiety. In some embodiments, the antifouling moieties and the surface-adsorbing moieties are at alternating positions along the linker moiety.

In some embodiments, the linker moiety comprises or consists a peptide of two or more amino acids.

In some embodiments, the compound is a peptide having at least two amino acids, at least one DOPA and at least fluorinated group, which may or may not be a fluorinated amino acid. In some embodiments, the peptide comprises between 2 and 40 amino acids. In some embodiments, the peptide comprises 2, or 3, or 4, or 5, or 6, or 7, or 8 or 9 or 10 or 11 or 12 amino acids.

In some embodiments, said antifouling moiety is a fluorinated amino acid selected amongst natural or unnatural amino acid, an amino acid analog, α- or β-forms, and L- or D amino acids. In some embodiments, the amino acid is selected amongst alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine valine, pyrrolysine and selnocysteine; and amino acid analogs such as homoamino acids, N-alkyl amino acids, dehydroamino acids, aromatic amino acids and α,α-disubstituted amino acids, cystine, 5-hydroxylysine, 4-hydroxyproline, a-aminoadipic acid, a-amino-n-butyric acid, 3,4-dihydroxyphenylalanine, homoserine, α-methylserine, ornithine, pipecolic acid, ortho, meta or para-aminobenzoic acid, citrulline, canavanine, norleucine, d-glutamic acid, aminobutyric acid, L-fluorenylalanine, L-3-benzothienylalanine and thyroxine.

In some embodiments, the amino acid is selected amongst aromatic amino acids. In some embodiments, said aromatic amino acids are selected from tryptophan, tyrosine, naphthylalanine, and phenylalanine.

In some embodiments, the amino acids are selected from phenylalanine and derivatives thereof. In some embodiments, the phenylalanine derivatives are selected from 4-methoxy-phenylalanine, 4-carbamimidoyl-1-phenylalanine, 4-chloro-phenylalanine, 3-cyano-phenylalanine, 4-bromo-phenylalanine, 4-cyano-phenylalanine, 4-hydroxymethyl-phenylalanine, 4-methyl-phenylalanine, 1-naphthyl-alanine, 3-(9-anthryl)-alanine, 3-methyl-phenylalanine, m-amidinophenyl-3-alanine, phenylserine, benzylcysteine, 4,4-biphenylalanine, 2-cyano-phenylalanine, 2,4-dichloro-phenylalanine, 3,4-dichloro-phenylalanine, 2-chloro-penylalanine, 3,4-dihydroxy-phenylalanine, 3,5-dibromotyrosine, 3,3-diphenylalanine, 3-ethyl-phenylalanine, 3,4-difluoro-phenylalanine, 3-chloro-phenylalanine, 3-chloro-phenylalanine, 2-fluoro-phenylalanine, 3-fluorophenylalanine, 4-amino-L-phenylalanine, homophenylalanine, 3-(8-hydroxyquinolin-3-yl)-1-alanine, 3-iodo-tyrosine, kynurenine, 3,4-dimethyl-phenylalanine, 2-methylphenylalanine, m-tyrosine, 2-naphthyl-alanine, 5-hydroxy-1-naphthalene, 6-hydroxy-2-naphthalene, meta-nitrotyrosine, (beta)-beta-hydroxy-1-tyrosine, (beta)-3-chloro-beta-hydroxy-1-tyrosine, o-tyrosine, 4-benzoylphenylalanine, 3-(2-pyridyl)-alanine, 3-(3-pyridyl)-alanine, 3-(4-pyridyl)-alanine, 3-(2-quinolyl)-alanine, 3-(3-quinolyl)-alanine, 3-(4-quinolyl)-alanine, 3-(5-quinolyl)-alanine, 3-(6-quinolyl)-alanine, 3-(2-quinoxalyl)-alanine, styrylalanine, pentafluoro-phenylalanine, 4-fluoro-phenylalanine, phenylalanine, 4-iodo-phenylalanine, 4-nitro-phenylalanine, phosphotyrosine, 4-tert-butyl-phenylalanine, 2-(trifluoromethyl)-phenylalanine, 3-(tfifluoromethyl)-phenylalanine, 4-(trifluoromethyl)-phenylalanine, 3-amino-L-tyrosine, 3,5-diiodotyrosine, 3-amino-6-hydroxy-tyrosine, tyrosine, 3,5-difluoro-phenylalanine and 3-fluorotyrosine.

In some embodiments, said fluorinated amino acid are selected from o-fluorophenylalanine, m-fluorophenylalanine and p-fluorophenylalanine.

In some embodiments, the compound comprising DOPA at one termini and a fluorinated aromatic amino acid selected from o-fluorophenylalanine, m-fluorophenylalanine and p-fluorophenylalanine at the other termini.

In some embodiments, the compound comprising DOPA at a mid-point amino acid along the peptide and a fluorinated aromatic amino acid selected from o-fluorophenylalanine, m-fluorophenylalanine and p-fluorophenylalanine at each of the peptide termini.

In some embodiments, the film or coat is provided for preventing or arresting or minimizing or diminishing one or more of the following:

(c) adsorption of organic and/or bio-organic materials to a surface;

(b) adsorption of proteins and/or (poly)saccharides and (poly)lipids to a surface;

(c) secretion from cells of multi-organism or of microorganisms onto a surface; and (d) adsorption of cells of multi-organism or micro-organisms to a surface.

In some embodiments, the compound has the structure:

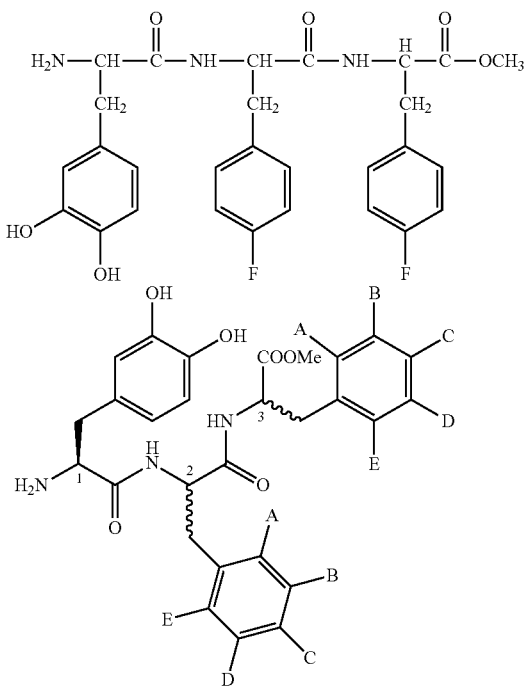

Peptide 1: (1S, 2S, 3S) A = B = D = E = ——H, C = ——F
Peptide 2: (1S, 2S, 3R) A = B = D = E = ——H, C = ——F
Peptide 3: (1S, 2R, 3S) A = B = D = E = ——H, C = ——F
Peptide 4: (1S, 2R, 3R) A = B = D = E = ——H, C = ——F
Peptide 5: (1S, 2S, 3S) A = B = C = D = E = ——F

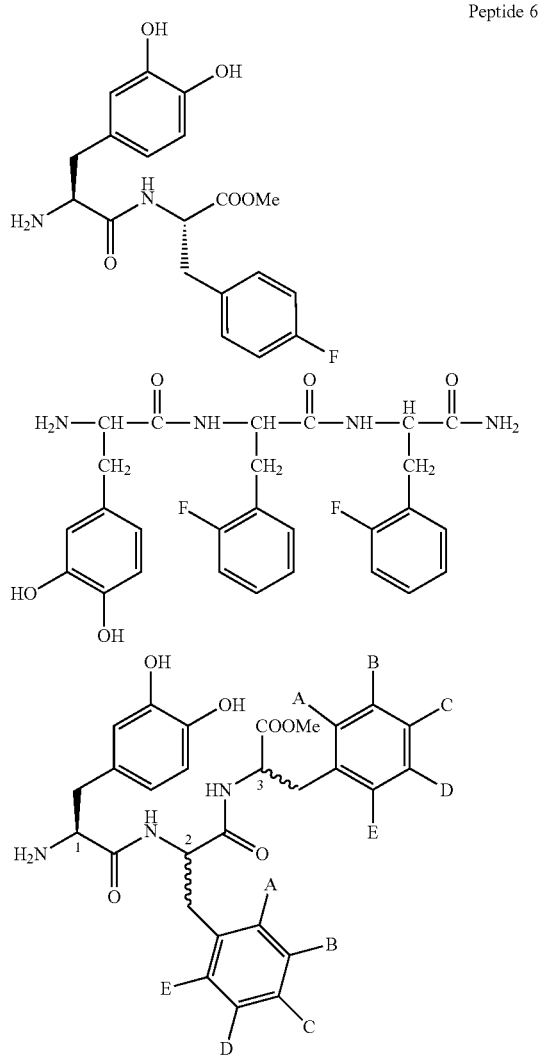

Peptide 7: (1S, 2S, 3S) A = B = C = D = —H, E = —F
Peptide 8: (1S, 2S, 3R) A = B = C = D = —H, E = —F
Peptide 9: (1S, 2R, 3S) A = B = C = D = —H, E = —F
Peptide 10: (1S, 2S, 3R) A = B = C = D = —H, E = —F.

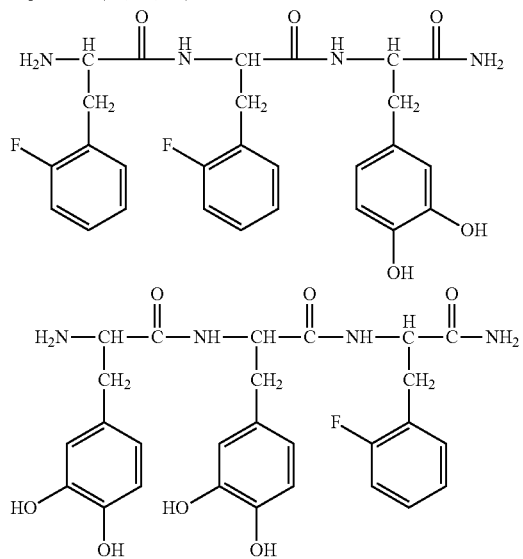

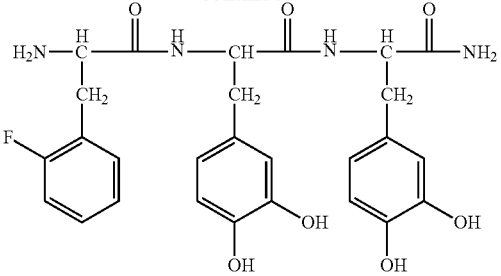

Peptide 6

In some embodiments, the compound is selected from

| | |
|---|---|
| NH$_2$-L-DOPA-L-(4-F)-Phe-COOH | Peptide 15 |
| NH$_2$-L-DOPA-D-(4-F)-Phe-COOH | Peptide 16 |
| NH$_2$-L-DOPA-L-(4-F)-Phe-L-(4-F)-Phe-COOMe | Peptide 17. |

In some embodiments, the composition is provided for preventing biofouling caused by an organism selected from bacteria, diatoms, hydroids, algae, bryozoans, protozoans, ascidians, tube worms, asiatic clams, zebra mussels and barnacles.

In some embodiments, the organisms are bacteria. In some embodiments, the bacteria are selected from *Bordetella pertussis, Borrelia burgdorferi, Brucella abortus, Brucella canis, Brucella melitensis, Brucella suis, Campylobacter jejuni, Chlamydia pneumonia, Chlamydia psittaci, Chlamydia trachomatis, Clostridium botulinum, Clostridium difficile, Clostridium perfringens, Clostridium tetani, Corynebacterium diphtheria, Enterococcus faecalis, Enterococcus faecium, Escherichia coli (E. coli),* Enterotoxigenic *Escherichia coli* (ETEC), Enteropathogenic *E. coli, Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumonia, Neisseria gonorrhoeae, Neisseria meningitidis, Pseudomonas aeruginosa, Rickettsia rickettsii, Salmonella typhi, Salmonella typhimurium, Shigella sonnei, Staphylococcus epidermidis, Staphylococcus saprophyticus, Streptococcus agalactiae, Streptococcus mutans Streptococcus pneumonia, Streptococcus pyogenes, Treponema pallidum, Vibrio cholera, Vibrio harveyi* and *Yersinia pestis.*

In some embodiments, the bacteria are *Escherichia coli* (*E. Coli*). In some embodiments, the bacteria are *P. aeruginosa.*

The invention further provides an antifouling formulation comprising a composition according to the invention. Also provided is an antimicrobial formulation comprising a composition of the invention. Further provided is an antibacterial formulation comprising a composition of the invention.

The invention further provides a kit comprising a composition according to the invention and instructions of use.

The invention also provides the use of a composition according to the invention for making an antifouling formulation or antimicrobial formulation or antibacterial formulation.

The invention also provides a method for forming a film or a coat of a plurality of compounds on a surface region, the compounds each comprising at least one antifouling moiety and at least one surface-adsorbing moiety, wherein the at least one antifouling moiety is selected amongst fluorine (—F) and a group comprising at least one fluorine atom and said at least one surface-adsorbing moiety being selected amongst 3,4-dihydroxy-L-phenylalanin (DOPA) and DOPA containing groups, the method comprising contacting said surface region with said compounds and permitting self assembly thereof on said surface region.

In some embodiments, said surface region is of a device or article. In some embodiments, the compound is provided as a formulation. In some embodiments, said film or coat having a property selected from antifouling, antimicrobial and antibacterial.

Materials and Methods

All chemicals, solvents, proteins and bacteria were purchased from commercially available companies and used as supplied unless otherwise stated. Fmoc-DOPA(ac)-COOH was obtained from Novabiochem/EMD chemicals (San-Diego, USA). L and D-4-fluoro phenylalanine, Boc-penta Fluoro phe-COOH were purchased from chem-impex Inc. (Wood Dale, USA). Solvents and TFA were purchased from Bio-lab (Jerusalem, Israel). NMR solvents (CDCl$_3$ and DMSO-d$_6$) were supplied by Sigma-Aldrich (Jerusalem, Israel). Piperidine used for deprotection of Fmoc group was obtained from Alfa-Aesar (UK). The proteins BSA, fibrinogen and lysozyme were obtained from Sigma-Aldrich (Jerusalem, Israel), Chem impex INC. (Wood Dale, USA) and Merck (Darmstadt, Germany) respectively. *Pseudomonas aeruginosa* (ATCC 27853) and *Eschrichia coli* (ATCC 1655) were purchased from ATCC (Virginia, USA). Crystal violet was obtained from Merck (Germany).

Peptide Synthesis

NMR spectra were obtained at 400.13 MHz ($^1$H) using a Bruker DRX 400 spectrometer. The mass of the peptides was measured using Applied Biosystem Voyager-DE pro MALDI TOF mass spectrometer. The peptides were synthesized by a conventional solution-phase method using a racemization free strategy. The Boc group and Fmoc group were used for N-terminal protection and the C-terminus was protected as a methyl ester. Couplings were mediated by dicyclohexylcarbodiimide/1-hydroxybenzotriazole (DCC/HOBt). The intermediate compounds were characterized by $^1$H NMR and MALDI-TOF mass spectroscopy and final peptides were fully characterized by $^1$H NMR, $^{13}$C NMR, $^{19}$F NMR, MALDI-TOF.

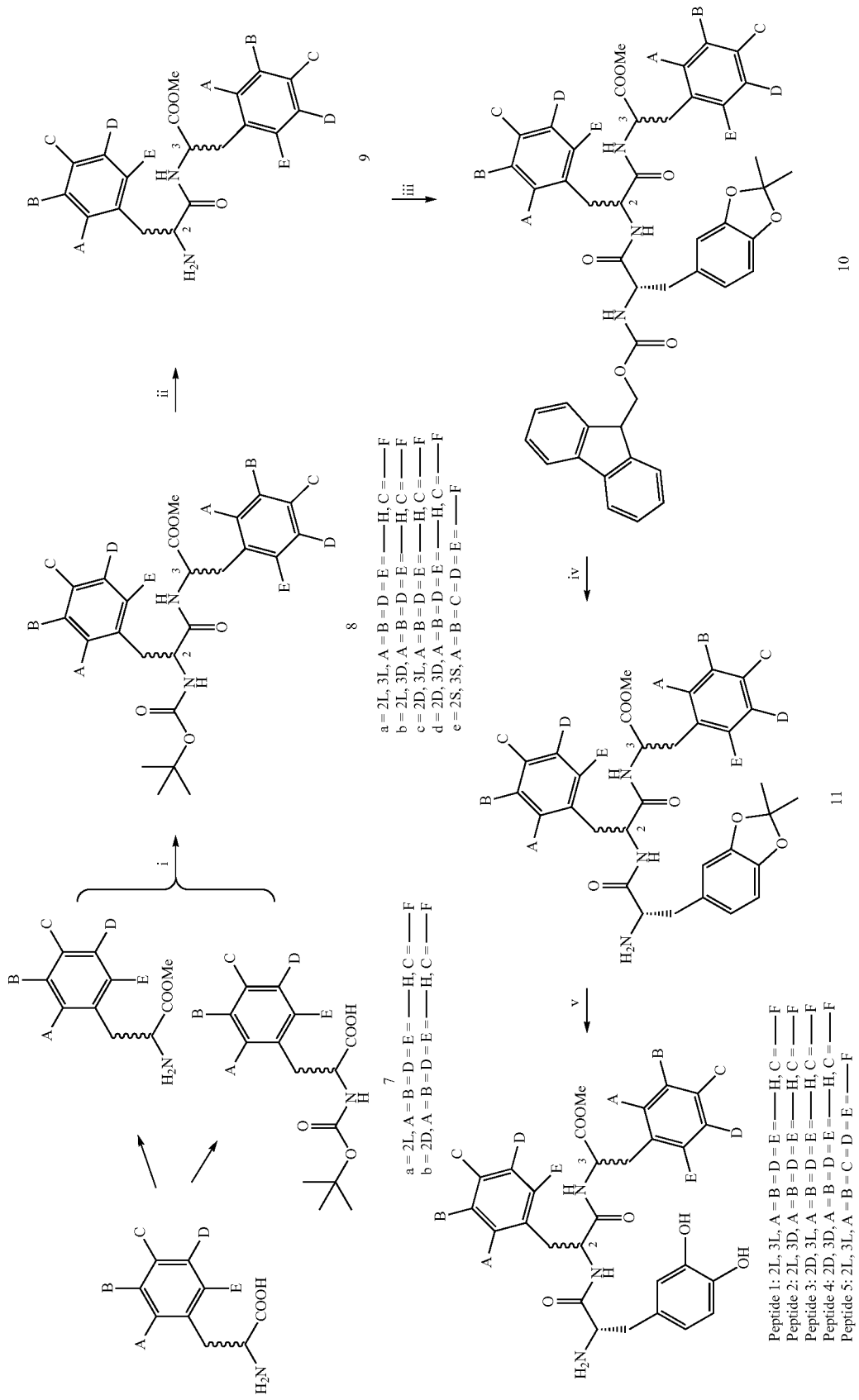

A. Synthesis of Peptide 1

1. Boc-L-(4F)Phe-COOH 7a

A solution of L-4F-Phe-COOH 1.97 g (10 mmol) in a mixture of dioxane (20 mL), water (20 mL) and 1 M NaOH (10 mL) was stirred and cooled in an ice-water bath. Ditert-butylpyrocarbonate 2.4 g (11 mmol) was added and stirring was continued at room temperature for 6 h. Then the solution was concentrated in vacuum to about 15-20 mL, cooled in an ice water bath, covered with a layer of ethyl acetate (about 30 mL) and a dilute solution of $KHSO_4$ was added to acidify (pH 2-3). The aqueous phase was extracted with ethyl acetate and this operation was done three times. The ethyl acetate extracts were collected and dried over anhydrous $Na_2SO_4$ and evaporated in a vacuum. The pure material was obtained as a waxy solid.

Yield: 2.115 g (7.25 mmol, 72.5%)

$^1$H NMR (DMSO-$d_6$, 400 MHz, $\delta_{ppm}$): 12.60 [s, 1H COOH], 7.29-7.25 & 7.11-7.07 [m, 4H, Aromatic protons], 4.10-3.00 [m, 1H, CαH 4F Phe], 3.03-2.77 [m, 2H, CβH 4F Phe], 1.33 [s, 9H, Boc].

MALDI-TOF (matrix:α-cyano-4-hydroxy cinnamic acid (CHCA)): m/z=[M+H]+ 284.12 (calculated), 284.29 (observed), [M+Na]+ 306.11 (calculated), 306.25 (observed).

2. Boc-L-(4F)Phe(2)-L-(4F)Phe(3)-COOMe 8a 500 mg (1.766 mmol) of Boc-L-(4F)Phe-OH was dissolved in 25 mL dry DCM in an ice-water bath. $NH_2$-L-(4F)Phe-OMe 697.13 mg (3.532 mmol) was isolated from the corresponding methyl ester hydrochloride by neutralization, subsequent extraction with ethyl acetate and solvent evaporation. It was then added to the reaction mixture, followed immediately by 365 mg (1.766 mmol) dicyclohexylcarbodiimide (DCC) and 239 mg (1.766 mmol) of HOBt. The reaction mixture was allowed to come to room temperature and stirred for 48 h. DCM was evaporated and the residue was dissolved in ethyl acetate (60 mL) and dicyclohexyl urea (DCU) was filtered off. The organic layer was washed with 2 M HCl (3×30 mL), brine (2×30 mL), 1 M sodium carbonate (3×30 mL) and brine (2×30 mL) and dried over anhydrous sodium sulfate; and evaporated in a vacuum to yield compound 8a, as a white solid. The product was purified by silica gel (100-200 mesh) using n hexane-ethyl acetate (4:1) as eluent.

Yield: 616.6 mg (1.334 mmol, 75.5%)

$^1$H NMR (CDCl$_3$, 400 MHz, $\delta_{ppm}$): 7.16-7.12 & 6.99-6.90 [m, 8H, Aromatic protons], 6.27-6.25 [d, 1H, NH 4F Phe(3)], 4.93 [b, 1H, NH 4F Phe(2)], 4.77-4.72 [m, 1H, CαH 4F Phe(3)], 4.28-4.27 [m, 1H, CαH 4F Phe(2)], 3.67 [s, 3H, OMe], 3.08-2.98 [m, 4H, CβH 4F Phe(2) and 4F Phe(3)], 1.41 [s, 9H, Boc].

MALDI-TOF (matrix:α-cyano-4-hydroxy cinnamic acid (CHCA)): m/z=[M+Na]$^+$ 485.18 (calculated), 485.45 (observed), [M+K]$^+$ 501.16 (calculated), 501.32 (observed).

3. NH$_2$-L-(4F)Phe(2)-L-(4F)Phe(3)-COOMe 9a 600 mg (1.298 mmol) compound 8a was dissolved in 16 mL of DCM in an ice bath. Then 4 ml of TFA was added and stirred for 2 h. The progress of reaction was monitored through TLC (Thin layer chromatography). After completion of reaction all the solvents were evaporated in rotary evaporator. The product was dissolved in water, neutralized with NaHCO$_3$ solution and extracted with ethyl acetate, dried over anhydrous sodium sulphate, evaporated into rotary evaporator to get oily product 9a.

Yield: 435.3 mg (1.202 mmol, 92.6%)

$^1$H NMR (DMSO-$d_6$, 400 MHz, $\delta_{ppm}$): 9.06-9.05 [d, 1H, NH 4F Phe(3)], 7.32-7.26 & 7.17-7.04 [m, 8H, Aromatic protons], 4.57-4.51 [m, 1H, CαH 4F Phe(3)], 4.04-3.96 [m, 1H, CαH 4F Phe(2)], 3.61 [s, 3H, OMe], 3.18-2.91 [m, 4H, CβH 4F Phe(2) and 4F Phe(3)].

MALDI-TOF (matrix:α-cyano-4-hydroxy cinnamic acid (CHCA)): m/z=[M+2H]$^+$ 364.14 (calculated), 364.34 (observed), [M+H$_2$O]$^+$ 480.15 (calculated), 480.35 (observed).

4. Fmoc-L-DOPA(ac)-L-(4F)Phe(2)-L-(4F)Phe(3)-COOMe 10a 430 mg (1.187 mmol) of compound 9a was dissolved in 25 mL dry DCM in an ice-water bath and 652.37 mg (1.42 mmol) of Fmoc-L-DOPA(ac)-COOH was added. Then 245 mg (1.187 mmol) dicyclohexylcarbodiimide (DCC) and 161 mg (1.187 mmol) of HOBt were added to reaction mixture. The reaction mixture was allowed to come to room temperature and stirred for 48 h. DCM was evaporated and the residue was dissolved in ethyl acetate (60 mL) and dicyclohexylurea (DCU) was filtered off. The organic layer was washed with water, extracted, dried over anhydrous sodium sulfate and evaporated in a vacuum to yield compound 10a, as a white solid. The product was purified by silica gel (100-200 mesh) using n hexane-ethyl acetate (4:1) as eluent.

Yield: 594.8 mg (0.74 mmol, 62.4%).

$^1$H NMR (CDCl$_3$, 400 MHz, $\delta_{ppm}$): 7.77-7.75, 7.54-7.50, 7.42-7.38, 7.33-7.29 [d & m, 8H, Fmoc aromatic protons], 7.05-6.86 [m, 8H, 4F Phe(2) and 4F Phe(3) aromatic protons], 6.62-6.55 [s & m, 3H, DOPA aromatic protons], 6.50 [b, 1H, NH 4F Phe(2)], 6.19 [b, 1H, NH 4F Phe(3)], 5.17 [b, 1H, NH DOPA], 4.68-4.66 [m, 1H, CαH DOPA], 4.54-4.52 [m, 1H, CαH 4F Phe(2)], 4.47-4.42 [m, 1H, CαH 4F Phe(3)], 4.31 (b, 2H, CβH Fmoc], 4.20-4.17 [m, 1H, CαH Fmoc], 3.65 [s, 3H, OMe], 2.98-2.92 [m, 6H, CβH 4F Phe(2) 4F Phe(3) & DOPA], 1.62 [s, 6H, 2×COCH$_3$].

MALDI-TOF (matrix:α-cyano-4-hydroxy cinnamic acid (CHCA)): m/z=[M+H]$^+$ 804.31 (calculated), 804.70 (observed), [M+Na+2H]$^+$ 828.30 (calculated), 828.07 (observed), [M+K+H]$^+$ 843.27 (calculated), 843.60 (observed).

5. NH$_2$-L-DOPA(ac)-L-(4F)Phe(2)-L-(4F)Phe(3)-COOMe 11a 580 mg (0.721 mmol) of compound 10a was treated 15 mL with 20% Piperidine solution and stirred for 3 h in room temperature. The completion of reaction was monitored by TLC. Then the solution was lyophilized and purified with column chromatography to get pure sticky compound 11a.

Yield: 275.6 mg (0.474 mmol, 65.8%)

$^1$H NMR (DMSO-$d_6$, 400 MHz, $\delta_{ppm}$): 8.53 [b, 1H, NH 4F Phe(2)], 7.96 [b, 1H, NH 4F Phe(3)], 7.24-7.23, 7.10-7.04 [m, 8H, 4F Phe(2) and 4F Phe(3) aromatic protons], 6.69-6.65, 6.55-6.53 [m, 3H, DOPA aromatic protons], 5.56 [m, 1H, CαH DOPA], 4.56 [m, 1H, CαH 4F Phe(2)], 4.47 [m, 1H, 4F Phe(3)], 3.61 [s, 3H, OMe], 3.12-2.73 [m, 6H, CβH 4F Phe(2) 4F Phe(3) & DOPA], 1.61-1.58 [d, 6H, 2×COCH$_3$].

MALDI-TOF (matrix:α-cyano-4-hydroxy cinnamic acid (CHCA)): m/z=[M+H]$^+$ 582.23 (calculated), 582.25 (observed), [M+Na]$^+$ 604.22 (calculated), 604.37 (observed), [M+K]$^+$ 620.20 (calculated), 620.19 (observed).

6. NH₂-L-DOPA-L(4F)-Phe(2)-L(4F)-Phe(3)-COOMe 1

260 mg (0.447 mmol) of compound 11a, was stirred in 10 mL of 95% TFA in water for 6 h. The progress of the reaction was monitored through TLC. After completion of reaction the solvent was evaporated in rotary evaporator. The product was washed with hexane, cold ether and water three times each to get final peptide 1.

Yield: 139.1 mg (0.257 mmol, 57.5%)

$^1$H NMR (DMSO-d$_6$, 500 MHz, $\delta_{ppm}$): 8.72-8.70 [d, 1H, NH 4F Phe(2)], 8.66-8.64 [d, 1H, NH 4F Phe(3)], 7.88 [b, 2H, OH DOPA], 7.29-7.23, 7.12-7.05 [m, 8H, 4F Phe(2) and 4F Phe(3) aromatic protons], 6.7-6.64, 6.5-6.47 [m, 3H, DOPA aromatic protons], 4.60-4.58 [m, 1H, CαH 4F Phe(2)], 4.53-4.52 [m, 1H, CαH 4F Phe(3)], 3.83 [m, 1H, CαH DOPA], 3.58 [s, 3H, OMe], 3.08-2.75 [m, 6H, CβH 4F Phe(2) 4F Phe(3) & DOPA]. $^{13}$C NMR (DMSO-d$_6$, 125 MHz, $\delta_{ppm}$): 171.9, 170.1, 168.5, 158.9, 158.54, 145.2, 144.5, 131.5, 125.2, 117.4, 115.5, 115.4, 115.3, 11.2, 114.5, 53.9, 52.3, 47.5, 36.2, 33.8, 25.8, 24.9. $^{19}$F NMR (DMSO-d6, 470 MHz, $\delta_{ppm}$): −116.42, −116.71.

MALDI-TOF (matrix:α-cyano-4-hydroxy cinnamic acid (CHCA)): m/z=[M+H]$^+$ 542.20 (calculated), 542.57 (observed), [M+Na]$^+$ 564.19 (calculated), 564.46 (observed), [M+K]$^+$ 580.16 (calculated), 580.32 (observed).

B. Synthesis of Peptide 2

1. Boc-L-(4F)Phe(2)-D-(4F)Phe(3)-COOMe 8b

The compound was synthesized with the same procedure as compound 8a.

$^1$H NMR (CDCl$_3$, 400 MHz, $\delta_{ppm}$): 7.13-7.10 & 6.98-6.91 [m, 8H, Aromatic protons], 6.51 [b, 1H, NH 4F Phe(3)], 4.91-4.89 [d, 1H, NH 4F Phe(2)], 4.82-4.77 [m, 1H, CαH 4F Phe(3)], 4.33 [m, 1H, CαH 4F Phe(1)], 3.68 [s, 3H, OMe], 3.09-2.93 [m, 4H, CβH 4F Phe(2) and 4F Phe(3)], 1.38 [s, 9H, Boc].

MALDI-TOF (matrix:α-cyano-4-hydroxy cinnamic acid (CHCA)): m/z=[M+2H]$^+$ 464.21 (calculated), 464.15 (observed), [M+Na+2H]$^+$ 586.18 (calculated), 586.37, [M+K+H]$^+$ 502.16 (calculated), 502.25 (observed).

2. NH₂-L-(4F)Phe(2)-D-(4F)Phe(3)-COOMe 9b

The compound was synthesized with the same procedure as compound 9a.

$^1$H NMR (DMSO-d$_6$, 400 MHz, $\delta_{ppm}$): 8.34 [d, 1H, NH 4F Phe(3)], 7.23-7.19 & 7.12-7.01 [m, 8H, Aromatic protons], 4.61-4.51 [m, 1H, CαH 4F Phe(3)], 3.62 [s, 3H, OMe], 3.44-3.41 [m, 1H, CαH 4F Phe(2)], 3.03-2.74 [m, 4H, CβH 4F Phe(2) and 4F Phe(3)]. 2.35 (b, 2H, free NH$_2$].

MALDI-TOF (matrix:α-cyano-4-hydroxy cinnamic acid (CHCA)): m/z=[M+2H]$^+$ 364.14 (calculated), 364.41 (observed).

3. Fmoc-L-DOPA(ac)-L-(4F)Phe(2)-D-(4F)Phe(3)-COOMe 10b

The compound was synthesized with the same procedure as compound 10a.

$^1$H NMR (DMSO-d$_6$, 400 MHz, $\delta_{ppm}$): 8.68-8.55 [d, 1H, NH Phe(2)], 8.15-7.92 [d, 1H, NH 4F Phe(3)], 7.88-7.86, 7.61-6.96 [d & m, 16H, Fmoc aromatic protons, 4F Phe(2) and 4F Phe(3) aromatic protons], 6.75 & 6.64 [s, 3H, DOPA aromatic protons], 5.83 [d, 1H, NH DOPA], 4.62-4.53 [m, 2H, CαH 4F Phe(2) and Phe(3)], 4.14-4.02 [m, 3H, CαH DOPA & CβH Fmoc], 3.63 [s, 3H, OMe], 2.76-2.57 [m, 6H, CβH 4F Phe(2), 4F Phe(3) & DOPA], 1.55 [s, 6H, 2×COCH$_3$].

MALDI-TOF (matrix:α-cyano-4-hydroxy cinnamic acid (CHCA)): m/z=[M+Na]$^+$ 826.29 (calculated), 826.15 (observed), [M+K]$^+$ 842.27 (calculated), 841.94 (observed).

4. NH₂-L-DOPA(ac)-L-(4F)Phe(2)-D-(4F)Phe(3)-COOMe 11b

The compound was synthesized with the same procedure as compound 11a.

$^1$H NMR (DMSO-d$_6$, 400 MHz, $\delta_{ppm}$): 8.66-8.64 [b, 1H, NH 4F Phe(2)], 7.95 [b, 1H, NH 4F Phe(3)], 7.30-6.80 [m, 8H, 4F Phe(2) and 4F Phe(3) aromatic protons], 6.68-6.64, 6.56-6.53 [m, 3H, DOPA aromatic protons], 5.57-5.55 [m, 1H, CαH DOPA], 4.56 [m, 1H, CαH 4F Phe(2)], 4.47 [m, 1H, 4F Phe(3)], 3.63 [s, 3H, OMe], 3.05-2.67 [m, 6H, CβH 4F Phe(2), 4F Phe(3) & DOPA]. 1.59-1.57 [s, 6H, 2×COCH$_3$].

MALDI-TOF (matrix:α-cyano-4-hydroxy cinnamic acid (CHCA)): m/z=[M+Na]$^+$ 604.22 (calculated), 604.06 (observed), [M+K]$^+$ 620.20 (calculated), 619.88 (observed).

5. NH₂-L-DOPA-L-(4F)Phe(2)-D-(4F)Phe(3)-COOMe 2

The peptide 2 was synthesized with the same procedure as peptide 1.

$^1$H NMR (DMSO-d$_6$, 500 MHz, $\delta_{ppm}$): 8.77-8.75 [d, 1H, NH 4F Phe(2)], 8.66-8.64 [d, 1H, NH 4F Phe(3)], 7.80 [b, 2H, OH DOPA], 7.27-7.24, 7.11-7.00 [m, 8H, 4F Phe(2) and 4F Phe(3) aromatic protons], 6.71-6.60 [m, 3H, DOPA aromatic protons], 5.15 [b, 2H, NH2], 4.62-4.60 [m, 1H, CαH 4F Phe(2)], 4.52-4.49 [m, 1H, CαH 4F Phe(3)], 3.83 [m, 1H, CαH DOPA], 3.65 [s, 3H, OMe], 3.10-2.73 [m, 6H, CβH 4F Phe(2), 4F Phe(3) & DOPA]. $^{13}$C NMR (DMSO-d$_6$, 125 MHz, $\delta_{ppm}$): 117.43, 170.42, 147.86, 146.63, 143.75, 143.69, 141.30, 135.47, 128.64, 127.75, 127.23, 127.13, 125.054, 121.81, 120.02, 118.04, 109.44, 108.25, 67.20, 53.02, 52.33, 47.09, 37.91, 31.94, 29.71, 25.89.

$^{19}$F NMR (DMSO-d$_6$, 470 MHz, $\delta_{ppm}$): −116.43, −116.91.

MALDI-TOF (matrix:α-cyano-4-hydroxy cinnamic acid (CHCA)): m/z=[M+H]$^+$ 542.20 (calculated), 542.65 (observed), [M+Na]$^+$ 564.19 (calculated), 564.55 (observed), [M+K]$^+$ 580.16 (calculated), 580.57 (observed).

C. Synthesis of Peptide 3

1. Boc-D-(4F)Phe-COOH 7b

The compound 7b was synthesized as compound 7a.

$^1$H NMR (DMSO-d$_6$, 400 MHz, $\delta_{ppm}$): 12.59 [s, 1H COOH], 7.29-7.26 & 7.12-7.08 [m, 4H, Aromatic protons], 4.10-3.57 [m, 1H, CαH 4F Phe], 3.03-2.77 [m, 2H, CβH 4F Phe], 1.32 [s, 9H, Boc].

MALDI-TOF (matrix:α-cyano-4-hydroxy cinnamic acid (CHCA)): m/z=[M+H]$^+$ 284.12 (calculated), 284.36 (observed), [M+Na]$^+$ 306.11 (calculated), 306.28 (observed).

2. Boc-D-(4F)Phe(2)-L-(4F)Phe(3)-COOMe 8c

The compound was synthesized with the same procedure as compound 8a.

$^1$H NMR (CDCl$_3$, 400 MHz, $\delta_{ppm}$): 7.14-7.09 & 6.99-6.93 [m, 8H, Aromatic protons], 6.50 [b, 1H, NH 4F Phe(3)], 4.88

[b, 1H, NH 4F Phe(2)], 4.82-4.77 [m, 1H, CαH 4F Phe(3)], 4.33 [m, 1H, CαH 4F Phe(2)], 3.68 [s, 3H, OMe], 3.09-2.91 [m, 4H, CβH 4F Phe(2) and 4F Phe(3)], 1.38 [s, 9H, Boc].

MALDI-TOF (matrix:α-cyano-4-hydroxy cinnamic acid (CHCA)): m/z=[M+Na]$^+$ 485.18 (calculated), 485.88 (observed), [M+K]$^+$ 501.16 (calculated), 501.75 (observed).

3. NH$_2$-D-(4F)Phe(2)-L-(4F)Phe(3)-COOMe 9c

The compound was synthesized with the same procedure as compound 9a.

$^1$H NMR (DMSO-d$_6$, 400 MHz, δ$_{ppm}$): 8.71-8.67 [d, 1H, NH 4F Phe(3)], 7.25-7.21 & 7.12-7.03 [m, 8H, Aromatic protons], 5.49 [b, 2H, NH$_2$], 4.56-4.54 [m, 1H, CαH 4F Phe(2)], 3.77-3.70[m, 1H, CαH 4F Phe(3)], 3.64 [s, 3H, OMe] 3.07-2.57 [m, 4H, CβH 4F Phe(2) and 4F Phe(3)].

MALDI-TOF (matrix:α-cyano-4-hydroxy cinnamic acid (CHCA)): m/z=[M+2H]$^+$ 364.14 (calculated), 364.26 (observed).

4. Fmoc-L-DOPA(ac)-D-(4F)Phe(2)-L-(4F)Phe(3)-COOMe 10c

The compound was synthesized with the same procedure as compound 10a.

$^1$H NMR (CDCl$_3$, 400 MHz, δ$_{ppm}$): 7.79-7.72, 7.51-7.47, 7.42-7.38, 7.33-7.29 [d & m, 8H, Fmoc aromatic protons], 6.94-6.88 [m, 8H, 4F Phe(2) and 4F Phe(3) aromatic protons], 6.76-6.61[s & m, 3H, DOPA aromatic protons], 6.54 [b, 1H, NH 4F Phe(2)], 6.18 [b, 1H, NH 4F Phe(3)], 5.20 [b, 1H, NH DOPA], 4.76-4.68 [m, 1H, CαH DOPA], 4.67-4.57 [m, 1H, CαH 4F Phe(2)], 4.43-4.35 [m, 1H, CαH 4F Phe(3)], 4.30-4.21 [m, 1H, CαH Fmoc], 4.19-4.01 (b, 2H, CβH Fmoc], 3.62 [s, 3H, OMe], 3.09-2.75 [m, 6H, CβH 4F Phe(2), 4F Phe(3) & DOPA], 1.63 [s, 6H, 2×COCH$_3$].

MALDI-TOF (matrix:α-cyano-4-hydroxy cinnamic acid (CHCA)): m/z=[M+H]$^+$ 804.31 (calculated), 804.74 (observed), [M+Na+H]$^+$ 827.30 (calculated), 827.32 (observed), [M+K+H]$^+$ 843.27 (calculated), 843.62 (observed).

5. NH$_2$-L-DOPA(ac)-D-(4F)Phe(2)-L-(4F)Phe(3)-COOMe 11c

The compound was synthesized with the same procedure as compound 11a.

$^1$H NMR (DMSO-d$_6$, 400 MHz, δ$_{ppm}$): 8.66-8.64 [b, 1H, NH 4F Phe(2)], 7.95 [b, 1H, NH 4F Phe(3)], 7.29-6.81 [m, 8H, 4F Phe(2) and 4F Phe(3) aromatic protons], 6.68-6.64, 6.54-6.53 [m, 3H, DOPA aromatic protons], 5.57-5.55 [m, 1H, CαH DOPA], 4.60 [m, 1H, CαH 4F Phe(2)], 4.48 [m, 1H, 4F Phe(3)], 3.63 [s, 3H, OMe], 2.88-2.73 [m, 6H, CβH 4F Phe(2), 4F Phe(3) & DOPA]. 1.59-1.56 [s, 6H, 2×COCH$_3$].

MALDI-TOF (matrix:α-cyano-4-hydroxy cinnamic acid (CHCA)): m/z=[M+H]$^+$ 582.23 (calculated), 581.93 (observed), [M+Na]$^+$ 604.22 (calculated), 604.01 (observed), [M+K]$^+$ 620.20 (calculated), 619.85 (observed).

6. NH$_2$-L-DOPA-D-(4F)Phe(2)-L-(4F)Phe(3)-COOMe 3

The peptide 3 was synthesized with the same procedure as peptide 1.

$^1$H NMR (DMSO-d$_6$, 500 MHz, δ$_{ppm}$): 8.72-8.71 [d, 1H, NH 4F Phe(2)], 8.65-8.64 [d, 1H, NH 4F Phe(3)], 7.89 [b, 2H, OH DOPA], 7.28-7.23, 7.12-7.06 [m, 8H, 4F Phe(2) and 4F Phe(3) aromatic protons], 6.67-6.64, 6.49-6.47 [m, 3H, DOPA aromatic protons], 4.61-4.50 [m, 1H, CαH 4F Phe(2)& Phe(3)], 3.85-3.80 [m, 1H, CαH DOPA], 3.58 [s, 3H, OMe], 3.05-2.72 [m, 6H, CβH 4F Phe(2), 4F Phe(3) & DOPA]. $^{13}$C NMR (DMSO-d$_6$, 125 MHz, δ$_{ppm}$): 171.9, 170.9, 168.6, 162.5, 160.6, 158.5, 158.23, 145.7, 145.1, 133.8, 133.7, 133.5, 131.5, 125.8, 120.7, 117.3, 116.1, 115.5, 115.4, 115.3, 115.2, 54.3, 53.9, 52.4, 46.2, 37.3, 37.0, 36.2, 26.7, 25.3, 24.7.

$^{19}$F NMR (DMSO-d$_6$, 470 MHz, δ$_{ppm}$): −116.31, −116.53.

MALDI-TOF (matrix:α-cyano-4-hydroxy cinnamic acid (CHCA)): m/z=[M+H]$^+$ 542.20 (calculated), 542.51 (observed), [M+Na]$^+$ 564.19 (calculated), 564.53 (observed), [M+K]$^+$ 580.16 (calculated), 580.43 (observed).

D. Synthesis of Peptide 4

1. Boc-D-(4F)Phe(2)-D-(4F)Phe(3)-COOMe 8d

The compound was synthesized with the same procedure as compound 8a.

$^1$H NMR (CDCl$_3$, 400 MHz, δ$_{ppm}$): 7.18-7.15 & 7.01-6.925 [m, 8H, Aromatic protons], 6.25-6.23 [d, 1H, NH 4F Phe(3)], 4.93 [b, 1H, NH 4F Phe(2)], 4.77-4.76 [m, 1H, CαH 4F Phe(2)], 4.30-4.28 [m, 1H, CαH 4F Phe(3)], 3.7 [s, 3H, OMe], 3.10-3.00 [m, 4H, CβH 4F Phe(2) and 4F Phe(3)], 1.40 [s, 9H, Boc].

MALDI-TOF (matrix:α-cyano-4-hydroxy cinnamic acid (CHCA)): m/z=[M+Na+H]$^+$ 486.18 (calculated), 485.93 (observed), [M+K+H]$^+$ 502.16 (calculated), 502.00 (observed).

2. NH$_2$-D-(4F)Phe(2)-D-(4F)Phe(3)-COOMe 9d

The compound was synthesized with the same procedure as compound 9a.

$^1$H NMR (DMSO-d$_6$, 400 MHz, δ$_{ppm}$): 8.36-8.34 [d, 1H, NH 4F Phe(3)], 8.02 [b, 1H, NH 4F Phe(2)], 7.22-7.17 & 7.11-7.01 [m, 8H, aromatic protons], 4.55-4.50 [m, 1H, CαH 4F Phe(3)], 4.08-3.92 [m, 1H, CαH 4F Phe(2)], 3.60 [s, 3H, OMe], 3.04-2.84 [m, 4H, CβH 4F Phe(2) and 4F Phe(3)].

MALDI-TOF (matrix:α-cyano-4-hydroxy cinnamic acid (CHCA)): m/z=[M+2H]$^+$ 364.14 (calculated), 364.29 (observed), [M+Na+H]$^+$ 486.13 (calculated), 486.33 (observed).

3. Fmoc-L-DOPA(ac)-D-(4F)Phe(2)-D-(4F)Phe(3)-COOMe 10d

The compound was synthesized with the same procedure as compound 10a.

$^1$H NMR (CDCl$_3$, 400 MHz, δ$_{ppm}$): 7.77-7.75, 7.55-7.53, 7.42-7.40 [d & m, 8H, Fmoc aromatic protons], 6.94-6.55 [m, 8H, 4F Phe(2) and 4F Phe(3) aromatic protons], 6.71-6.52 [m, 3H, DOPA aromatic protons], 6.52-6.45 [b, 1H, NH 4F Phe(2)], 6.15 [b, 1H, NH 4F Phe(3)], 5.31 [b, 1H, NH DOPA], 4.73-4.65 [m, 1H, CαH DOPA], 4.64-4.56 [m, CαH 4F Phe(2)], 4.51-4.42 [m, 1H, CαH 4F Phe(3)], 4.24-4.11 [m, 1H, CαH Fmoc], 4.19 (b, 2H, CβH Fmoc], 3.61 [s, 3H, OMe], 3.08-2.72 [m, 6H, CβH 4F Phe(2) 4F Phe(3) & DOPA], 1.62 [s, 6H, 2×COCH$_3$].

MALDI-TOF (matrix:α-cyano-4-hydroxy cinnamic acid (CHCA)): m/z=[M+Na+2H]$^+$ 828.30 (calculated), 828.03 (observed), [M+K+2H]$^+$ 844.27 (calculated), 844.12 (observed).

4. NH$_2$-L-DOPA(ac)-D-(4F)-Phe(2)-D-(4F)-Phe(3)-COOMe 11d

The compound was synthesized with the same procedure as compound 11a.

$^1$H NMR (DMSO-d$_6$, 400 MHz, δ$_{ppm}$): 8.58-8.53 [d, 1H, NH 4F Phe(2)], 8.12 [d, 1H, NH 4F Phe(3)], 7.31-7.09 [m, 8H, 4F Phe(2) and 4F Phe(3) aromatic protons], 6.69-6.68, 6.61-6.60 [m, 3H, DOPA aromatic protons], 5.63-5.61 [m, 1H, CαH DOPA], 4.61 [m, 1H, CαH 4F Phe(2)], 4.52 [m, 1H, 4F Phe(3)], 3.64 [s, 3H, OMe], 3.15-2.65 [m, 6H, CβH 4F Phe(2) 4F Phe(3) & DOPA]. 1.54 [d, 6H, 2×COCH$_3$].

MALDI-TOF (matrix:α-cyano-4-hydroxy cinnamic acid (CHCA)): m/z=[M+Na]$^+$ 604.22 (calculated), 604.23 (observed), [M+K]$^+$ 620.20 (calculated), 620.12 (observed).

5. NH$_2$-L-DOPA-D-(4F)Phe(2)-D-(4F)Phe(3)-COOMe 4

The peptide 4 was synthesized with the same procedure as peptide 1.

$^1$H NMR (DMSO-d$_6$, 500 MHz, δ$_{ppm}$): 8.80-8.77 [d, 1H, NH 4F Phe(2)], 7.95 [b, 2H, OH DOPA], 7.31-7.20, 7.12-7.03 [m, 8H, 4F Phe(2) and 4F Phe(3) aromatic protons], 6.59-6.57, 6.22-6.20 [m, 3H, DOPA aromatic protons], 5.58 [b, 2H, free NH2)], 4.75-4.62 [m, 1H, CαH 4F Phe(2)], 4.51-4.45 [m, 1H, CαH 4F Phe(3)], 3.91-3.82 [m, 1H, CαH DOPA], 3.62 [s, 3H, OMe], 3.08-2.62 [m, 6H, CβH 4F Phe(2), 4F Phe(3) & DOPA]. $^{13}$C NMR (DMSO-d$_6$, 125 MHz, δ$_{ppm}$): 172.01, 171.20, 168.27, 162.77, 158.59, 158.27, 157.09, 145.65, 145.02, 133.58, 133.71, 131.46, 131.45, 131.37, 125.74, 120.65, 117.37, 115.95, 115.63, 115.42, 115.31, 115.09, 54.14, 52.44, 47.97, 33.80, 25.78, 24.92. $^{19}$F NMR (DMSO-d6, 470 MHz, δ$_{ppm}$): −116.08, −116.42.

MALDI-TOF (matrix:α-cyano-4-hydroxy cinnamic acid (CHCA)): m/z=[M+H]$^+$ 542.20 (calculated), 542.85 (observed), [M+Na]$^+$ 564.19 (calculated), 564.55 (observed), [M+K]$^+$ 580.16 (calculated), 580.40 (observed).

E. Synthesis of peptide 5

1. Boc-L-(F5)Phe(2)-L-(F5)Phe(3)-COOMe 8e

We have purchased Boc-L-(F5)Phe-COOH. We first deprotected the Boc group by treatment of TFA/DCM, then evaporate all the solvents and esterification of NH$_2$-Phe(F5)-COOH was done by treating with thionyl chloride and methanol. Then the compound 8e was synthesized by coupling of Boc-L-(F5)Phe-COOH with NH$_2$-L-(F5)Phe-COOMe as described for compound 8a.

$^1$H NMR (CDCl$_3$, 400 MHz, δ$_{ppm}$): 6.52 [b, 1H, NH Phe(3)], 4.93 [b, 1H, NH 4F Phe(2)], 4.92-4.85 [m, 1H, CαH Phe(3)], 4.42-4.29 [m, 1H, CαH Phe(2)], 3.81 [s, 3H, OMe], 3.42-2.95 [m, 4H, CβH Phe(2) and Phe(3)], 1.44 [s, 9H, Boc].

MALDI-TOF (matrix:α-cyano-4-hydroxy cinnamic acid (CHCA)): m/z=[M+Na+H]$^+$ 630.11 (calculated), 630.08 (observed), [M+K+H]$^+$ 646.08 (calculated), 646.13 (observed).

2. NH$_2$-L-(F5)Phe(2)-L-(F5)Phe(3)-COOMe 9e

The compound 9e was prepared as described for compound 9a.

$^1$H NMR (DMSO-d$_6$, 400 MHz, δ$_{ppm}$): 8.93-8.90 [d, 1H, NH Phe(3)], 8.40 [b, 1H, free NH$_2$], 4.72-4.70 [m, 1H, CαH Phe(3)], 3.90 [m, 1H, CαH Phe(2)], 3.61 [s, 3H, OMe], 3.17-2.99 [m, 4H, CβH Phe(2) and Phe(3)].

MALDI-TOF (matrix:α-cyano-4-hydroxy cinnamic acid (CHCA)): m/z=[M+Na+H]$^+$ 530.05 (calculated), 530.16 (observed), [M+K+H]$^+$ 546.03 (calculated), 646.53 (observed).

3. Fmoc-DOPA(ac)-L-(F5)Phe(2)-L-(F5)Phe(3)-COOMe 10e

The compound 10e was prepared as described for compound 10a.

$^1$H NMR (DMSO-d$_6$, 400 MHz, δ$_{ppm}$): 8.75-8.72 [d, 1H, NH Phe(2)], 8.36-8.34 [b, 1H, NH Phe(3)], 7.88-7.26 [m, 8H, Fmoc aromatic protons], 6.79-6.67 [m, 3H, DOPA aromatic protons], 5.57-5.55 [b, 1H, NH DOPA], 4.66-4.63 [m, 2H, CβH Fmoc], 4.14-4.09 [m, 3H, CαH DOPA, CαH Phe(2), CαH Phe(3)], 3.62 [s, 3H, OMe], 3.05-2.90 [m, 6H, CβH Phe(2), Phe(3) & DOPA], 1.56 [s, 6H, 2×COCH$_3$].

MALDI-TOF (matrix:α-cyano-4-hydroxy cinnamic acid (CHCA)): m/z=[M+Na]$^+$ 970.21 (calculated), 970.22 (observed), [M+K]$^+$ 986.19 (calculated), 986.04 (observed).

4. NH$_2$-DOPA(ac)-L-(F5)Phe(2)-L-(F5)Phe(3)-COOMe 11e

The compound 11e was prepared as described for compound 11a.

$^1$H NMR (DMSO-d$_6$, 400 MHz, δ$_{ppm}$): 8.73-8.71 [d, 1H, NH Phe(2)], 6.69-6.55 [m, 3H, DOPA aromatic protons], 5.57-5.55 [d, 1H, NH Phe(3)], 4.64-6.63 [m, 1H, CαH DOPA], 4.54 [m, 1H, CαH Phe(2)], 4.13-4.08 [m, 1H, CαH Phe(3)], 3.61 [s, 3H, OMe], 3.15-2.67 [m, 6H, CβH Phe(2), Phe(3) & DOPA], 1.60 [s, 6H, 2×COCH$_3$].

MALDI-TOF (matrix:α-cyano-4-hydroxy cinnamic acid (CHCA)): m/z=[M+Na]$^+$ 748.15 (calculated), 748.23 (observed), [M+K]$^+$ 764.12 (calculated), 764.06 (observed).

5. NH$_2$-DOPA-L-(F5)Phe(2)-L-(F5)Phe(3)-COOMe 5

The compound 5 was prepared as described for compound 1.

$^1$H NMR (DMSO-d$_6$, 400 MHz, δ$_{ppm}$): 9.46 [b, 1H, NH Phe(2)], 9.25 [b, 1H, NH Phe(2)], 8.39 [b, 2H, free NH$_2$], 6.68-6.54 [m, 3H, DOPA aromatic protons], 4.69-4.65 [m, 2H, CαH Phe (1) & Phe(2)], 4.55 [m, 1H, CαH DOPA], 3.61 [s, 3H, OMe], 3.01-2.95 67 [m, 6H, CβH Phe(2) Phe(2) & DOPA]. $^{13}$C NMR (DMSO-d$_6$, 100 MHz, δ$_{ppm}$): 193.6, 158.5, 158.2, 144.3, 140.8, 139.5, 133.7, 129.9, 128.5, 127.8, 124.4, 53.8, 44.2, 33.8, 30.5, 29.4, 22.6, 17.6. $^{19}$F (DMSO-d$_6$, 470 MHz, δ$_{ppm}$): −141.7, −142.4, −157.6, −163.1, −163.4.

MALDI-TOF (matrix:α-cyano-4-hydroxy cinnamic acid (CHCA)): m/z=[M+Na]$^+$ 748.15 (calculated), 748.23 (observed), [M+K]$^+$ 764.12 (calculated), 764.06 (observed).

F. Synthesis of peptide 6

1. Boc-L-DOPA-COOH

The compound was synthesized as compound 7a.

$^1$H NMR (DMSO-d$_6$, 400 MHz, δ$_{ppm}$): 9.13 (b, 2H, 2×OH], 7.35-7.33 [d, 1H, NH DOPA], 7.03-6.88[m, 3H, DOPA aromatic protons], 4.45-4.37 [m, 1H, CαH DOPA], 3.22-2.92 [m, 1H, CβH DOPA], 1.75 [s, 9H, OMe].

MALDI-TOF (matrix:α-cyano-4-hydroxy cinnamic acid (CHCA)): m/z=[M+Na]$^+$ 320.11 (calculated), 320.51 (observed), [M+K]$^+$ 336.08 (calculated), 336.29 (observed).

2. Boc-L-DOPA-L-(4F) Phe-COOMe

The compound was synthesized as compound 8a.

$^1$H NMR (CDCl$_3$, 400 MHz, δ$_{ppm}$): 7.26-7.24 [d, 1H, NH Phe], 6.90-6.50 [m, 7H, all aromatic protons], 5.24 [b, 1H, NH DOPA], 4.82-4.77 [m, 1H, CαH DOPA], 4.36 [b, 1H, CαH Phe], 3.64 [s, 3H, OMe], 2.99-2.87 [m, 4H, CβH DOPA & Phe], 1.42 [s, 9H, Boc].

MALDI-TOF (matrix:α-cyano-4-hydroxy cinnamic acid (CHCA)): m/z=[M+Na+H]$^+$ 500.18 (calculated), 500.02 (observed), [M+K+H]$^+$ 516.16 (calculated), 516.24 (observed).

3. NH$_2$-L-DOPA-L-(4F) Phe-COOMe 6

This compound was synthesized as described for 9a.

$^1$H NMR (DMSO-d$_6$, 400 MHz, δ$_{ppm}$): 8.92 & 8.81 [s, 2H, 2×OH], 8.02 [b, 2H, free NH$_2$], 7.27-7.09 [m, 4H, aromatic proton Phe], 6.67-6.48 [m, 3H, aromatic protons DOPA], 4.58-4.52 [m, 1H, CαH DOPA], 3.90-3.86 [b, 1H, CαH Phe], 3.61 [s, 3H, OMe], 3.08-2.67 [m, 4H, CβH DOPA & Phe]. $^{13}$C NMR (DMSO-d$_6$, 100 MHz, δ$_{ppm}$): 171.4, 168.7, 162.7, 160.4, 158.5, 145.6, 145.0, 133.3, 133.2, 131.4, 125.6, 120.6, 117.2, 115.9, 115.5, 115.3, 54.1, 53.9, 52.4, 41.0, 36.8, 36.2, 23.6.]. $^{19}$F NMR (DMSO-d$_6$, 470 MHz, δ$_{ppm}$): −(116.25-116.29).

MALDI-TOF (matrix:α-cyano-4-hydroxy cinnamic acid (CHCA)): m/z=[M+H] 377.15 (calculated), 377.25 (observed), [M+Na]$^+$ 399.13 (calculated), 399.24 (observed).

Another two exemplary peptide derivatives have been synthesized using solid or solution phase synthesis. The purity and identify of the peptides was determined using HPLC and MS spectrometer.

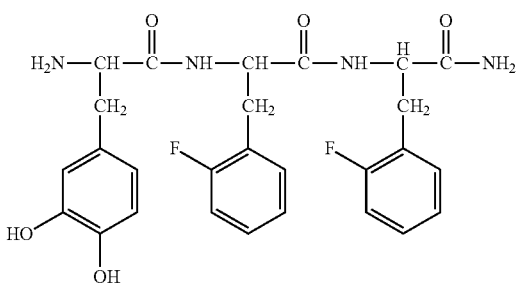

Peptide 7

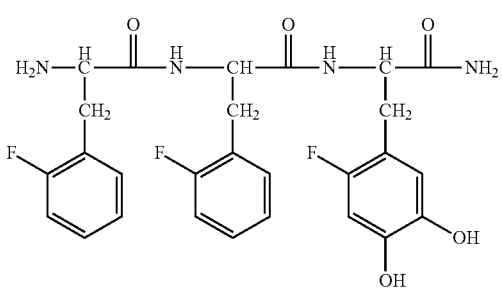

Peptide 8

Substrates

The following substrates were coated with the peptides in the course of the research: a silicon wafer, a silicon wafer with a 100 nm titanium layer, a 400 mesh Copper-Formvar®/carbon grids.

Surface Modification

10×10 mm Ti surfaces were sonicated 5 minutes in ethanol, washed with TDW and dried under nitrogen. The clean surfaces were dipped in a peptide solution (0.5 mg/mL in methanol) and left for overnight at RT. Then, they were rinsed extensively with methanol and dried under nitrogen.

The desired substrate was cut into a 1 cm$^2$ square and cleaned by sonication (5 min in acetone and 5 min in isopropanol). Then, the substrate was immersed in a peptide solution at a concentration of 0.1 mg/ml and incubated over night at room temperature.

Following incubation, the substrate was rinsed by immersion in water, dried and store in a dissector until use.

Contact Angle Measurements

Contact angle measurements were carried out using a Theta Lite optical tensiometer (Attension, Finland). Each experimental measurement consisted of three repeats, and the reported angles were averaged.

AFM Analysis

Freshly cleaved mica surfaces were dipped overnight in different peptide solution at a concentration of 0.5 mg/mL in methanol. Then, the surfaces were washed with fresh methanol and dried under N$_2$. AFM images were taken in AC mode with Si$_3$N$_2$ tip with spring constant 3 N/m in JPK instrument (NanoWizard 3).

ATR-FTIR

ATR spectra were recorded using FT-IR (Thermo scientific, Model Nicolet 6700) with Ge-ATR arrangement (Harrick Scientific's VariGATR). For all the surfaces spectra were collected with applied force of 350 N, at 4 cm$^{-1}$ resolution with 3000 scans averaged signal and an incident angle of 65°.

QCM-D

QCM-D (Q-sense, Biolin Scientific) was used for the study of peptide adhesion onto Ti surface. Measurements were performed in a flow module E1 system. Ti sensors with a fundamental resonant frequency of 5 MHz were also purchased from Q-sense and used as supplied. Prior to each experiment Ti sensors were cleaned with Oxygen/Plasma (Atto, Diener Electronic), followed by rinsing with 2% SDS and TDW and finally dried under N$_2$. All QCM-D experiments were performed under flow-through conditions using a digital peristaltic pump (IsmaTec Peristaltic Pump, IDEX) operating in pushing mode. The studied solutions were injected to the sensor crystal chamber at a rate of 0.1 mL/min Organic solvent compatible tube and O-ring were used for the flow system. Peptides were dissolved in MeOH to a concentration of 0.5 mg/mL.

The data were fitted with Sauerbrey model. According to this model the mass of adhering layer is calculated as $$\Delta m = -\frac{C \cdot \Delta f}{n}$$

where C=17.7 ng Hz-1 for 5 MHz quartz crystal and n=1, 3, 5, 7, 9, 11, 13 overtone number.

X-Ray Photoelectron Spectroscopy (XPS)

The X-ray Photoelectron Spectroscopy (XPS) measurements were performed using a Kratos AXIS Ultra X-ray photoelectron spectrometer (Kratos Analytical Ltd., Manchester, UK). Spectra were acquired using the Al-Kα monochromatic X-ray source (1,486.7 eV). Sample take-off angle was 90° (i.e. normal to the analyzer). The vacuum pressure in the analyzing chamber maintained to $2 \cdot 10^{-9}$ Torr High-resolution XPS spectra were collected for F 1s, O 1s, C 1s and Ti 2 peaks with pass energy 20 eV and 0.1 eV step size. Data analyses were done using the Kratos Vision data reducing processing software (Kratos Analytical Ltd.) and Casa XPS (Casa Software Ltd.).

Evaluation of the Layer Thickness by XPS

Using the XPS measurements, it is possible to calculate the thickness of the assembled layers. We have done so using the standard attenuation relations of the photoelectrons emerging from different sample depths. The thickness calculation is based on the Briggs et al. method and others. For the Au substrate, the overlay thickness d (nm) expressed as:

$$d = \lambda_o \sin\theta \ln\left(\frac{N_s \lambda_s I_o}{N_o \lambda_o I_s} + 1\right)$$

where $I_s$ and $I_o$ are the intensities of the peaks from the substrate and the overlayer respectively, the substrate is the Ti 2p signal, and layer is the sum of the intensities of C 1s, O 1s, N 1s and F 1s peaks, $\theta$ is the takeoff angle (in our case $\sin\theta=1$) and $N_s$ and $N_o$ are the volume densities. The inelastic mean free paths (IMFPs) parameters for substrate ($\lambda_s$) and for the overlayer ($\lambda_o$) assumed as 2.18 nm and 3.3 nm respectively. Calculated, using S. Tougard QUASES-IMFP-TPP2M software (http://www.quases.com). Inelastic electron mean free path calculated from the Tanuma, Powell and Penn algorithm [Penn, 1994].

Ellipsometry

The thickness of the peptide-based coating was measured using α-SE spectroscopic ellipsometer (J. A. Woollam, Lincoln, Nebr., USA). Measurements were performed at wavelengths from 380 to 900 nm, at a 70° angle of incidence. The optical properties of the substrate were fitted using standard Si with a 50 nm Ti. The thickness of the layers and refractive indices were fitted according to the Cauchy model. The coefficients of the Cauchy equation were initially fixed for organic layers ($A_n=1.45$, $B_n=0.01$ and $C_n=0$), and an angle offset was permitted. Then, the parameters were allowed to be fitted to determine more accurate values.

Protein Adsorption

50 μL of single protein solution of BSA, lysozyme and fibrinogen (150 μM in PBS) were pipetted onto the substrate in a petri dish. The plate was placed in a humidified incubator at 37° C. for 2 hours. The substrates were then rinsed 3 times with PBS (pH=7.43, 10 mM Nacl, 150 mM), and transferred into eppendorfs containing 1 mL of 2% (w/w) SDS. The samples were shaken for 60 minutes and sonicated for 20 minutes at room temperature to detach the adsorbed proteins. Protein concentrations in the SDS solution were determined using the Non-interfering protein assay (Calbiochem, USA) according to the instructions of the manufacturer, using a microplate reader (Synergy 2, BioTek) at 480 nm. All measurements were performed in triplicates and averaged.

To determine if the coated surfaces prevents protein adsorption, each of the examined substrates was incubated with a fluorescently-labeled protein (FITC-BSA) for 1 hour. After incubation, the substrate was rinsed exhaustively to wash access protein and the fluorescent signal was recorded using a fluorescent microscope.

Biofilm Growth

Pseudomonas aeruginosa and Eschrichia coli were grown in TSB medium (Fluka) and LB medium (BD Difco) respectively overnight at 37° C. in loosely capped tubes with agitation (120 rpm) to the stationary phase. Then, cultures were diluted to $10^8$ CFU/mL with TSB, and 3 mL of each culture were transferred to a Petri dish. Substrates were placed horizontally in the plate and incubated at 37° C. for 9 hours for the formation of biofilm by P. aeruginosa and 96 hours for the formation of biofilm by E. coli. Every 4.5 hours the medium was replaced with a fresh one to ensure sufficient supply of nutrients.

BL21 E. Coli strain was grown in LB broth to a steady state. The examined surfaces were immersed in the bacterial growth culture. After 1 hour of incubation the substrates were thoroughly rinsed with sterile PBS buffer (at least 20 ml for 1 $cm^2$ surface), in order to get rid of non adherent cells, and placed in test tube containing a clean buffer. In order to determine the number of bacteria adsorb onto the substrate, the test tube was placed in an ultrasonic bath for 5 min. The buffer was then diluted ×10 and ×100, spread on LB agar plates and incubate over night at 37° C. The number of cell forming units (CFU)/colonies was counted.

Crystal Violet Assay

After incubation, the substrates were gently rinsed 3 times with di-ionized water, and stained with 0.2% crystal violet for 15 minutes. The stained samples were washed with running water and left to dry in air. Eventually the bound dye was eluted with 30% acetic acid. Absorbance values were recorded at 590 nm in a microplate reader (Synergy 2, BioTek). All measurements were performed in triplicates and averaged.

Results

Figure 2:
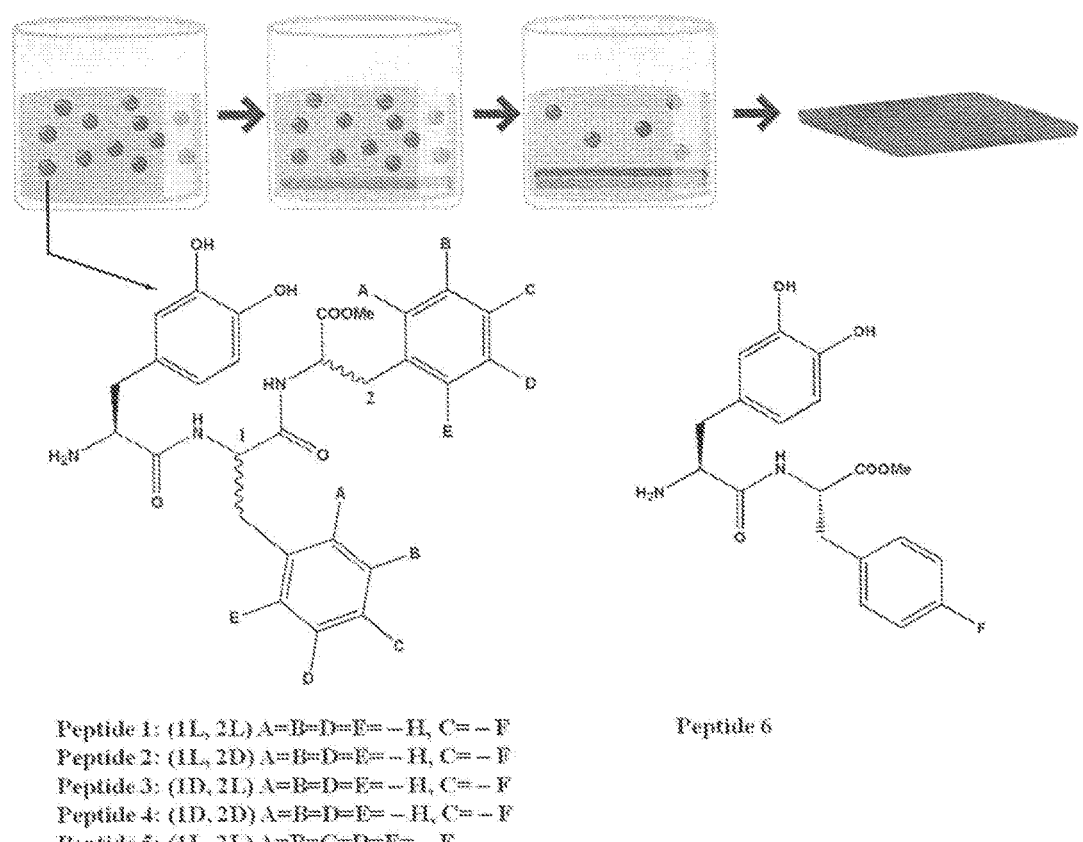
FIG. 2 shows a general scheme for the formation of a coating on a substrate by dip coating. An exemplary peptide is depicted as the molecular structures.

The molecular structure of the studied peptides 1 to 6 is presented below. We chose to explore two variation of the peptide: one contains only one fluorine atom on each of the benzene rings and the other contains five. In addition, we studied peptides with either L or D amino acids, since L amino acids are more abundant in natural systems and D amino acid resist common proteases and can present an additional stability. The third amino acid of the peptide is 3,4-dihydroxy-L-phenylalanin (DOPA) (FIG. 2).

To coat a substrate (e.g. gold, silicon, titanium, glass or polystyrene) with the peptide, we cleaned a bare substrate (1×1 $cm^2$) by sonication in ethanol, washing with water and drying under nitrogen. We incubated the substrates for several hours (3-10 hours) in a 0.5 mg/mL peptide in methanol. We chose this concentration of peptide since it formed a substantial coating that gave a good signal in various characterization methods. After incubation, we thoroughly washed the substrate with methanol and dried it under nitrogen. Due to the hydrophobic moieties of the peptides, water could not be used as a solvent system despite its high polarity. We used methanol as the solvent since it dissolved the peptide completely, and at the same time allowed it to adhere the substrate. Since methanol is a toxic solvent, we also examined other solvents with different polarities. When we used solvents, such as acetone, ethanol and isopropanol, with polarities that resemble the polarity of methanol, the peptide-based coating self-assembled in a similar manner to the methanol solvent system (FIGS. 3 and 4). However, in solvents with high polarity, such as dimethyl sulfoxide (DMSO) and 1,1,1,3,3,3-hexafluoro-2-propanol (HFP) the peptide dissolved but did not adhere to the substrate (FIG. 3).

In order to determine if the peptide indeed generated a "Teflon-like" layer on the substrates and increased their hydrophobicity we measured their contact angle. As we assumed, the modified surfaces (i.e. gold, silicon, titanium and stainless steel) exhibited an increase in the contact angle indicating an increase in the substrate hydrophobicity (FIG. 5). The contact angle of a titanium substrate coated with peptide 1 increased from 43.2° to 68.1°. Similarly, peptides 2, 3, 4, 5 and 6 followed the same trend (FIG. 6). We also found a correlation between the angle size and the concentration of the peptide solution, as the peptide concentration increased the contact angle was larger (FIG. 7).

To characterize the morphology of the modified surfaces we performed AFM topography analysis to mica and Ti surfaces coated with the different peptides (FIG. 8). The AFM analysis of the coated mica substrates indicated that the peptides decorated the surface. Spherical-like aggregates with a height of ~0.25-0.50 nm (peptide 1), ~0.20-0.48 (peptide 2), ~0.20-2.30 nm (peptide 3), ~0.32-0.65 nm (peptide 4), ~1.00-5.00 nm (peptide 5) and ~1.02-3.65 nm (peptide 6) appeared on the coated substrate. Due to the roughness of the titanium surface (Rq~0.866 nm) we could not detect any morphological changes on the surface (FIG. 9).

Figure 11:
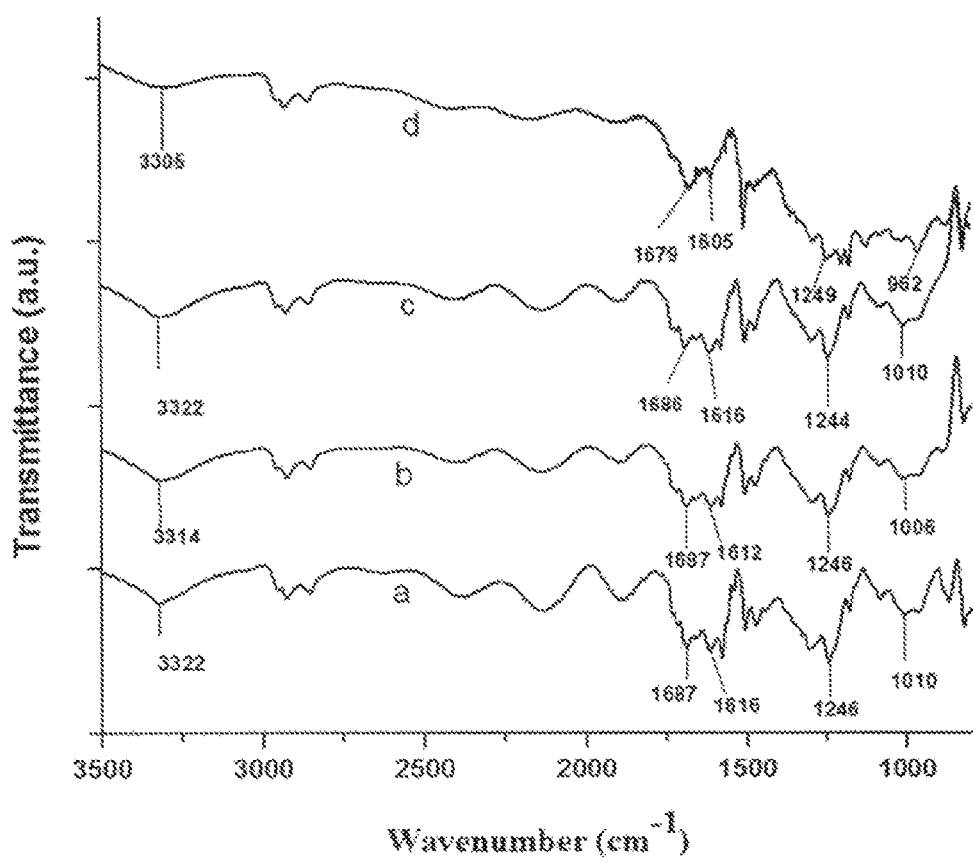
FIG. 11 presents ATR-FTIR spectra of titanium substrates coated with peptide 2 (a), 3 (b), 4 (c) and 5 (d).
Figure 12:
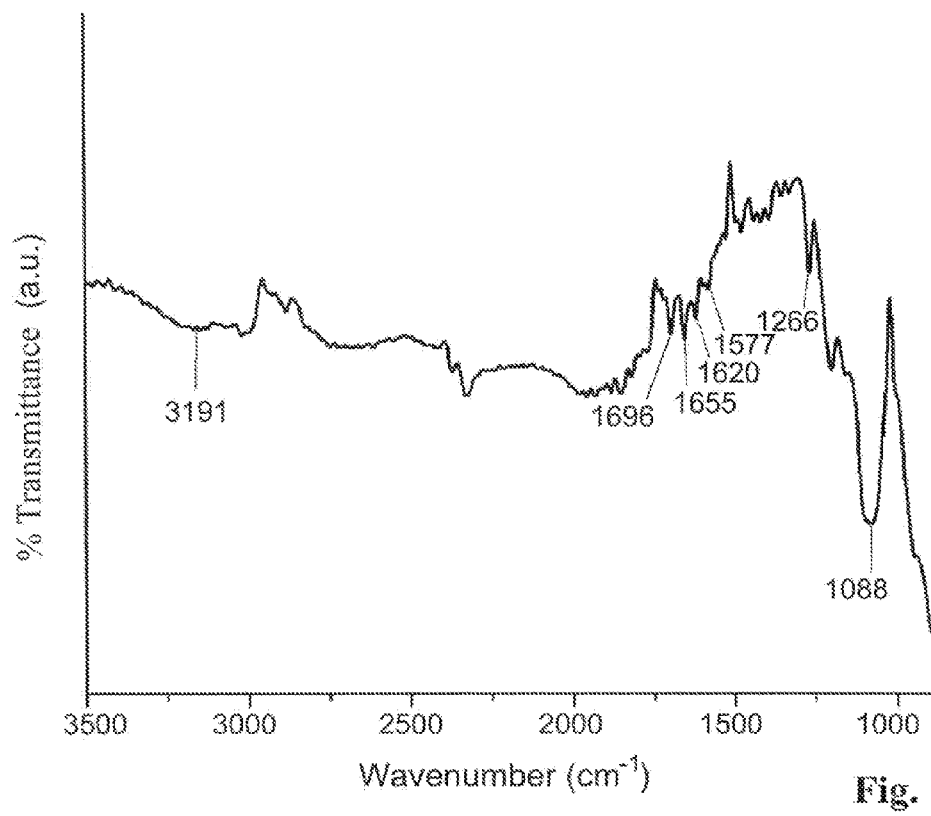
FIG. 12 presents ATR-FTIR spectrum of titanium substrate coated with peptide 6.

We also studied if the peptides indeed present on the substrate using ATR-FTIR spectroscopy. An informative IR frequency range is 3500-3200 $cm^{-1}$ as it corresponds to the N—H stretching vibrations and can indicate on the formation of a peptide film on the substrate. For a titanium surface modified with peptide 1, the N—H stretching frequency occurred at 3330 $cm^{-1}$. This IR frequency suggests the binding of the peptide to the substrate (FIG. 10). Similarly, the N—H stretching band occurred between 3305 $cm^{-1}$ to 3322 $cm^{-1}$ for surfaces modified with the additional studied peptides (FIGS. 11 and 12). Another informative region is characteristic of the C—F stretching band. Peptide 1 showed a peak at 1315 $cm^{-1}$, 1245 $cm^{-1}$ and 1093 $cm^{-1}$, while the spectra of the other peptides had a peak between 1310-1000 $cm^{-1}$ (FIGS. 11 and 12).

The IR region between 1800 $cm^{-1}$ and 1500 $cm^{-1}$ is related to the stretching band of amide I and can indicate on the secondary structure of the peptides. The ATR-FTIR spectra of a substrate coated with peptide 1 appeared at 1685 $cm^{-1}$ and 1629 $cm^{-1}$ indicating an anti parallel β sheet secondary structure. For peptide 2, 3 4 and 5 the amide I peak appeared at (1687 $cm^{-1}$, 1616 $cm^{-1}$), (1687 $cm^{-1}$, 1612 $cm^{-1}$) (1686 $cm^{-1}$, 1619 $cm^{-1}$) and (1679 $cm^{-1}$, 1605 $cm^{-1}$) respectively indicating the same type of peptide secondary structures on the substrates (FIG. 11). The IR spectrum of peptide 6 had a peak at 1620 $cm^{-1}$ (FIG. 12), however, the higher peak shifted to 1696 $cm^{-1}$, and another peak at 1655 $cm^{-1}$ appeared, indicating alpha helical structure. These may imply on less organized assembly of peptide 6 on the substrate. This can be supported by the intensity of peaks, and signal to noise ratio of the spectrum. When compared to the other spectra, the spectrum differs, and some of the titanium peaks seem to appear.

Figure 13:
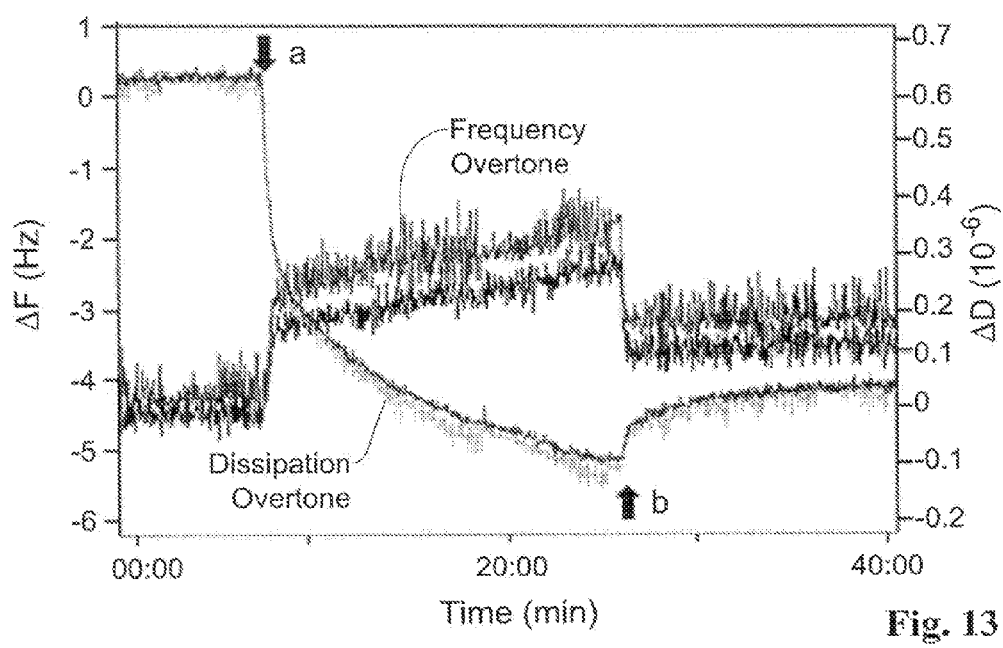
FIG. 13 presents Real-time QCM-D measurement For Peptide 1. Frequency (F) and dissipation (D) change upon adsorption of peptide 1 to Ti sensor. Arrows mark peptide addition (a) and washing (b).
Figure 14A:
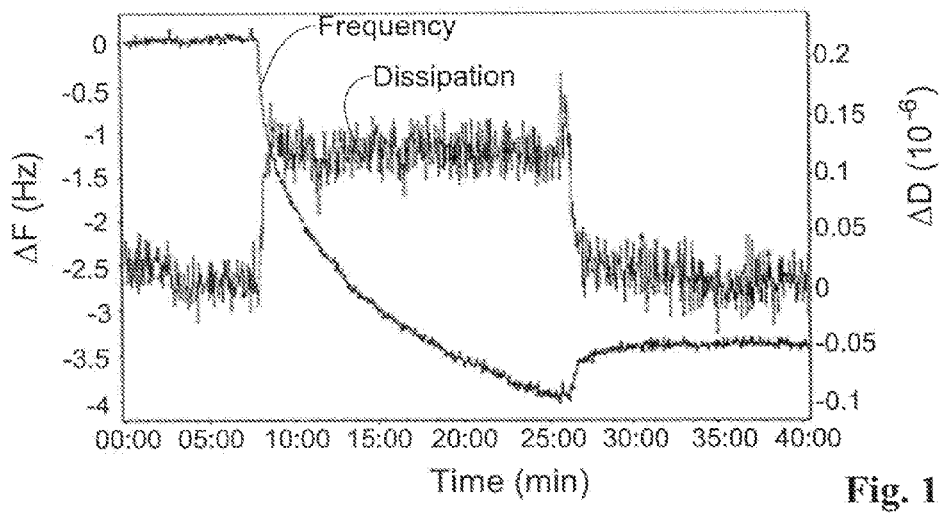
FIGS. 14A-14E present Real-time QCM-D measurements. Frequency (blue) and dissipation (orange) changes upon adsorption of peptide (FIG. A) 2, (FIG. B) 3, (FIG. C) 4, (FIG. D) 5 and (FIG. E) 6.
Figure 14B:
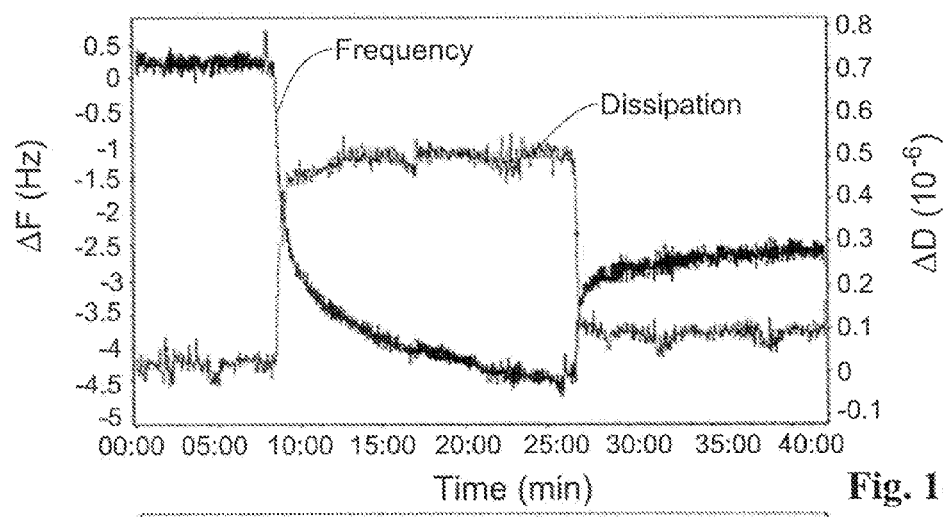
Figure 14C:
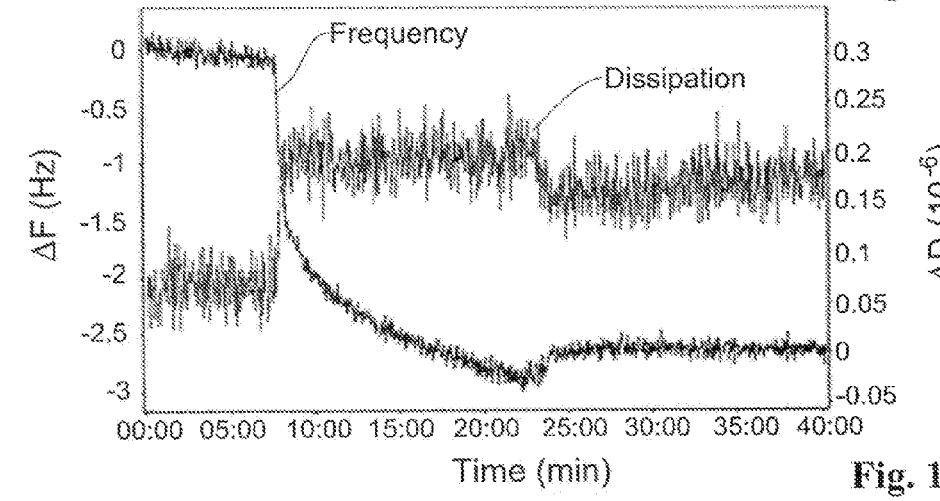
Figure 14D:
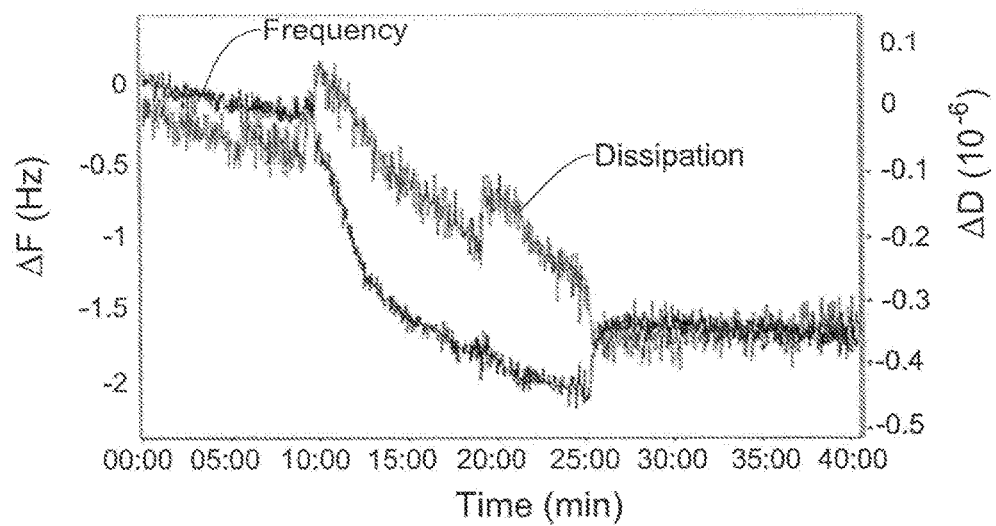
Figure 14E:
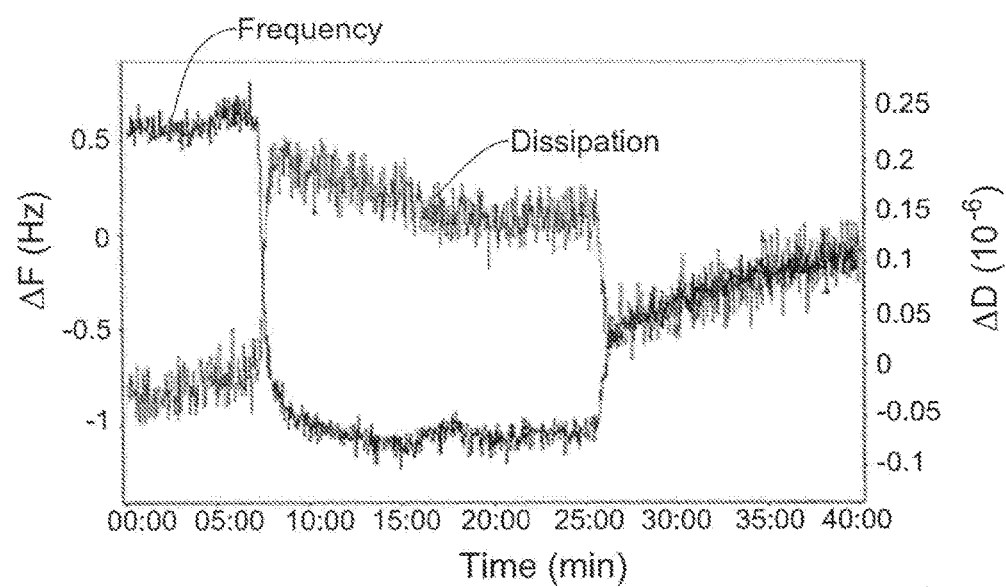

Using quartz crystal microbalance with dissipation mode (QCM-D) we studied the real-time adhesion of the peptides to titanium substrates. Each of the peptides dissolved in MeOH were injected into a flow cell containing a Ti coated sensor. The injection of peptide 1 resulted in changes in both frequency (f) and dissipation (D), this indicates on the peptide binding to the titanium substrates. Upon washing with MeOH, we only observed small changes in the frequency and dissipation; this indices the formation of a stable film on the surface (FIG. 13). Peptides 2, 3 and 4 exhibited the same trend, while the shifts resulted from the adherence of peptide 5-6 to the sensor were lower (FIG. 14) These differences suggest that the adhesion process is affected by the presence of fluorine atoms. The change in frequency is mass dependant, thus the smaller change in the case of peptide 6.

TABLE 1

Quantitative analysis of peptides 1-6, according to the Sauerbrey model.

|  | Peptide 1 | Peptide 2 | Peptide 3 | Peptide 4 | Peptide 5 | Peptide 6 |
|---|---|---|---|---|---|---|
| Thickness (Å) | 9.11 ± 0.05 | 7.3 ± 0.3 | 5.4 ± 0.5 | 5.6 ± 0.3 | 3.4 ± 0.5 | 1.7 ± 0.3 |
| Mass/Area (ng/cm$^2$) | 72.1 ± 0.4 | 57 ± 3 | 43 ± 4 | 45 ± 2 | 27 ± 3 | 13 ± 2 |
| Density (Kg/m$^3$) | 767 ± 4 | 824 ± 13 | 760 ± 37 | 769 ± 30 | 717 ± 44 | 805 ± 15 |

Figure 15:
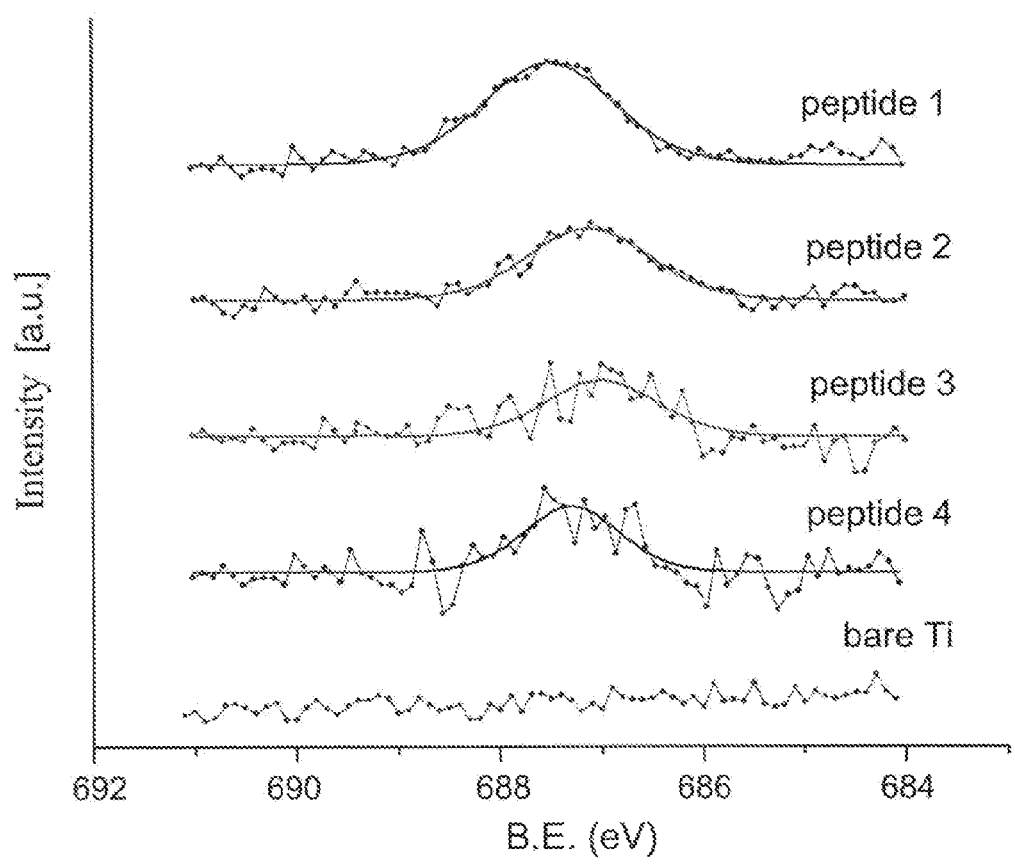
FIG. 15 presents XPS analysis of a bare Ti substrate, and substrates coated with peptides 1-4.
Figure 16:
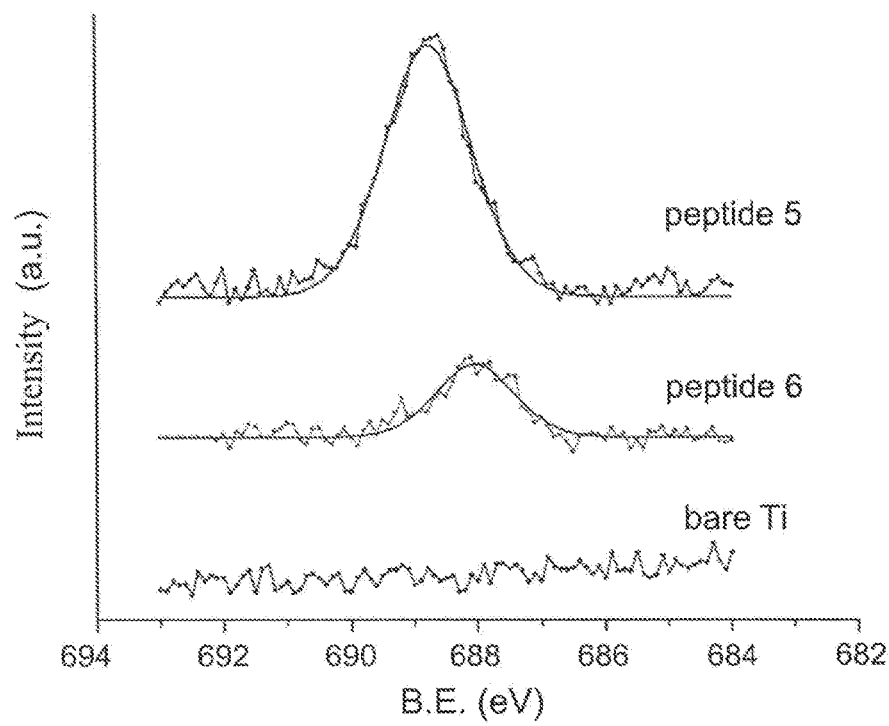
FIG. 16 provides XPS analysis of a bare Ti substrate, and substrates coated with peptides 5-6.

It should be noted that the QCM-D experiments lasted 40 minutes and therefore measured only the beginning of the coating process. Using X-ray Photoelectron Spectroscopy analysis we were able to characterize surfaces that underwent a prolonged incubation with the peptide to ensure the complete modification of the Ti substrates. In comparison to a bare Ti, the signals resulted from the modified substrates indicated the presence of carbon, nitrogen and fluorine. (FIGS. 15 and 16) These signals indicate a deposition of the peptide on the surface. The average thickness of the peptide layer evaluated by XPS was 3.9±0.1 nm, 4.3±0.1 nm, 3.9±0.1 nm, 4.41±0.03 nm, 4.2±0.1 nm and 3.82±0.04 nm for peptides 1-6 respectively.

We also determined the thickness of the coating using ellipsometry. By fitting the measurement to Cauchy film model, which is suitable for organic coatings, we evaluated a thickness of 3.41±0.05 nm, 3.46±0.04, 3.48±0.03 nm, 3.36±0.05 nm, 5.2±0.1 nm and 3.66±0.04 nm for peptides 1-6 respectively. These findings are with agreement with the results obtained by XPS analysis.

Figure 17:
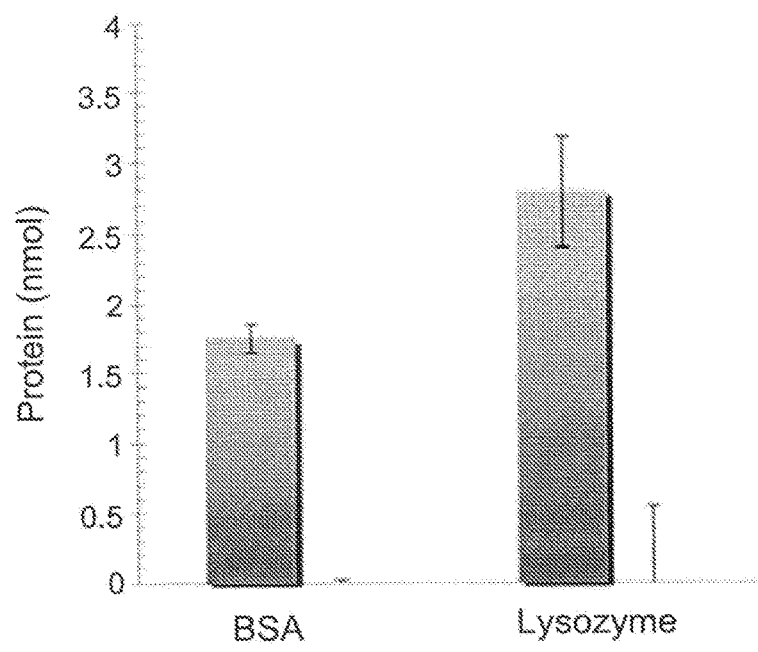
FIG. 17 shows Adsorbed amounts of BSA, and Lysozyme on Ti substrates and peptide coated Ti substrates (since the signal is very low only SD can be shown). Standard deviations are based on three different experiments.

The process of biofouling initiates by the adsorption of bioorganic molecules, in the form of polysaccharides or proteins, onto a substrate. These bioorganic molecules mediate the subsequent attachment of organisms. We, therefore, investigated the resistance of the peptide-based coating to protein adsorption. A bare Ti surface and a coated Ti substrate were incubated in a protein (either Bovine Serum Albumin (BSA), or lysozyme) solution at a concentration of 150 μM for 2 hours at 37° C. To determine the adsorbed amounts of the proteins on the substrates we used the non-interfering protein Assay™ kit. The adsorbed amounts of BSA and lysozyme on the peptide coated substrates were negligible and below the detection limit of the kit (FIG. 17).

To assess the bacterial attachment to the surface, bare and peptide coated substrates were incubated in inoculums of *P. aeruginosa* and *E. coli* for 9 and 96 hours respectively. These incubation times allowed the formation a biofilm by the different bacterial strains. After incubation, we washed and dried the substrates, and stained them with 2% (w/w) crystal violet. Crystal violet dye is part of the gram staining of bacteria and stains bacteria in purple. Using an optical microscope we observed a thick and dense purple layer on the bare titanium surface which indicated a thick bacterial coverage of the substrate, while on the coated titanium we only detected sparse bacteria (FIG. 18). To quantify this result, we extracted the crystal violet stain from the bacteria using 30% acetic acid and measured its absorbance. The absorbance of the crystal violet is proportional to the number of bacteria attached to the surface. For surfaces inoculated with *P. aeruginos* we observed a reduction of 93% in the amount of crystal violet on a coated substrate when compared to a bare substrate (FIG. 18). For surfaces inoculated with *E. coli*, a reduction of 72% in the amount of crystal violet was detected (FIG. 18).

Morphological Characterization of the Coated Substrates

Figure 19A:
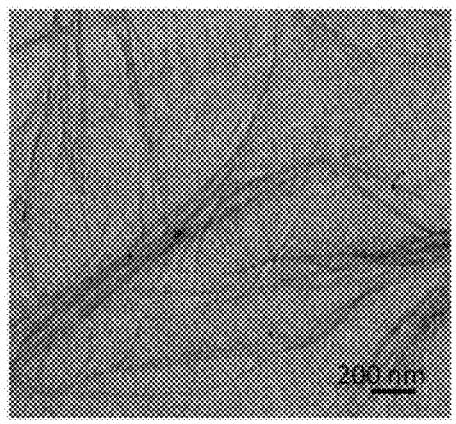
FIGS. 19A-19B show images.
Figure 19B:
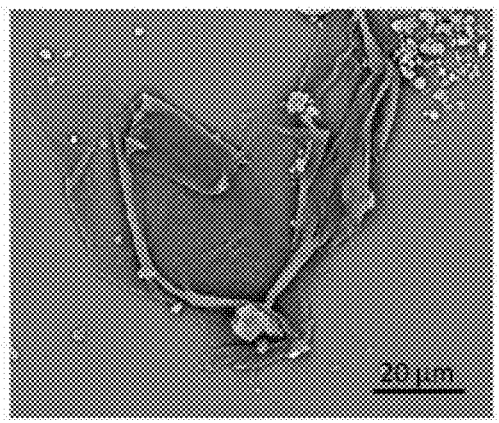

The peptide films were prepared by the dip-coating. Unless noted otherwise, all experiments were carried out with a peptide concentration of 0.01 mg/mL. The films were deposited on either silicon wafers, silicon wafers coated with a 100 nm of titanium layer or 400 mesh Copper-Formvar®/carbon grids. Using electron microscopy, the folds and defects in the film were identified, indicating the formation of a film on the substrate (FIG. 19).

Proteins Adsorption to the Peptide-Coated Surfaces

In order to determine if the peptide-based coating indeed resisted protein adsorption, the modified surfaces were incubated with FITC-BSA (a fluorescently-labeled protein). After a thorough washing, the presence of the adsorb protein to the surface was analyzed using fluorescence microscopy. Results from this experiment clearly showed a strong fluorescence signal indicating on an extensive protein adsorption on the bare silicon substrate when compared to the weaker signal from the modified surface.

Antifouling Activity of the Peptide-Coated Surfaces

To determine the antifouling activity of the peptides, the modified silicon surfaces were placed in BL21 *E. Coli* bacterial culture. The surfaces were then rinsed, sonicated in a buffer and the buffer was spread on agar plates and cultivated. The colonies were counted and the number of colonies forming units (CFUs) was calculated.

As indicated in Table 1, the number of CFU on the modified surface was lower by two orders of magnitudes when compared to the bare silicon surface.

TABLE 2

| | CFU per cm$^2$ of Si | |
|---|---|---|
| Bacterial strain | Bare Si | Si coated with the peptide |
| E. coli | $1.1 \times 10^5$ | $1.3 \times 10^3$ |

Surface Coverage

In order to establish the ability of the peptide to cover a substrate, peptide 8 was synthesized in such a fusion that an amine group would be located in a non-adjacent position to DOPA. Then, the peptide was conjugated to Fluorescein through its amine termini and deposited on a titanium substrate by dip coating. Results indicated the absence of florescent signal from a bare titanium substrate and a strong signal from the modified surface. This indicated that the peptide indeed coat the substrate.

The invention claimed is:

1. A peptide of 2 to 20 amino acids in length, at least one of said amino acids being 3,4-dihydroxy-L-phenylalanine (DOPA), at least another of said amino acids being fluorinated, and each of said amino acids being selected amongst aromatic amino acids.

2. The peptide according to claim 1, wherein each amino acid is bonded to said another amino acid via a peptidic bond.

3. The peptide according to claim 1, having the general formula A-L-F, wherein A is DOPA, L is a covalent bond or a linker moiety linking A and F, and F is a fluorinated amino acid moiety.

4. The peptide according to claim 3, wherein the linker being selected from substituted or unsubstituted carbon chain, optionally comprising two or more amino acids.

5. The peptide according to claim 4, wherein the linker having the general structure $$*-\!\!\!\left[HN-(CH_2)_n-\overset{O}{\overset{\|}{C}H}\right]_{\!m}\!\!-*$$

wherein
each * denotes a point of connectivity;
n is between 0 and 40; and
m is between 1 and 40.

6. The peptide according to claim 1, comprising two or more DOPA moieties or two or more fluorinated amino acids.

7. The peptide according to claim 1, wherein the amino acids are selected from the group consisting of tryptophan, tyrosine, naphthylalanine, and phenylalanine.

8. The peptide according to claim 7, wherein the amino acids are selected from phenylalanine and/or derivatives thereof.

9. The peptide according to claim 8, wherein the phenylalanine derivatives are selected from 4-methoxy-phenylalanine, 4-carbamimidoyl-1-phenylalanine, 4-chloro-phenylalanine, 3-cyano-phenylalanine, 4-bromo-phenylalanine, 4-cyano-phenylalanine, 4-hydroxymethyl-phenylalanine, 4-methyl-phenylalanine, 1-naphthyl-alanine, 3-(9-anthryl)-alanine, 3-methyl-phenylalanine, m-amidinophenyl-3-alanine, phenylserine, benzylcysteine, 4,4-biphenylalanine, 2-cyano-phenylalanine, 2,4-dichloro-phenylalanine, 3,4-dichloro-phenylalanine, 2-chloro-phenylalanine, 3,4-dihydroxy-phenylalanine, 3,5-dibromotyrosine, 3,3-diphenylalanine, 3-ethyl-phenylalanine, 3,4-difluoro-phenylalanine, 3-chloro-phenylalanine, 3-chloro-phenylalanine, 2-fluoro-phenylalanine, 3-fluoro-phenylalanine, 4-amino-L-phenylalanine, homophenylalanine, 3-(8-hydroxyquinolin-3-yl)-1-alanine, 3-iodo-tyrosine, kynurenine, 3,4-dimethyl-phenylalanine, 2-methyl-phenylalanine, m-tyrosine, 2-naphthyl-alanine, 5-hydroxy-1-naphthalene, 6-hydroxy-2-naphthalene, meta-nitro-tyrosine, (beta)-beta-hydroxy-1-tyrosine, (beta)-3-chloro-beta-hydroxy-1-tyrosine, o-tyrosine, 4-benzoyl-phenylalanine, 3-(2-pyridyl)-alanine, 3-(3-pyridyl)-alanine, 3-(4-pyridyl)-alanine, 3-(2-quinolyl)-alanine, 3-(3-quinolyl)-alanine, 3-(4-quinolyl)-alanine, 3-(5-quinolyl)-alanine, 3-(6-quinolyl)-alanine, 3-(2-quinoxalyl)-alanine, styrylalanine, pentafluoro-phenylalanine, 4-fluoro-phenylalanine, phenylalanine, 4-iodo-phenylalanine, 4-nitro-phenylalanine, phosphotyrosine, 4-tert-butyl-phenylalanine, 2-(trifluoromethyl)-phenylalanine, 3-(trifluoromethyl)-phenylalanine, 4-(trifluoromethyl)-phenylalanine, 3-amino-L-tyrosine, 3,5-diiodotyrosine, 3-amino-6-hydroxy-tyrosine, tyrosine, 3,5-difluoro-phenylalanine and 3-fluorotyrosine.

10. A peptide comprising between 2 and 20 amino acids, at least one of said amino acids being 3,4-dihydroxy-L-phenylalanine (DOPA) and at least another of said amino acids being a fluorinated amino acid selected from o-fluorophenylalanine, m-fluorophenylalanine and p-fluorophenylalanine.

11. The peptide according to claim 1, comprising DOPA at one termini and a fluorinated aromatic amino acid selected from o-fluorophenylalanine, m-fluorophenylalanine and p-fluorophenylalanine at the other termini.

12. A peptide selected from the group consisting of:

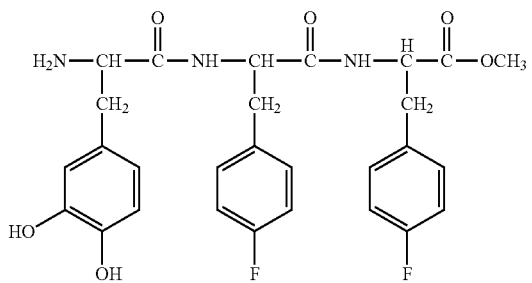

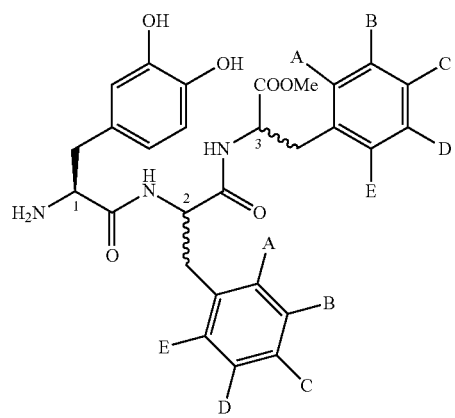

Peptide 1: (1S, 2S, 3S) A = B = D = E = ——H, C = ——F
Peptide 2: (1S, 2S, 3R) A = B = D = E = ——H, C = ——F
Peptide 3: (1S, 2R, 3S) A = B = D = E = ——H, C = ——F
Peptide 4: (1S, 2R, 3R) A = B = D = E = ——H, C = ——F
Peptide 5: (1S, 2S, 3S) A = B = C = D = E = ——F Peptide 6

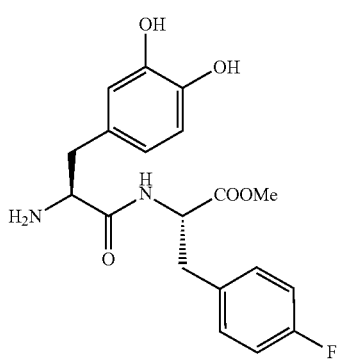

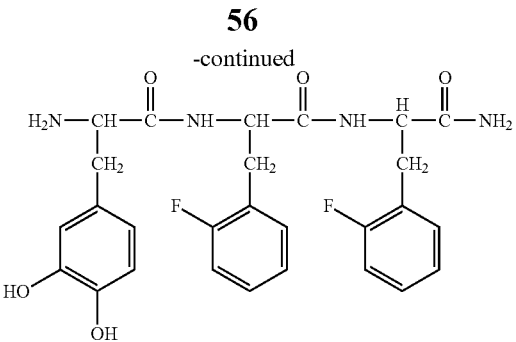

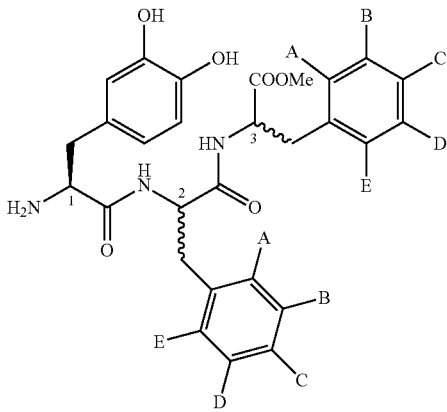

Peptide 7: (1S, 2S, 3S) A = B = C = D = ——H, E = ——F
Peptide 8: (1S, 2S, 3R) A = B = C = D = ——H, E = ——F
Peptide 9: (1S, 2R, 3S) A = B = C = D = ——H, E = ——F
Peptide 10: (1S, 2S, 3R) A = B = C = D = ——H, E = ——F

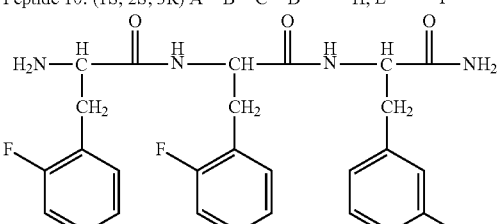

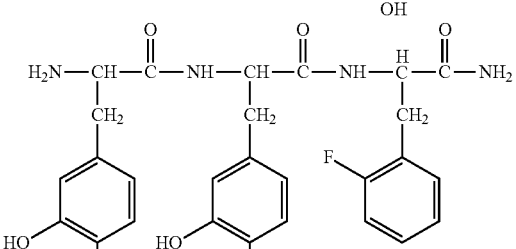

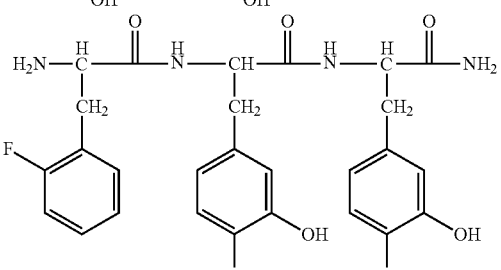

Peptide 15
NH$_2$—L—DOPA—L-(4-F)-Phe-COOH

Peptide 16
NH$_2$—L—DOPA—D-(4-F)-Phe-COOH;  and

-continued

Peptide 17

NH$_2$—L—DOPA—L-(4-F)-Phe-L-(4-F)-Phe-COOMe.

13. A formulation comprising a peptide according to claim 1.

14. A film comprising at least one peptide according to claim 1.

15. An article or a device comprising at least one surface region coated with a film according to claim 14.

16. A method for inhibiting settling, attachment, accumulation and dispersion of organisms, organism's secretion of an organic and/or bio-organic material on a surface, the method comprising contacting the surface with an effective amount of a formulation comprising a peptide according to claim 1.

17. A formulation comprising a peptide according to claim 10.

18. A film comprising at least one peptide according to claim 10.

19. An article or a device comprising at least one surface region coated with a film according to claim 18.

* * * * *